United States Patent
Krueger et al.

(10) Patent No.: US 9,474,934 B1
(45) Date of Patent: *Oct. 25, 2016

(54) BIOMETRIC ASSESSMENT IN FITNESS IMPROVEMENT

(71) Applicant: Fit Intuition, LLC, Reno, NV (US)

(72) Inventors: Ryan M. Krueger, Reno, NV (US); Lee Huber, Los Angeles, CA (US); Ralph Krueger, Reno, NV (US); Frederick G. Nesemeier, Reno, NV (US)

(73) Assignee: Fit Intuition, LLC, Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/960,459

(22) Filed: Dec. 7, 2015

Related U.S. Application Data

(63) Continuation-in-part of application No. 14/512,928, filed on Oct. 13, 2014.

(60) Provisional application No. 61/890,035, filed on Oct. 11, 2013.

(51) Int. Cl.
*G09B 7/00* (2006.01)
*A63B 24/00* (2006.01)
*G09B 5/02* (2006.01)

(52) U.S. Cl.
CPC ....... *A63B 24/0075* (2013.01); *A63B 24/0062* (2013.01); *G09B 5/02* (2013.01); *G09B 7/00* (2013.01)

(58) Field of Classification Search
CPC ...................................................... G06F 17/60

USPC ......................................................... 434/247
See application file for complete search history.

(56) References Cited

U.S. PATENT DOCUMENTS

| | | | | |
|---|---|---|---|---|
| 7,130,680 | B2 * | 10/2006 | Kodama | A61B 5/0537 600/547 |
| 2002/0091049 | A1 * | 7/2002 | Hisano | A63B 71/0686 482/148 |
| 2005/0240444 | A1 * | 10/2005 | Wooten | G06F 19/3481 705/3 |
| 2007/0219059 | A1 * | 9/2007 | Schwartz | A61B 5/0205 482/8 |
| 2009/0253554 | A1 * | 10/2009 | McIntosh | A63B 21/00 482/4 |
| 2011/0201476 | A1 * | 8/2011 | Solomon | A63B 24/0062 482/8 |
| 2013/0095459 | A1 * | 4/2013 | Tran | A61B 5/6816 434/247 |

\* cited by examiner

*Primary Examiner* — Sam Yao
*Assistant Examiner* — Alvin Carlos
(74) *Attorney, Agent, or Firm* — D. C. Williams

(57) ABSTRACT

In some embodiments, an automated system comprises one or more biometric sensors, an interactive screen, and an exercise routine generation application communicable with a mobile application. In some embodiments, the mobile application receives data from an automated station and displays exercise routines, other exercise information, or both. In some embodiments, the mobile application includes a scanner to scan labels, other indicia, or physical or other features of an exercise machine or other exercise apparatus to identify the machine or apparatus. In some embodiments, the mobile application communicates with one or more local or remote databases identifying differing exercise facility locations within a geographic area and identifying exercise apparatus available in each of the differing facilities.

20 Claims, 21 Drawing Sheets

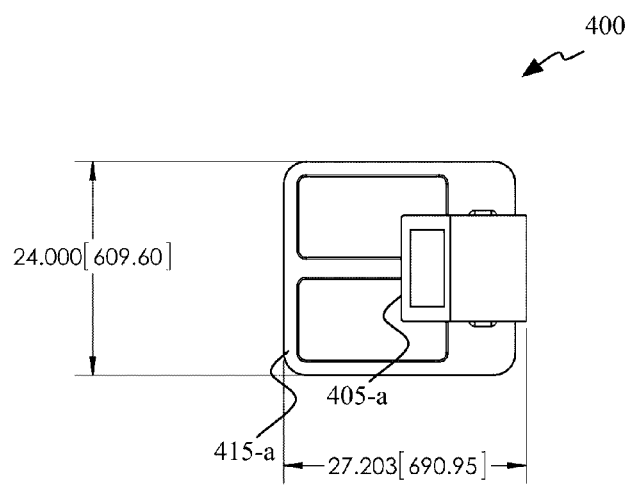
Figure 5
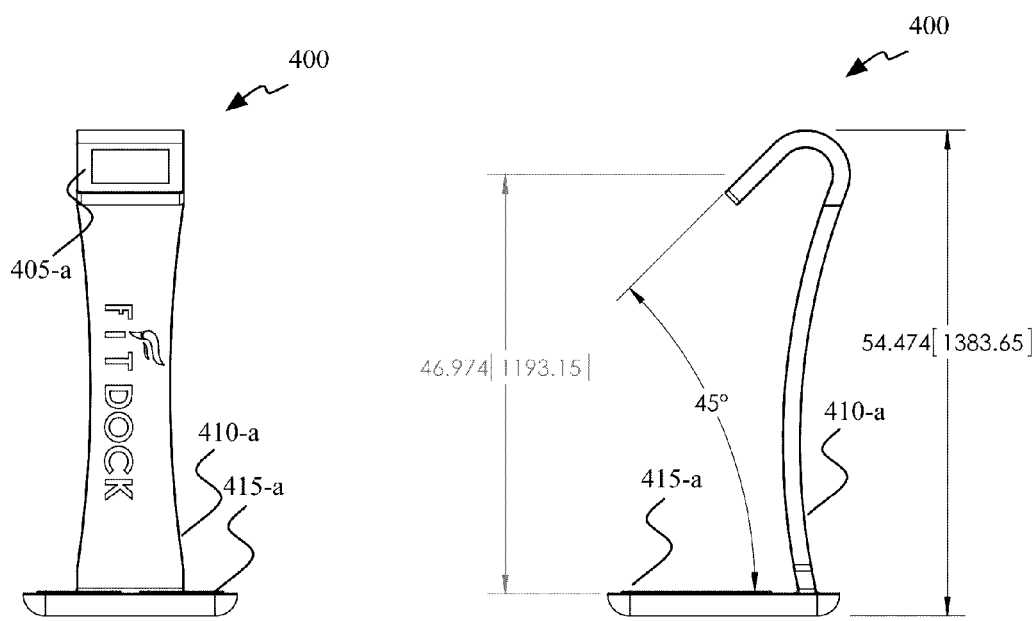
Figure 6
Figure 7

Base image created by Granito diaz; used pursuant to Creative Commons Attribution-Share Alike 4.0 International license

BIOMETRIC ASSESSMENT IN FITNESS IMPROVEMENT

CROSS-REFERENCE TO RELATED APPLICATIONS

This application is a Continuation-in-Part of pending U.S. Nonprovisional patent application Ser. No. 14/512,928 entitled "Biosensing Systems, Applications, and Methods" filed on Oct. 13, 2014, which application claims benefit of U.S. Provisional Patent Application No. 61/890,035, also entitled "Biosensing Systems, Applications, and Methods" and filed on Oct. 11, 2013. The instant application claims benefit of, and incorporates herein by reference in their entireties for all useful purposes, both of the applications above (Ser. No. 14/512,928 and 61/890,035). In the event of any inconsistency between the prior patent applications and the instant application (including without limitation any limiting aspects), the instant application shall prevail.

COPYRIGHT NOTICE

This patent document contains material subject to copyright protection. The copyright owner has no objection to the photocopy reproduction of the patent document or the patent disclosure in exactly the form it appears in the Patent and Trademark Office patent file or records, but otherwise reserves all copyright rights to its original work. To the extent that any material herein may legitimately fall within the scope of any copyright protection previously claimed by another party, including material presented herein potentially subject to the "Fair Use" doctrine, Applicant disclaims any intellectual property ownership thereof or copyright protection therefore.

FIELD OF DISCLOSURE

The present disclosure relates to an electronic fitness improvement system that utilizes biometric information from and about users to generate personalized exercise workout information.

BACKGROUND

Biometric sensor systems are known in the art. A prior Internet publication regarding a Tanita "MC-980 Multi Frequency Segmental Body Composition Meter" (the "Tanita reference") describes a biosensor information collection system having a automated stand/station with a scale at the base of the stand and a digital display at the top of the stand. The publication further explains that a height measurement accessory is optional.

Prior art biometric sensors are generally configured to determine the body fat of a user via the imposition of a low voltage alternating current (AC) between electrodes in contact with at least two points of said user's body. The complex impedance of the user's body between said points of contact, comprising a real (resistive) component and an imaginary (reactive) component, determines the current flow between said points. Expressed in alternative language, a small current is imposed at one electrode, said current flows through the user's body to another electrode, and the voltage between the two electrodes is measured. In accordance with the inherent definition of impedance, a user's bioimpedance is defined as the ratio of the analog voltage applied between any two of the two or more sensors in communication with a user's body to the analog current measured to flow between said sensors. Accordingly, two sensors are required for any measurement, and the use of more than two biosensors permits the measurement of bioimpedance between each pair of two sensors. Where a measured scalar value is acceptable for the use at hand, only the magnitude of the current and voltage need be obtained. Whenever the true nature of the complex impedance is required to permit analysis of both resistivity and reactance, which in turn enables determination of other characteristics such as relative permittivity, the phase relationship between the measured current and voltage must also be known. Raw data from this measurement is then correlated with other data, including but limited to an estimate of the volume of the user's body and calibration information specific to the hardware, to estimate the body fat content of the user. Whenever used herein, the term "bioimpedance" refers to the analog ratio of an AC voltage at one or more frequencies between a particular pair of biosensors in communication with a user's body to the current flowing through said body between the same two sensors. This is an analog quantity, whether in scalar or complex form, and it should be understood that its measurement requires the use of one or more specialized analog machines. Said specialized analog machines include but are not limited to an AC generator capable of producing at least a sinusoidal output, but in some embodiments the AC generator may also be configured to produce waveforms of other types such as square waves, triangular waves, ramp waves, sawtooth waves, and frequency-domain comb waves comprising simultaneous components of specified frequencies and amplitudes. Other specialized machines required for bioimpedance measurements include analog voltage measurement devices and analog current measurement devices. These are known in the art to comprise the analog components necessary to measure the analog quantities of voltage and current, which may subsequently be converted to digital form via known analog-to-digital (A2D) conversion. This subsequent conversion does not alter the fact that the voltage and current components, and the bioimpedance represented by their ratio, are unquestionable analog quantities and that their measurement and determination cannot correctly be deemed to be any form of computer-based process or method.

Whenever used herein, the term "biodata" typically refers to the combination of the user's measure bioimpedance data in conjunction with the user's measured weight, both of which are data obtained from measurement of at least one biological characteristic of a user's body. However, in some contexts, the terms biodata and bioimpedance used with reference to data may pertain to either the bioimpedance data or the weight data separately, since both may be characterized as elements of a user's biodata.

A method known in the art to estimate the user's volume is to scale the impedance measurement with the square of the user's height. However, this method fails to account for the cross-sectional area of the user's body that is equally important in any calculation of body volume. While this electrical determination method is generally not as accurate as other methods, such as hydrostatic weighing methods, it is often preferred because it is fast, non-intrusive, and requires a minimum of external equipment. While the prior art teaches the use of this hardware for simple body fat determination, it fails to disclose the use of this hardware for more extensive assessment and characterization of users' bodies, thereby leaving any number of needs unmet for which such assessment and characterization may be highly beneficial.

The system disclosed in the Tanita reference is not an exercise development system. For example, the system as disclosed in the Tanita reference does not provide any exercise recommendations, much less do so by identifying specific exercises to be performed on identified exercise equipment. The system of the Tanita reference also does not connect with a mobile application that may be utilized to collect data about specific exercise apparatus or specific exercise facilities. There are many other aspects of the present disclosure not disclosed in the Tanita reference.

Mobile exercise development applications have also been disclosed in the prior art. One such reference, U.S. Published Patent Application No. 20130196821 (the '821 reference), discloses a mobile exercise development application that collects biometric information about a user, collects data about available exercise machines (such as with a scanner on the mobile device), and, with both of these types of information, generates customized exercise routines for the user.

The '821 reference does not disclose an automated biometric information collection station much less use of such a stand to provide the biometric data to a mobile exercise development application. The '821 reference also does not disclose use of information generated by the application, such as exercise apparatus identification data for apparatus in particular locations, to provide a database of exercise apparatus at differing such locations.

Further, to applicants' knowledge, the prior art does not include any such database compilation of exercise facilities by location much less one accessible by a mobile application. Although Google maps and other mobile applications have long tracked and reported a mobile device user's location and directions to differing identified locations, to applicants' knowledge such prior art applications have not provided an identification of differing exercise facility locations along with identification of exercise resources, such as particular machines, available at the locations respectively. Similarly, they have not provided automatic identification of the subset of locations available locally to a mobile application/device user. And, mapping features have not been provided with any such features to applicants' knowledge.

The applicants believe they have discovered problems and deficiencies in the prior art such as those set forth above and others solved by one or more embodiments disclosed in this specification.

SUMMARY OF SOME ASPECTS OF THE INVENTION

The automated system disclosed herein comprises stand-alone exercise workout generation apparatus, systems, and methods designed to meet the specific needs of each user based on information provided by the user, newly-collected and previously-stored data obtained from direct measurement of the user, exercise resource information compiled via other methods described herein, and a workout generation engine configured to apply best practices in the art and science of physical conditioning. It is envisioned that the preferred embodiment(s) of this invention will provide all of the benefits of a human personal trainer via a relatively inexpensive automated system entirely separate from, and not in communication with, any other apparatus, device, or machine used to actually perform specific exercises. This is a substantial advantage over known system which require communication with one or more other devices in order to obtain data from users for the purpose of generating exercise workout recommendations, often in real time as exercises are actually being performed. Such systems are both complex and expensive, rendering them unsuitable for use in small facilities such as limited fitness facilities often afforded by hotels and larger companies for the benefit of their employees. Due to its comparatively lower cost, small footprint, and extreme versatility and extensibility, the present invention is well-suited for such applications and provides equivalent functionality in most regards as will be described in greater detail below. As such, it solves a problem known in the art and fills a need in the burgeoning field of personal fitness services.

A further advantage of Applicant's apparatus and systems is that it is compatible with any type of exercise equipment, including exercise machines lacking the capability to communicate electronically with more sophisticated devices and systems that monitor user performance in real time and incidentally provide workout recommendations. A simple fitness facility that offers only free weights, a pull-up or chin-up bar, and floor mats has absolutely no use for a system that requires integration with a complex elliptical trainer, electronic stationary bicycle, or a comparable device that requires sensors and other monitoring paraphernalia attached to the user while the user is performing exercises. Applicant's invention is perfectly suited for such facilities, and by virtue of its novel methods of exercise generation, will provide essentially equivalent results at a mere fraction of the cost. In other words, one of the novel aspects of Applicant's invention is its lack of reliance on any other equipment or data source. It is a self-sufficient, stand-alone system that provides no actual physical exercise performance for the user and operates independently of any form of exercise apparatus or machine.

The apparatus and systems disclosed herein are principally directed toward individual users and patrons of a wide variety of public and private facilities, including but not limited to health clubs, gyms, hotels, motels, municipal recreational locations, and private apartment complexes that offer exercise facilities to guests and residents. Many such facilities provide exercise equipment with little or no guidance for users; the system described herein will advantageously provide much-needed support for those users. Further, the apparatus and systems are not necessarily directed exclusively to commercial entities. Some embodiments of Applicant's invention are suitable for purchase and by individuals, particularly those who represent the higher end of the retail exercise machine market.

Although the systems and methods herein are suitable for one-time exercise generation, an important advantage over known systems is that the present invention is configured to retain historical data for each user and generate exercise workout recommendations on an on-demand basis for an open-ended period (as long as the user wishes to continue using the system) based in part on a user's present preferences as well as prior activity. In some embodiments, the system is operative to receive a set of preferences and goals from a user and prospectively generate workouts on demand that direct the user toward achieving said goals via the user's preferences. Each new exercise workout may draw upon the user's exercise history and other relevant data so that the optimal updated workout is always available to each user. For the purpose of the instant disclosure, the terms "prospective" and "prospectively" are used to refer to exercise workouts based on assessment of a user's past and present data with results of the prescribed exercises being extrapolated forward (prospectively) toward any goals established by the system or supplied by the user without any previous confirmation of efficacy other than best practices in the art of exercise generation. For example, a certain exercise that burns sufficient calories would be expected by best practice assessments to produce a weight loss in a particular user if included in exercise workouts. When it is prescribed as a part of an exercise workout for an overweight user based on the user's past and present data and reliance on that best practice assessment, said exercise workout is deemed to be prospectively generated because the anticipated future results are extrapolated from present and past data only. No confirming data exists that the anticipated results will actually be achieved is available in methods of prospective workout generation.

Another novel feature of the disclosed system and methods is the anonymous association and aggregation of users' data, exercise workouts generated by the system, and the results achieved by the community of users. Applicant is not aware of any present resource that provides a compilation of such data permitting correlation of the effectiveness (or lack thereof) of certain exercise practices based on characteristics of users, including weight, bioimpedance, age, sex, present physical condition, body type, and the like. Over time, as exercise workouts are provided by the system and are performed by users while biometric data, user preference data, and user goal data are obtained and anonymously aggregated, extensive information will be available to assess the efficacy of particular exercises and combinations thereof for different types and characteristics of users. This historical data may therefore be used to further refine and improve the exercise workouts provided by the system in conjunction with, as a supplement to, or in lieu of the prospective exercise workout methods disclosed herein. When aggregated historical results of other users are incorporated in the generation of exercise workouts as described elsewhere herein, said workouts are no longer simply prospectively-based but now also comprise at least some degree of anticipated success or failure based on historically-demonstrated actions and results. In this sense, use of historical data permits a degree of interpolation between a user's past and previous exercises and results, and the exercises and results obtained by similar users, so that the former may be adjusted as desired to conform to the latter.

In one embodiment, the system is configured in a manner that permits users to register and interact anonymously with the automated system without any link to their real identity. In this embodiment, providing a user's real name is not required for participation; a pseudonym may be provided to the system by the user in lieu of their real identity, and any fee payments may be completed via means that do not establish a traceable link between the source of payment and the user's system profile. This additional measure of security provides additional protection for users who may prefer to enhance the privacy of their personal information and bio-data.

In one aspect, the present specification is directed to an automated system having one or more biometric sensors, an interactive screen, and an exercise routine generation application. In some systems, the automated system comprises an automated station including a support arm extending from a weighing scale to the interactive screen supported by the support arm.

In some embodiments, the automated system further comprises a mobile application provided to system users that is communicable with various components of the system for the purpose of receiving data from the automated system and displaying exercise routines or other exercise information to a user, for example. In some embodiments, the mobile application can include a scanner to scan labels, other indicia, or physical or other features of an exercise machine or other exercise apparatus to identify the machine or apparatus. Such identification may then be communicated to a networked database in association with the location of the machine or apparatus so that its existence and location may become known to other system users. In this manner, a large database of exercise machines and apparatus may be compiled from "crowd sourced" contributions of the vast body of users, thereby forming a more comprehensive aggregation of exercise resources than could be compiled by any other means.

In this and other embodiments, a mobile application also communicates with one or more local or remote databases to identify differing exercise facility locations within a geographic area and identify exercise apparatus available in each of the differing facilities within that geographic area or locale. In some systems, the mobile application/device can include a scanner such as identified above to identify exercise resources available a given facility and place that information into the one or more databases. The mobile application may access any location service data available from the host device, such as without limitation GPS data, cellular site information, WiFi access point SSID and its associated location, and the like. Said location service data may be associated with the identification of exercise resources transmitted to the one or more databases so that the location of said resources is generally known. As location service data is often not highly accurate, in one embodiment the mobile application user is presented with a list of known facilities in the general area corresponding to the location service data of the device and afforded an opportunity to select the correct facility. Such facilities may include, but are not limited to, health clubs and gyms, publicly-accessible facilities, hotels and motels, apartment complexes, municipal facilities, and the like. In one embodiment, a user may be prompted to enter a ZIP code or other location-specific information and system resources will be used to retrieve proximate locations of exercise equipment, specific exercise resources such as equipment at said locations, a list of exercises that may be performed on said resources, or any combination of the above.

In one embodiment, the one or more databases comprising exercise resources are primarily compiled from information provided by owners or administrators of said resources. In one embodiment, said databases are primarily compiled from information provided by users of the mobile application. In one embodiment, said databases are primarily compiled from information provided by any interested person.

In one embodiment, the mobile application may be configured to present to a user a list of all exercise resources known to the one or more databases in an identified facility for the purpose of verification. As resources are replaced or removed, previously-submitted information may no longer accurately reflect the resources available at a facility. Providing one or more means within the system to maintain accurate information in said databases via update mechanism(s) is preferred. In this manner, the crowd-sourced advantages of the user-generated database of exercise resources and their locations may be continuously updated with the same degree of attention from the entire base of system users rather than relying on just a handful of administrators.

In embodiments where information may be provided by mobile application users, said users may be incentivized to obtain, submit, or update information regarding available exercise resources. For example, users who discover and submit resource and location information not previously known to the system, or who verify the resources available at any given facility, may receive consideration in return, including but not limited to cash compensation, merchandise or merchandise credit, promotional credit, or credit toward any subscription or participation fees associated with their use of the system.

In certain embodiments, the one or more databases comprising exercise resource information may further comprise data pertaining to the specific exercises for which said resources are suitable. These associated exercises are preferably obtained from the manufacturers or suppliers of the hardware most familiar with the capability of said equipment, stored in the one or more databases, and used to populate fields in the relevant database(s) whenever a particular resource and its location are reported and added. Alternatively, if it is desirable to store the resource data in a first database and the applicable exercises for each resource in a second database, said first and second databases may be linked in any of the known ways to associate the data in each one with the appropriate data of the other. In another embodiment, users, owners, or administrators of said resources may provide such associated exercise information when the resource is first reported and added to the one or more databases. For example, exercise resources belonging to the family of treadmill-type machines are suitable for the exercises of walking, jogging, or running. Certain machines in that family, if configurable to provide a sufficient incline, may be suitable for use where stair-climbing exercises are prescribed in a generated exercise workout. Both free weights and exercise machines offering controllable resistance are generally suitable for arm, chest, and shoulder muscle development, but only the controllable resistance machine may be deemed suitable for exercises performed by older or injured users where the use of free weights would be dangerous and impractical for those users. In short, the system is configured to receive, store, and provide a list of exercise resources within a certain geographical area, along with a list of exercises associated with each such resource, for the purpose of exercise workout generation described in detail elsewhere herein.

In certain embodiments, users can access exercise facility information through their mobile devices. For example, a mobile application can procure the user's location via the device's location service data to procure and display local exercise facilities and their respective exercise resources.

In certain embodiments, the automated system or an automated station is communicable with the mobile application that reports differing exercise facilities within a defined geographic area and exercise apparatus available in said facilities. The mobile application/device can include a scanning feature such as set forth above. In some embodiments, the mobile application or web or other portal can provide the user with locations of exercise facilities that have certain equipment, such as the automated station disclosed herein, compatible with the user's mobile application or other equipment that the user can use to otherwise access the user's information provided earlier such as, for example, for storage in one or more databases. Some systems can include all the features identified above. Additional features of the automated system, automated station, or mobile application include information or instructions for how to perform an exercise and/or graphic or video demonstrations of exercises with identified apparatus.

In some embodiments, the automated station can act as a personal trainer that generates workout recommendations, video tutorials, and specific body group exercises. For example, the automated station can provide the ability to help patrons of small unmanaged gymnasiums and unsupervised fitness rooms by providing a step-by-step guide for fitness instruction.

In some embodiments, the automated station can report damaged equipment to managers, etc. The automated station also can communicate with an optional mobile phone application that offers a handheld guide to user. The station can further provide a complete resource for small to large gymnasium/complex utilization.

In some embodiments, the automated station, mobile application (such as those compatible with an iPhone, iPad, iPod, or other smartphone or mobile device), or both may include at least one of any of a login to keep track of body stat information (weight, body fat percentage, muscle mass, other physical characteristics, etc), a nutrition guide, a customized periodic workout regimen for a user with adaptation when needed for a user using differing types of equipment (either in the same facility or in varying types of exercise facilities), user workout tracking data collection and reporting, video or graphical tutorials on equipment use, and GPS capabilities to locate an apartment or other exercise facility in a particular geographic local, in some embodiments with a map layout of the facility and identification of exercise resources in the gym.

With an integrated system including the automated station and the mobile application/device having user location tracking, mapping, and exercise resource identification features, a user can travel and yet easily locate and follow mapping instructions to find a suitable exercise facility if available in the user's geographic locale.

In some embodiments, the mobile application/device may also include at least one of any of a QR code, bar code, or other code scanner function for scanning and identifying exercise (or other) resources in the exercise facility, safety information, means to submit damage reports to complex manager, means to communicate with or find partners in the same facility, means to chat in linked forums about workouts and health matters, and means contact a facility manager about concerns.

In one embodiment, data representing an exercise workout generated by one or more resources in the automated system may be communicated to an electronic device in the possession of, or accessible to, either a user or a third party designated by a user on said user's behalf. The exercise workout data may be communicated to, and be available for presentation by, the electronic device to the user or his designee via the mobile application running on any suitable electronic device.

The exercise workout data may comprise at least one or any combination of different formats. A first exemplary format may comprise any or all of a written list of specific exercises, their order of performance, durations, intensity, and the length of intervening rest periods. This first format provides a concise listing of the exercises for quick user reference. In lieu of, or in addition to, said written list, one or more icons representing each exercise and related information may be provided. The exercises and related information may be conveyed to the user via the use of different images, colors, sizes, or other visual distinctions between the various data.

A second exemplary format may comprise one or more video presentations depicting a trained professional properly performing each exercise. Preferably, said exercises are depicted in the order prescribed in the exercise workout, each with the number of repetitions corresponding to the exercise workout and performed at the correct rate for said workout. The video presentation may be comprised of short segments, each with one or more repetitions, combined into the larger presentation in the order and quantity necessary to conform to the prescribed exercise workout along with the proper periods of rest added between each exercise or exercise set. This video presentation will permit the user to perform the exercise workout at the correct pace by following along with said presentation while simultaneously observing the proper exercise methods and form.

A third exemplary format may comprise a video display other than that of an exercise professional, such as an animated display of any type (with abstract or quasi-realistic images) with appropriate audio cues, including but not limited to sounds, tones, music, or voice instructions provided at the correct pace (tempo) to accompany the user's exercise workout. In this manner, the user would not be constrained to watch the video display while exercising but may receive video, audio, or video and audio clues or guidance as desired to assist the completion of their exercise workout.

Data pertaining to an exercise workout may be communicated to and stored by the electronic device by any known means, including but not limited to a wired connection method known in the art via a USB, Firewire, optical, or any other type of direct wired connection, by a wireless connection method known in the art via a WiFi®, BlueTooth®, ZigBee®, NFC, infrared, or any other manner of free space propagation, by transfer of data via a memory chip, card, or other device upon which data is stored when connected to a component of the system and retrieved by the electronic device when later connected thereto, or by any other known or later-developed means of data transfer. Any communication protocol compatible with the chosen means of communication may be utilized. In this embodiment, the exercise workout data is stored within the memory of said electronic device and may be accessed and displayed by the user or his designee on demand.

In one embodiment, the data pertaining to an exercise workout may be streamed in real time to an electronic device at the position of, or a position proximate to, a user. Such streaming may be sent to a mobile device such as a smartphone, tablet, or any similar or compatible device via one or more wireless connections as described above. Alternatively, or additionally, said exercise workout data may be streamed via any wired or wireless connection to any compatible display mounted in a visible location, such as a wall proximate to the user's exercise location. Alternatively, or additionally, any audio portion of said exercise workout data may be communicated to a wireless audio receiving device, such as BlueTooth®-enabled headphones or similar devices, communicated to a BlueTooth®-enabled device operatively connected to wired or wireless headphones or similar devices, or communicated to a user in any manner that provides equivalent results. Whenever exercise workout data is streamed to any device, the requirement for said device to store such data is removed. This embodiment is particularly useful when the exercise workout data is too large to be conveniently stored on said device.

In one embodiment, any portion of the data and information in a user's profile resident within the automated system and any of its component devices and resources may be communicated to said user upon request. Such user profile data includes data provided by the user, all measured data obtained by the system, the content of all exercise workouts generated by the system, and all other data associated with the user's interaction with the system with corresponding dates and times. Such data may be provided by the automated system to the mobile application disclosed elsewhere herein or provided to the user via any other preferred means. In this manner, the user or his designee will be assured of having full access to his own data for any desired purpose beyond the functions provided by the automated system.

Systems disclosed herein can provide novel methods of using the systems, including novel business methods. Any conceivable combination of fees or associated privileges are envisioned by this disclosure, illustrated by the following non-limiting examples.

Use of the automated system by a user will necessitate the establishment of a business relationship between said user and the operator of the automated system. Such relationship may involve, in some embodiments, the payment of fees by the user for services provided by the automated system as disclosed below, thereby establishing a direct financial relationship. In other embodiments, use of the automated system may be provided to users without charge. In those cases, some other non-financial form of business relationship will necessarily exist between the automated system operator and the user. Even when no direct financial transaction occurs between the user and the automated system operator, the exchange of information between the user and the automated system still creates a fundamental business relationship between said parties wherein services are offered by the automated system operator and the user and the user accepts any conditions of participation and receives such services. However, any number of other business relationships between the user, automated system operator, and third parties are possible. As the automated system and its components, comprising among other resources automated station(s), mobile application(s), and network infrastructure obtain information from many sources and provide such information and useful services to other parties interacting with the system, any number of commercial activities and business models are enabled by this invention and will be immediately obvious to a person of ordinary skill in the art and are envisioned by this disclosure.

One novel business method may involve charging users a fee to subscribe to the services provided by the automated system, automated station(s), and mobile application(s), including but not limited to using the mobile application to generate database(s) identifying the types of exercise apparatus available in each of differing exercise facilities, using the automated station(s) to input user data, measure biodata, and generate exercise workouts, and benefit from any or all of the system features. Some services of the automated system may be provided to users without charge and others may be classified as "premium services" subject to a fee.

Purchase of a use license for the mobile application may entitle the user to visit one or more exercise facilities also subscribing to the service at no additional charge on a limited or continuing basis. In another embodiment, the use license for the mobile application is provided free to users but exercise facilities located and selected by said application remit a fee to the system operator for every mobile application user who patronizes said exercise facility.

Facilities offering access to exercise equipment, including the automated station disclosed herein, may provide compensation to or receive compensation from the system operator for the privilege of being included in the one or more databases, particularly with preferential placement or recognition. Users who learn of particular facilities and incorporate them into the system may receive a discount applied toward any fees required to participate.

In one embodiment, use of the mobile application and other components of the automated system are provided free to users who consent to share their contact information for the purpose of receiving targeted advertising material. In one embodiment, exercise equipment manufacturers may remit a fee to the system operator for the privilege of providing product information on consumer-grade exercise equipment products to users whose exercise history or user preferences are compatible with said manufacturer's product offerings. Further, advertising in conjunction with any or all the services provided by the automated system, exercise facilities, and exercise resource/equipment may also provide a source of remuneration for any of the parties associated with operation of or participation in the automated system. All are envisioned herein and included within the scope of this disclosure.

One additional example of a business model enabled by the system involves the participation of third party personal trainers and other professionals via the oversight of exercise workout programs of users. A primary advantage of the automated system disclosed herein is that the system provides users with an equivalent level of guidance and expertise in exercise workout generation as do personal trainers or fitness consultants. Just as the human trainers and consultants do, the automated system considers all of the pertinent factors necessary to generate a safe and effective exercise workout for a user, but at a significantly lower cost to the user in many embodiments. However, under certain circumstances, automated system users may desire to include participation of a human trainer in their activities related to the automated system. For example, and without any limitation on the applicability of other examples or embodiments, a trainer's client may wish to perform a certain portion of his exercise workouts in a facility distant from his normal location due to travel requirements and seeks to allow remote supervision by his trainer. A client with special requirements, such as those of a professional athlete under the supervision of team medical personnel, may be required to maintain close coordination with said personnel to ensure that appropriate activities are being prescribed and performed. Lay persons under medical supervision, perhaps following surgery or a heart attack, may prefer to include their physician's supervision of all exercise activities. Some users may simply prefer that the totality of their exercise activities be prescribed, supervised, or monitored by a human trainer or other exercise specialist. Any number of other possibilities exist that may warrant human guidance of a user's exercise activities by a third party, all of which are envisioned herein. The automated system of this invention provides novel opportunities to incorporate the remote participation of a trainer into the user's exercise activities, thereby leading to additional business opportunities.

As described above, a user's exercise workouts and all other data obtained or stored by the automated system are preferably available to said user or designee upon demand. When a user desires to share such information with a third party trainer or other professional, the system may be configured to permit the user to authorize direct access to said user's data by the third party professional on his behalf as his designee using one or more networked communications resources of the automated system described elsewhere herein. Said third party designee may then review the user's data and advise the user as to the efficacy of the exercise workouts generated by the system, provide guidance to the user regarding the imposition of limits or other modifications to the generation of future workouts, or simply confirm that the user's activities are consistent with said third party professional's recommendations. When the third party professional deems that modification of the exercise workouts are warranted, said modifications are preferably communicated to the automated system via one or more user preferences disclosed in great detail elsewhere herein. Said user preferences are always evaluated by the system and accommodated whenever possible as a component of the one or more of the system's methods implemented by the workout generation engine. When the third party professional's recommendations rise to a higher level of concern, such as increasing the potential for injury, the user may provide information to the system categorized as potential injury limitations also disclosed in great detail elsewhere herein. As the automated system is configured to observe any and all constraints based on potential user injury, any such limitations imposed by third party professionals will always be incorporated in generated exercise workouts.

In one embodiment, recommendations of third party professionals are preferably supplied to the automated system by the user. In one embodiment, the third party professional may access the automated system using one or more networked communications resources described elsewhere herein and directly supply any and all exercise workout recommendations or limitations as user preferences or injury limitations on behalf of the user.

Third party professionals may utilize the features and advantages of the system in service of their existing clients and for recruitment of new clients, thereby providing a business model complementary to the relationship between the automated system operator and its users. In one embodiment, the automated system further comprises a database of fitness professionals available for hire by system users. If and when desired by a user, said database may be queried to obtain a list of professionals available based on availability, cost, experience, client evaluations/ratings, geographic location, particular fitness specialty, or any other criteria deemed useful or desirable. In one embodiment, they automated system is configured to permit the user to contact and potentially retain the services of one or more third party professionals using system resources described herein. In one embodiment, the user is provided with contact information and may contact and retain any third party professionals via communication means independent of the automated system.

When third party professionals are involved, a business relationship may be established between said professionals and the automated system operator. Depending on the business model established by the automated system operator, third party professionals may be included in said database upon request at no charge. In some embodiments, remuneration may be provided by professionals to the automated system operator for the privilege of being included in the database, based on clients obtained, consultation services provided, or revenue derived from the automated system, all of the above, or any of the above in combination with, or in lieu of, any other desired criteria. In one embodiment, the automated system operator may charge a fee to a user for consultation with a third party professional and remit a portion of that fee to the professional as compensation for his participation. In that case, the automated system operator will establish business relationships with both the user and the third party professional.

In another embodiment, a business relationship may be established between the user and the professional and the automated system configured to provide a payment mechanism to facilitate that relationship. For example, payment for services rendered by the professional to a user may be collected by the automated system which retains a processing fee and remits the balance to the professional.

In another embodiment, a first additional business relationship may be established between third party professionals and the automated system operator and a second additional business relationship established between the users and professionals. In some embodiments, all compensation from users to third party professionals is handled independently from the automated system. However, as disclosed elsewhere, these relationships are distinct from the relationship between the user and the system operator by virtue of the services provided by the various resources of the automated system and its components.

Any business model preferred by the automated system operator with respect to participation by third party professionals is envisioned by this disclosure without limitation.

It can thus be seen that the present systems can provide one or more of the problem solutions and advantages noted above. Further, the automated station and mobile application provide increased effectiveness, safety, functionality, and use of the exercise facilities in differing apartment complexes, hotels, exercise clubs, municipal facilities, corporate exercise rooms, or gymnasiums. With such systems, users need not wander around exercise facilities with no understanding of how to use equipment or how to develop an effective workout plan.

Other features can be included, and they will become apparent as this specification proceeds.

BRIEF DESCRIPTION OF THE DRAWINGS

The applicants' preferred and other embodiments are disclosed in association with the accompanying drawings. In the drawings, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 5 is an elevation view of the automated station of FIG. 4.

FIG. 6 is a front plan view of the automated station of FIG. 4.

FIG. 7 is a side plan view of the automated station of FIG. 4.

DETAILED DESCRIPTION OF SOME EMBODIMENTS OF THE INVENTION

Figure 1:
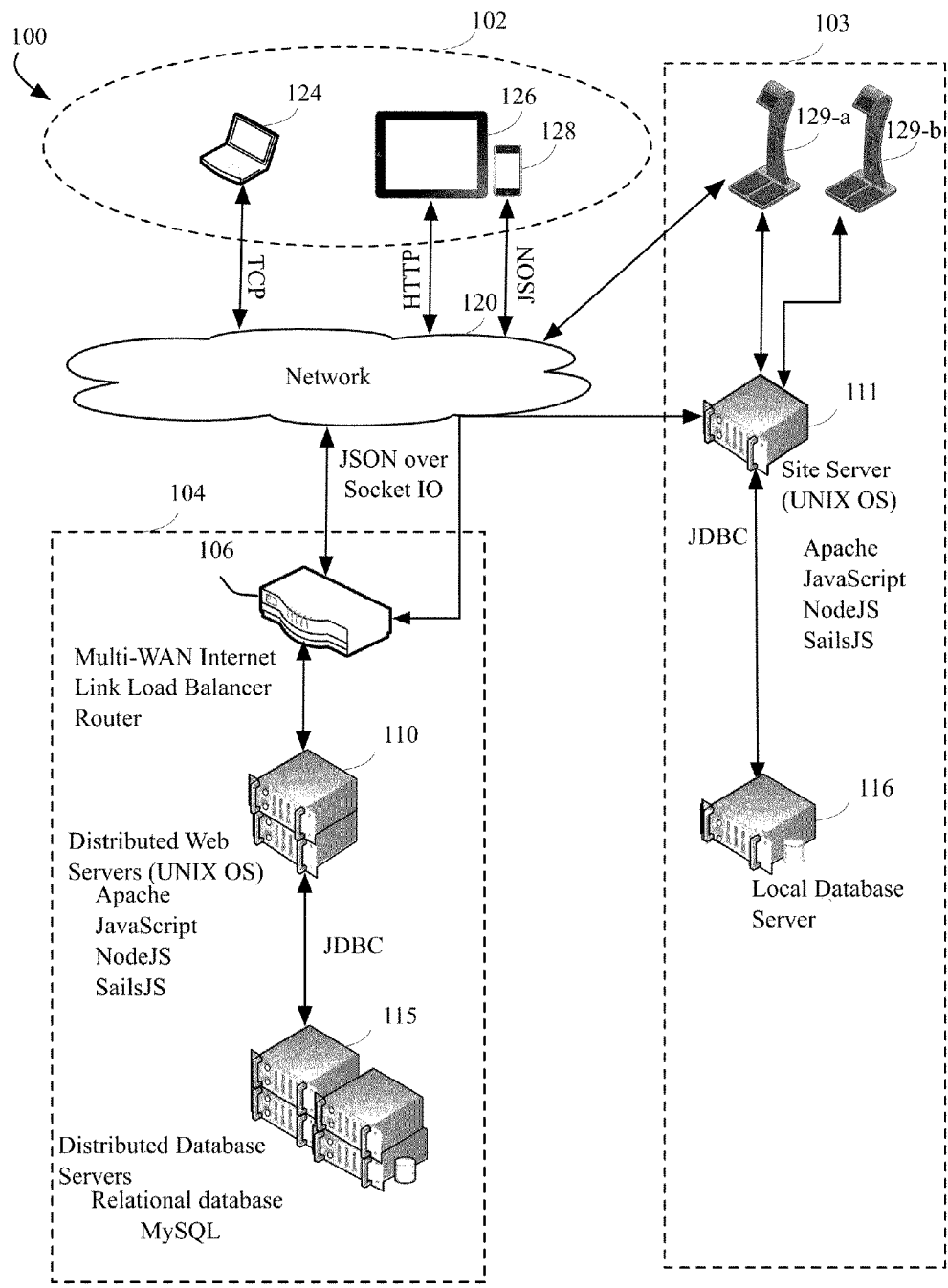
FIG. 1 is a computer network or similar digital processing environment in which an automated system can be implemented according to exemplary embodiments disclosed herein.

The following description provides examples and is not limiting of the scope of this application. Where examples are provided for illustrative purposes to more fully describe various aspects of one or more embodiments, such examples are merely representative and are never intended to limit the invention to that or highly similar examples. A person of ordinary skill in the art may immediately recognize, or may later appreciate, any number of additional examples or applications to which the present invention may apply. All such embodiments or applications are envisioned by this disclosure and are incorporated herein. Changes may be made in the function and arrangement of elements discussed without departing from the spirit and scope of the disclosure. Various embodiments may omit, substitute, add, and mix and match various procedures or components as appropriate or desired. For instance, the methods disclosed may be performed in an order different from that described and various steps may be added, omitted, or combined. Also, features disclosed with respect to certain embodiments may be combined in or with other embodiments as well as features of other embodiments.

Certain embodiments of the automated systems and methods are described with reference to methods, apparatus (systems), and computer program products that can be implemented by computer program instructions. These computer program instructions can be provided to a processor of a one or more computing devices, such as a general purpose computer, special purpose computer, mobile computing device, or other programmable data processing apparatus to produce a particular machine, such that the instructions, which execute via the processor of the computing device, implement the acts specified herein to transform data from a first state to a second state, transmit data from one computing device to another computing device, and generate physical state transitions at one or more geographic locations.

These computer program instructions can be stored in a computer-readable memory that can direct a computing device or other programmable data processing apparatus to operate in a particular manner, such that the instructions stored in the computer-readable memory produce an article of manufacture including instructions for implementing the acts specified herein. The computer program instructions may also be loaded onto a computing device or other programmable data processing apparatus to cause a series of operational steps to be performed on the computing device or other programmable apparatus to produce a computer-implemented process such that the instructions which execute on the computer or other programmable apparatus provide steps for implementing the acts specified herein.

The programming of the programmable apparatus creates a new machine, creating a special purpose computer once it is programmed that performs particular functions pursuant to instructions from program software. The automated systems can be described in terms of a dedicated circuit or a process that emulates that circuit. The software processes of the extended package collaboration system are, at least in part, interchangeable with a hardware circuit. This new machine can thus be implemented as a complex array of hardware circuits, programming that facilitates the unique functions of the extended package collaboration system, or both.

Various illustrative logical blocks, modules, and algorithm steps described in connection with the embodiments disclosed herein can be implemented as electronic hardware, computer software, or combinations of both. To illustrate this interchangeability of hardware and software, various illustrative components, blocks, modules, and steps have been described generally in terms of their functionality. Whether such functionality is implemented as hardware or software depends upon the particular application and design constraints imposed on the overall system. The described functionality can be implemented in varying ways for each particular application and function, but such implementation decisions should not be interpreted as causing a departure from the scope of the disclosure.

The various illustrative logical blocks and modules described in connection with the embodiments disclosed herein can be implemented or performed with a general purpose processor, a specific purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any conventional processor, controller, microcontroller, or state machine. A processor can also be implemented as a combination of computing devices such as, for example, a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a computer terminal. In the alternative, the processor and the storage medium can reside as discrete components in a computer terminal.

Depending on the embodiment, certain acts, events, or functions of any of the methods described herein can be performed in a different sequence, or can be added, merged, or left out altogether (e.g., not all described acts or events are necessary for the practice of the method). Moreover, in certain embodiments, acts or events can be performed concurrently such as, for example, through multi-threaded processing, interrupt processing, or multiple processors or processor cores, rather than sequentially. Moreover, in certain embodiments, acts or events can be performed on alternate tiers or on alternate components within the architecture.

In some embodiments, the system includes several components, such as, for example, a web application including a presentation layer in communication with a server-side logic layer, and a cloud-based database environment employing structured data, such as, for example, SQL defined data structures. In some implementations, one or more components are deployed on a Microsoft®, Linux®, or UNIX® operating system, such as, for example, Windows®, Ubuntu Linux®, or Mac OS X®. One or more languages can be use to implement the various components across the various architecture layers. Languages and frameworks can include, but are not limited to PHP, HTML, CSS, JavaScript, Ruby on Rails, Grails, and SQL.

Communication within systems may include standard web protocols such as, for example, HTTP/HTTPS via standard network protocols such as TCP/IP. Alternative web protocols for intra-system and Internetwork communication currently under development including HTTP version 2.0, HTTPS version 2.0, and SPDY are contemplated and within the scope of this disclosure. Successors to these protocols are also envisioned and are supported within the scope of this disclosure.

Referring now to FIG. 1, in some embodiments, a computer network or similar digital processing environment 100 supports implementation of the of the automated systems disclosed. Portions of the present systems and methods can also run on different architectures that include a LAN, WAN, stand-alone PC, stand-alone mobile device, one or more stand-alone, clustered, or networked mini or mainframe computers, etc. The automated systems can be distributed on multiple computers and devices 102, 103, 104.

FIG. 1 is representative of many specific computing arrangements that can support the automated systems and methods disclosed. In one embodiment, the software implementing the automated systems runs in the Linux® environment on an i686 architecture. In another embodiment, the software is implemented to run in other environments, such as Windows® or UNIX®, and to run on any hardware having enough power to support timely operation of software such as that identified in FIG. 1. In some implementations of the automated systems, a Linux® distribution, such as, for example, Ubuntu®, is deployed on one or more server computers 110, 111, 115, 116. In some embodiments, computers are deployed as virtual instances rather than physical computers.

In some instances, an automated station 129-*a*, 129-*b* is implemented, in part, as a combination of proprietary and off-the-shelf hardware and software. The hardware can include, for example, a standard Wi-Fi enabled Android tablet that is Android USB Accessory mode compatible. Custom hardware can include sensors configured to obtain various biological statistics, such as, for example, heart rate, body fat percentage, weight, and the like. In some implementations, the custom hardware also acts as the USB host in accordance with Android's Open Accessory Protocol. Software can include Android OS version 4.0.3, a custom Java-based Android application maintaining a SocketIO socket to the site-specific slave server 111 using an IP address and Port Number read from a config file stored on the Tablet's internal SD card, and a GUI using UnityPlayer.SendMessage method and a Unity-based graphical user interface application. In some instances, the user directly interacts with on screen elements through the Unity layer. This layer will receive messages from the Android application and then display the contents of the messages. When the user wants to perform an action that would result in data being updated, deleted, or created, the Unity layer collects the information for the change and sends it to the Android application, which then relays it to the site-specific slave server 111. In certain instances, the system can be integrated with off-the-shelf hardware and software services, such as obtaining, for example, weight and body fat percentages detected by a Fitbit Aria scale via a web services API accessing hosted Fitbit content.

A load balancing router 106, such as for example a Peplink® Multi Wan Router, can distribute traffic inside a firewall to and from distributed web servers 110. In some deployments, these webservers 110 are distributed instances of one or more application servers with distributions of Apache, a JavaScript runtime environment, Node.JS running SailsJS, along with supporting libraries such as those configured for communicating with persistent data stores, such as through a REST API. The distributed web servers 110 are communicatively coupled to computers 115 hosting one or more persistent data stores, file stores, or both. The data store can be distributed relational databases such as, for example, MySQL® 5.1.70, SQL Server®, or Oracle® storing primary and derivative data, or alternatively, can be relational databases in combinations with file stores that use native file systems. In an example, a distributed web server 110 may communicate with a distributed database server 115 via Java Database Connectivity (JDBC), Open Database Connectivity (ODBC), or other database communication protocol supported by the data store. In addition, or alternatively, the distributed database servers 115 may host XML databases, object oriented databases, NoSQL database, key-value caches and stores, and the like.

Client devices of various types 102 can connect to a remote server infrastructure 104 via a network 120 over one or more communication protocols. All computers can pass information as unstructured data, structured files, structured data streams such as, for example, XML, structured data objects such as, for example, JSON objects, and/or structured messages. Client devices 124, 126, 128 may communicate over various protocols such as, for example, UDP, TCP/IP, HTTPS and/or HTTP. In some cases, one or more client devices 124, 126, 128 may communicate via a wireless connection with the network 120.

Client computers and devices 124, 126, 128 and server computers 110, 115 provide processing, storage, and input/output devices executing application programs. Client devices 102 can also be linked through communications network 120 to other computing devices, including other client devices/processes 102 and server computers 110, 115. In some embodiments, server computers 115 host and execute software implementing centralized persistent data storage and retrieval. The network 120 can be a local area network and/or a wide area network that is part of a remote access network, a global network (e.g., the Internet), a worldwide collection of computers, and/or gateways that currently use respective protocols (TCP/IP, UDP, etc.) to communicate with one another.

Multiple client computer devices 102 can each execute and operate instances of the apps or applications accessing the automated system. In some embodiments, mobile apps provide the same functionality as applications running on the automated station excluding any hardware-related biological statistical information collection functions. The mobile app can also contain functionality locating exercise facilities based on the current location of the device running the mobile app, a selected location, or both. Additional functions can include the ability to edit a user profile, view past routines, view workouts, and track goal progress. In certain implementations an HTML browser interface is made available by one or more web servers, e.g., 110, for display on client devices 102.

On reading this disclosure, those of skill in the art will recognize that many of the components discussed as separate units may be combined into one unit and an individual unit may be split into several different units. Further, the various functions could be contained in one computer or distributed over several networked computers and/or devices. The identified components may be upgraded and replaced as associated technology improves and advances are made in computing technology.

In some embodiments, the automated systems are distributed across centralized master servers 110, 115 and site-specific slave servers 111, 116. The centralized master servers can store user profiles, as well as master copies of one or more database tables (see e.g., FIG. 3A through FIG. 3H). Site-specific slave servers 111, 116 can consist of a local implementation of some or all of the workout generation logic of the centralized master server 110. Automated stations 129-*a*, 129-*b* located at the specific site can access the site-specific slave server 111 to obtain information such as, for example, user profile data. In some instances, the site-specific slave server 111 generates workouts and modifies existing workouts locally without communicating with the centralized master server 110. The site-specific slave servers 116 may store complete copies, partial copies, or both of database tables thus reducing the amount of inbound and outbound data traffic. In some instances, some or all local database table copies are read only and are updated using a replication scheme, such as snapshot replication. Any changes originating at the site-specific slave servers 111, 116 or the automated stations 129-*a*, 129-*b* are either redirected to the centralized master servers with the site-specific local servers re-synced, or alternatively, are stored on the site-specific local server and later synced through a synchronization mechanism capable of resolving conflicts, such as database integrity conflicts.

Figure 2:
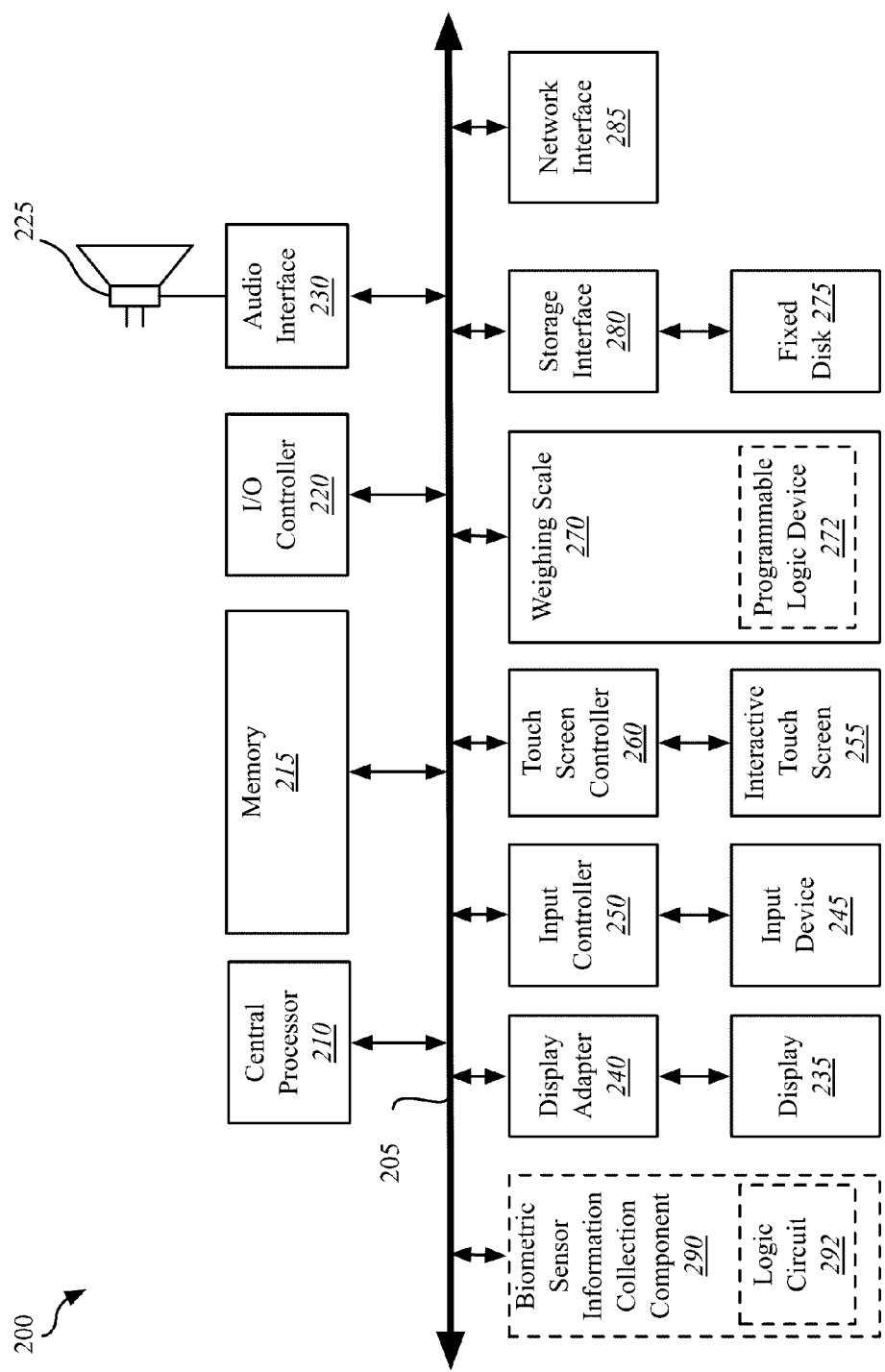
FIG. 2 is a schematic block diagram of one embodiment of an electronic configuration for one or more of the computing devices of FIG. 1.
Figure 3A:
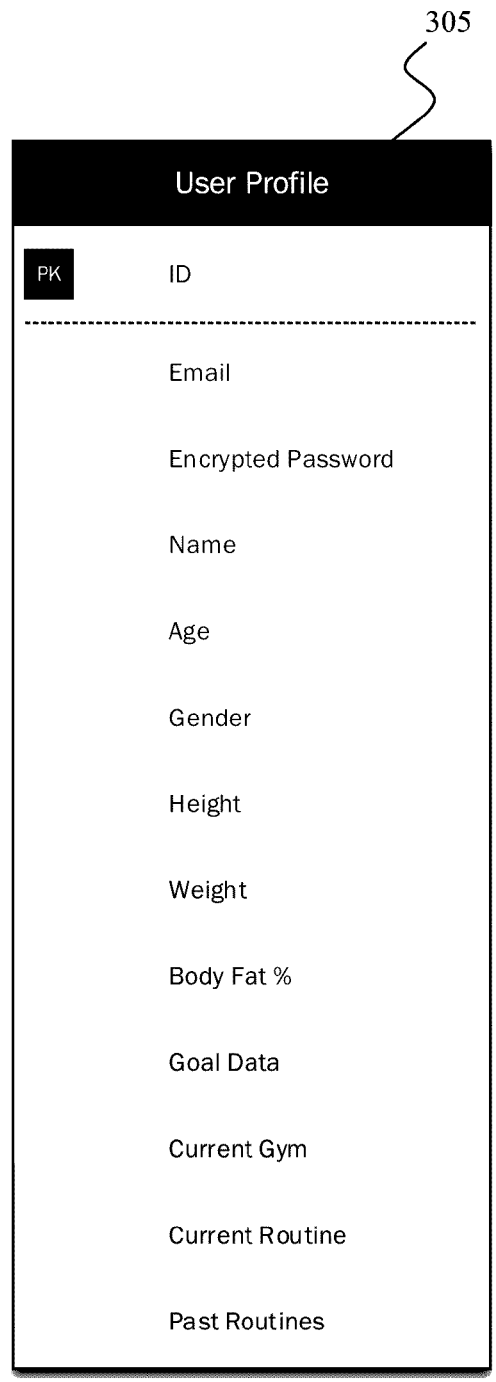
FIG. 3A through FIG. 3H are a series of diagrams of various tables stored in the relational database of FIG. 1.
Figure 3B:
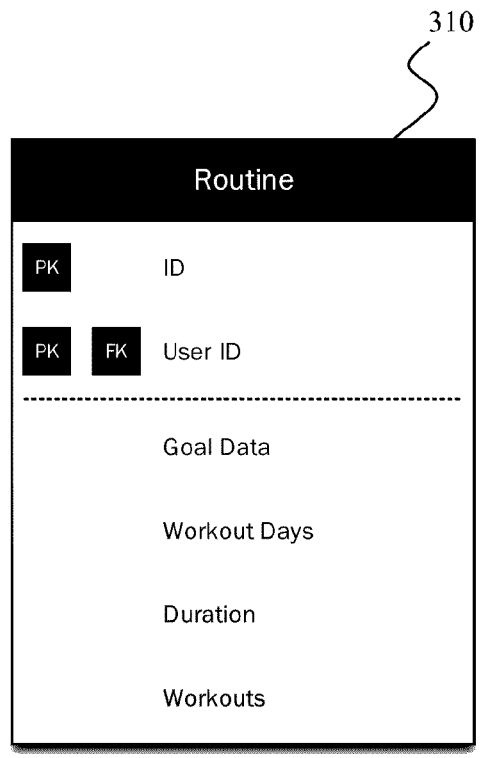
Figure 3C:
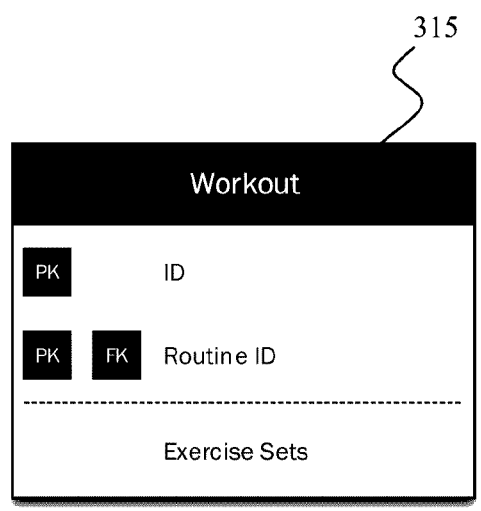
Figure 3D:
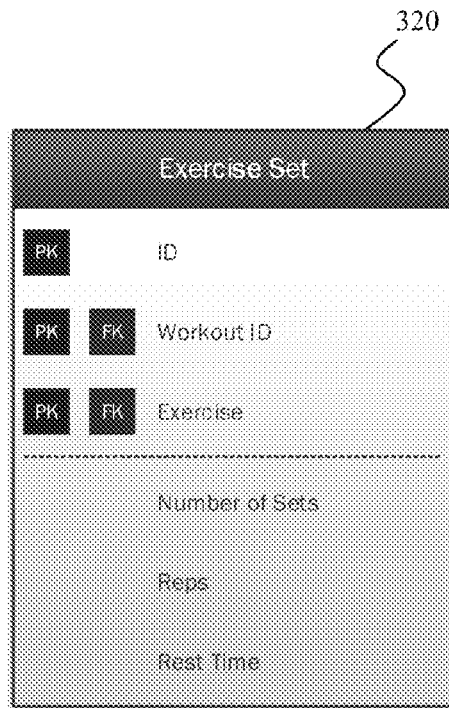
Figure 3E:
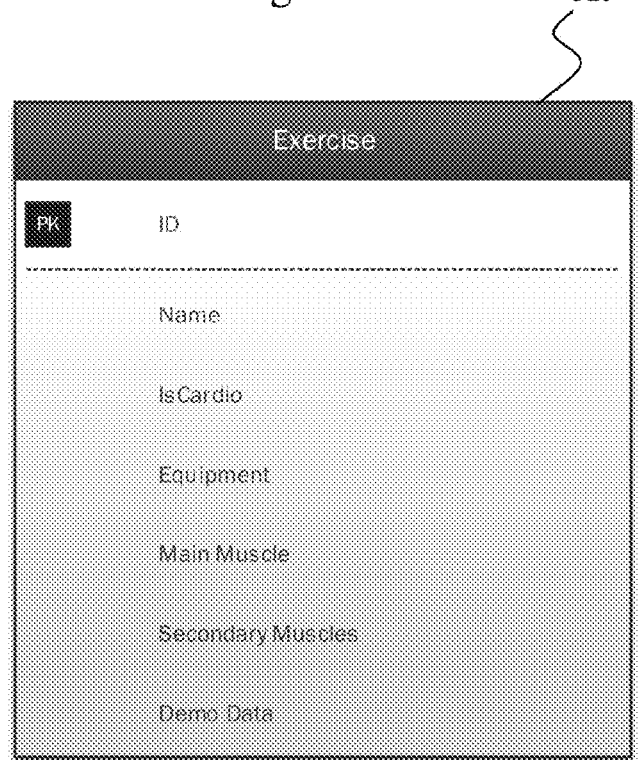
Figure 3F:
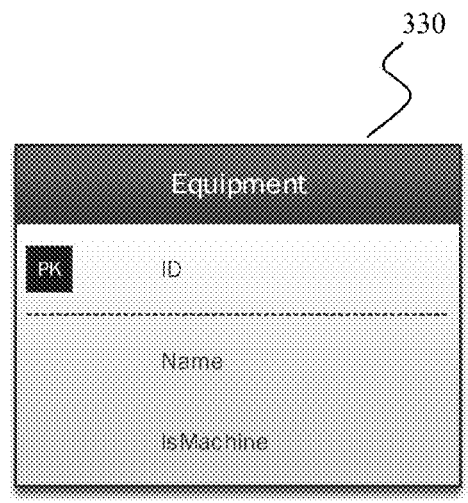
Figure 3G:
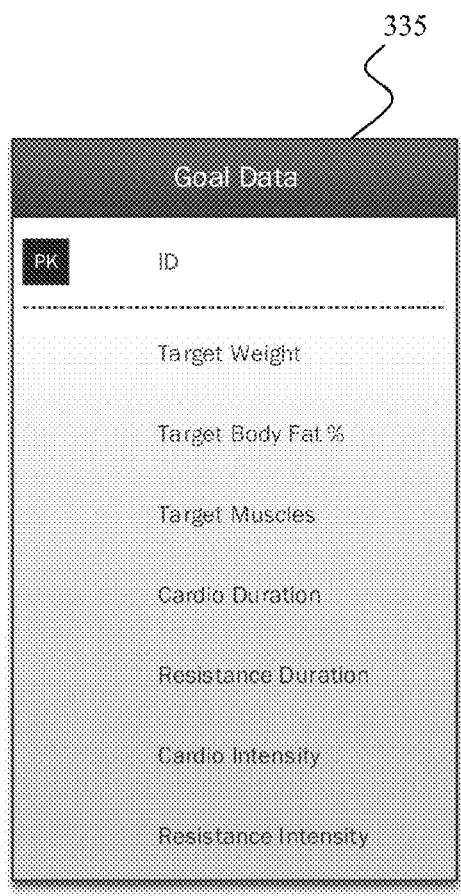
Figure 3H:
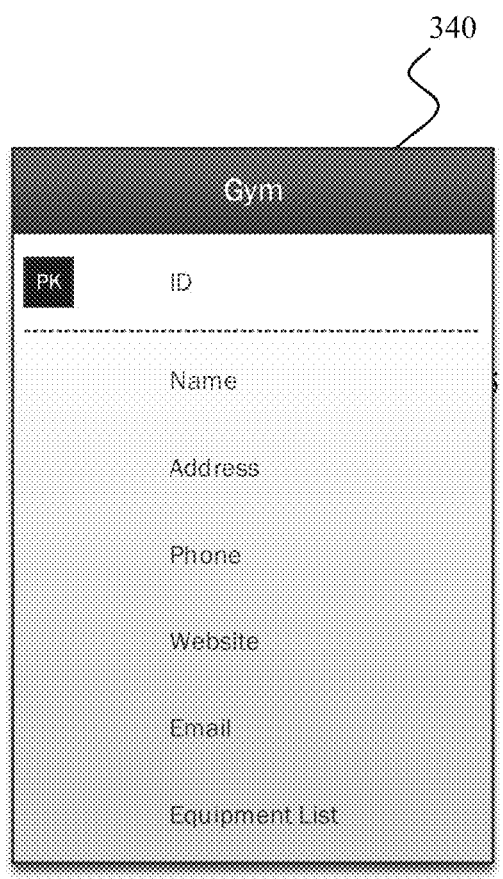
Figure 4:
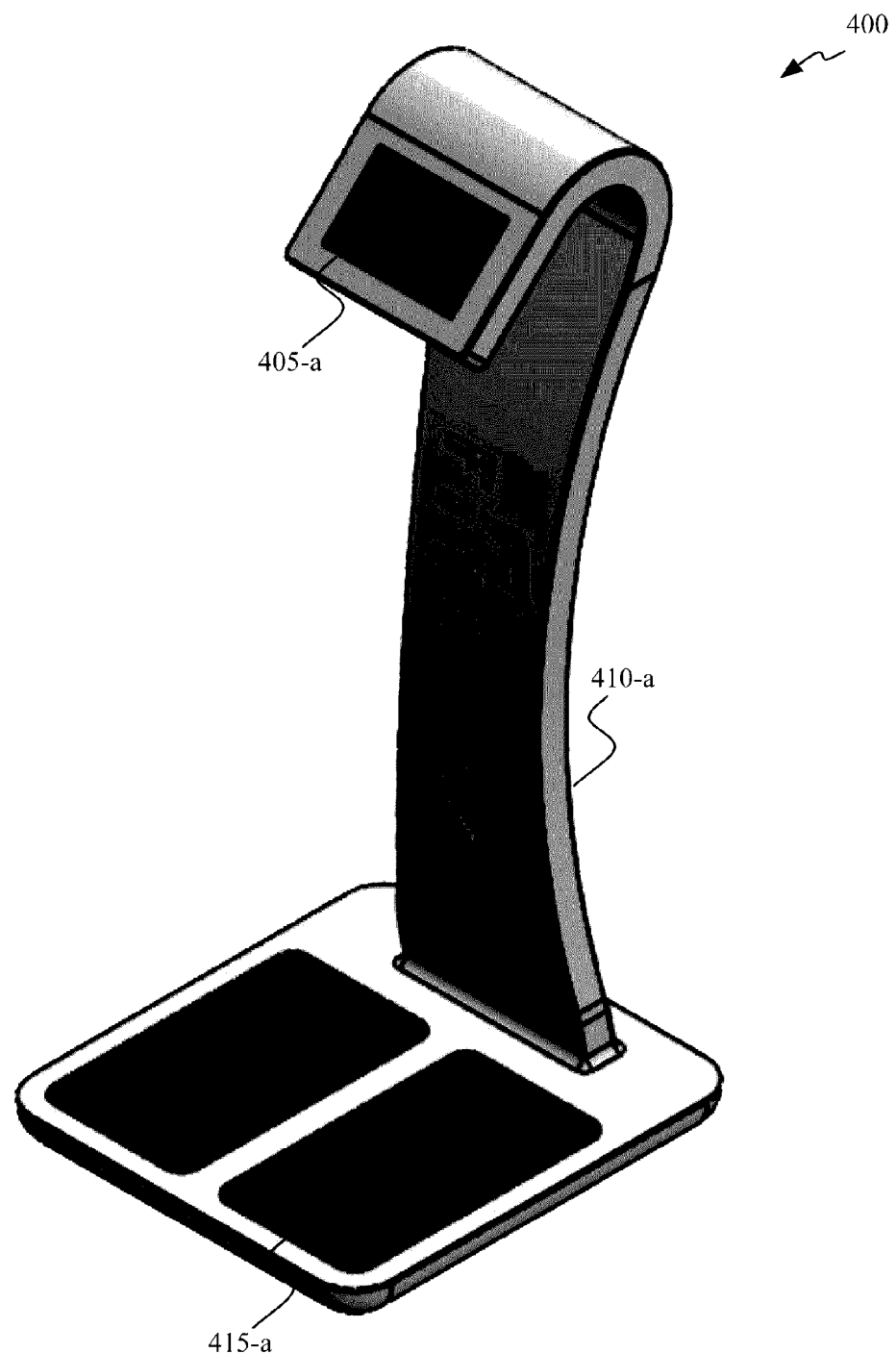
FIG. 4 is a perspective view of an automated station further described herein.
Figure 8:
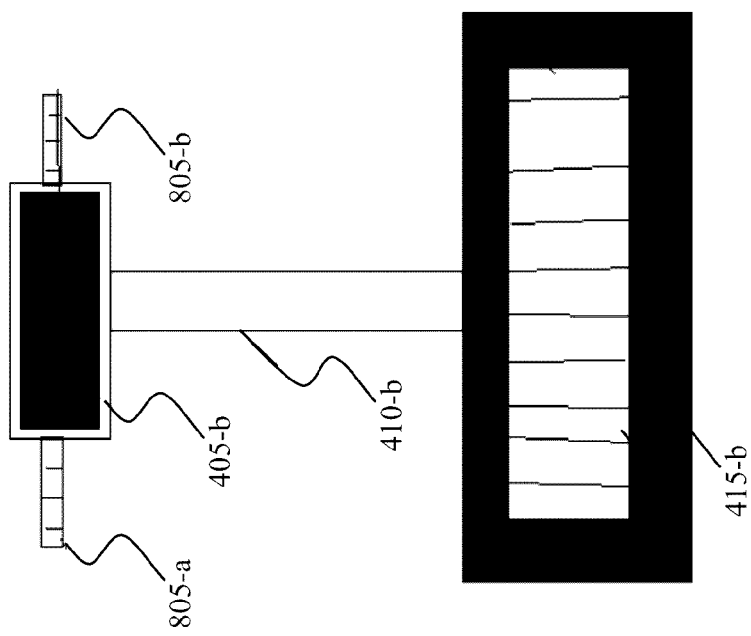
FIG. 8 is another front plan view of the automated station of FIG. 4.

Referring now to FIG. 2, device 200 is an example of one or more of the computing devices of FIG. 1. In one configuration, device 200 includes a bus 205 that interconnects major subsystems of the servers 110, 111, 115, 116 and client devices 102, such as a central processor 210, a memory 215 (typically RAM, but which may also include ROM, flash RAM, or the like), an input/output controller 220, an external audio device, such as a speaker system 225 via an audio output interface 230, an external device, such as a display screen 235 via display adapter 240, an input device 245 (e.g., a scanner interfaced with an input controller 250), an interactive touchscreen device 255 (coupled with a touchscreen controller 260), a weighing scale device 270 implementing an optional programmable logic device 272 (e.g., ASIC, FPGA or the like), an optional biometric sensor 290 implementing one or more logic circuits 292, and a storage interface 280 to a data store 275. Also included is a network interface 285 which can be coupled directly to bus 205.

In some embodiments, the interactive touchscreen 255 can include a touch-sensitive display overlay allowing player interaction with the images on the display 235. The touchscreen 255 and the touchscreen controller 260 can be connected to the display adapter 240. In certain instances, a user can make decisions and input selections into the device 200 by touching the touchscreen 255 at the appropriate places. The device 200 may further include multiple communication ports for enabling communication of the processor with external peripherals, such as external video sources, expansion buses, sensors, scanners or other displays, a SCSI port or a key pad. In some implementations, the device includes at least one weighing scale, implementing a programmable logic device 272, in communication with the central processor 210.

Bus 205 allows data communication between central processor 210 and system memory 215, which may include read-only memory (ROM) or flash memory (neither shown), and random access memory (RAM) (not shown), as previously noted. The RAM is generally the main memory into which the operating system, if any, and biosensing and automated workout generation system application programs are loaded. The ROM or flash memory may contain, among other code, the Basic Input-Output system (BIOS), which controls basic hardware operation such as the interaction with peripheral components 245, 290 or devices 270.

As with the other storage interfaces of device 200, storage interface 280 can connect to a standard computer readable medium, such as a fixed disk drive 275, for storage, retrieval of information, or both. The fixed disk 275 can be a part of device 200 or can be separate and accessed through other interface systems. Network interface 285 may provide a direct connection to a remote device via a direct network link. Network interface 285 may provide such connection using wireless techniques, including Wi-Fi, digital cellular telephone connection, digital satellite data connection, or the like.

Many other devices or subsystems (not shown) may be connected in a similar manner (e.g., displays, computing devices, keypads, cameras, authentication devices, and so on). Conversely, all of the devices shown in FIG. 2 need not be present to practice the present systems and methods. The devices and subsystems therefore may be interconnected in different ways from that shown in FIG. 2. The aspect of some operations of a system such as that shown in FIG. 2 are readily known in the art and are not discussed in detail in this application. Computer instructions to implement the present disclosure may be stored in a non-transitory computer-readable medium such as one or more of system memory 215 or data store 275.

Referring now to FIG. 3A through FIG. 3H, a series of database tables are provided supporting the various services and functions of the applications and devices of the several automated system embodiments. A User Profile table 305 contains user authentication and identification information. Goal Data, Current Gym, Current Routine, and Past Routines are referenced in corresponding tables.

The Routine table 310 defines a workout routine. It is associated with a specific user and contains a reference to the Goal Data used to create the workouts. Workout Days is an integer describing how many days out of a week the user will work out. Duration is the time in minutes for each workout. Workouts is a list of workout table references.

Workout table 315 describes the exercises for one workout day. It is associated with a routine by a Routine Table ID reference. Exercise Sets is a list of Exercise Set table entries.

The Exercise Set table 320 describes one exercise in a workout. The Workout ID associates an Exercise Set record to a single Workout record. The Exercise field references the exercise included in the Exercise Set. Number of Sets indicates how many "sets" to are to be completed as part of the workout. Reps indicates how many time to repeat the exercise for one set. Rest Time is the wait time between sets.

The Exercise table 325 describes an exercise. Name is the name of the exercise. IsCardio is a flag indicating if this is a cardio-based exercise. Equipment is a list of equipment associated with the exercise. Main Muscle is the name of the primary muscle that is used during this exercise. Secondary Muscles is a list of muscles other than the primary muscle used during the exercise. Demo Data is the location of the demonstrational videos or animation files if available.

The Equipment table 330 describes a piece of equipment in a gym. Name is the name of the equipment, and IsMachine is a flag used to indicate if this is free weight equipment or machine equipment.

Goal Data table 335 describes the data relating to a user's goals. Target Weight is the weight goal for a user. Target Body Fat % is the user's goal percentage for their body fat. Target Muscles are populated through processing goal question responses and lists of the muscles to be worked out during the routine. Cardio Duration is the duration in minutes for cardio exercises during a workout for the routine. Resistance Duration is the duration in minutes for the resistance exercises during a workout for the routine. Cardio Intensity is the intensity key for cardio exercises for this routine. Resistance Intensity is the intensity key for the resistance exercise for this routine.

The Gym table 340 describes the location, contact information, and equipment for a gym. The Equipment List references equipment from the Equipment table.

Referring now to FIG. 4 through FIG. 8, in some embodiments the automated station 400 includes a weighing scale 415-a or 415-b at the base of station 400, a support arm 410-a or 410-b extending upwardly from the base, and an interactive touchscreen 405-a or 405-b at an upper portion of the support arm. In some instances, the automated station also includes two electrical bioimpedance sensors 805-a and 805-b, sometimes referred to collectively as sensors 805, extending from the stand 410-b or touchscreen 405-b. In certain implementations, the sensors 805 are mounted in opposed handles extending laterally outwardly from opposed sides of the touchscreen 405-b. In certain embodiments (not shown) additional bioimpedance sensors may be provided on the lower portion of the automated station to permit contact with the a portion of a user's leg(s) or feet. When more than two sensors are provided, the system may be configured to use any combination of two or more of the sensors to obtain as many bioimpedance measurements as may be desired. In some embodiments, a voltage may be created between each pair of sensors one pair at time, with such voltage applied to each individual pair of sensors and the current flowing therebetween measured in a sequential manner. In other embodiments, a signal may be activated at a first sensor and the voltage difference and current flowing between said first sensor and all of the remaining sensors measured during the period when the signal at said first sensor is activate. This embodiment may provide for a more rapid measurement process but requires that the system apparatus performing the measurement, such as the automated station, either comprise more than one set of voltage and current measurement devices for simultaneous measurement at each sensor or that said device be configured to automatically switch at least one set of voltage and current measurement devices to measure those electrical parameters between each desired pair of sensors. For the reasons discussed elsewhere herein, it may be advantageous to measure the bioimpedance of a user's limbs independently in addition to the whole body bioimpedance of the user so that the pronounced contribution of limb bioimpedance may be used to adjust the whole body bioimpedance to more accurately characterize the muscle and fat content of the user's trunk where the preponderance of body fat is stored. Bioimpedance measurements of different portions of a user's body may be accomplished by choosing the locations at which the two or more biosensors are placed.

The automated station may include an internal computer having a microprocessor, digital memory and storage resources, the touchscreen display, and communications facilities such as an Ethernet port, a USB port, other ports if desired, and wireless Wi-Fi connectivity. These features may be used to provide any useful system function, including but not limited to receiving, processing, and communicating analog data from weighing scale 415-a or 415-b, analog data from biosensors 805 or any sensor devices providing equivalent functionality, or analog or digital data from any other source to other resources in the system or to the user.

As previously disclosed, use of the weighing scale 415-a or 415-b and biosensors 805 for data collection is preparatory to the generation of an exercise workout recommendation for a user. The automated station does not comprise any functionality for providing actual physical exercise to a user. Depending upon the specific embodiment, the automated station is merely an apparatus for the input of user data including measurements, the output of system-generated information, communication with other system components, and, in some cases, the performance of all or any portion of the exercise workout generation process. As such, the weighing scale and the biosensors are not deployed and active concurrently with the user's performance of the generated exercise workout. Such activities occur independently form the automated system without the communication of any data between the automated station, its sensors, and any other exercise-related apparatus.

In order for the automated system to generate a personalized workout, the user will provide certain initial information to the automated system and additional information will be collected from specialized custom hardware present in the system. Data preferably supplied by the user may include, but is not necessarily limited to a username, system password, e-mail address, name, age, height measurement, waist measurement, chest measurement, hip measurement, and sex. The user will also preferably input their body type (ectomorph, mesomorph or endomorph), often referred to as a somatotype, by selecting one of the three images that most closely matches their own body shape based on self-assessment. The user's body type may be correlated, with a relatively high degree of efficacy, to certain types of exercises known in the art to effectively address the physical fitness needs of that classification of users. Further, as described elsewhere herein, an accurate self-assessment of a user's somatotype enables a more accurate determination of whole body bioimpedance than has been previously known in the art.

In one embodiment, users will be prompted to provide information describing their present exercise workout activities, including but not limited to a self-assessment of their present physical condition, the number of times they exercise per month, and the extent of any other physical activity in which they engage on a regular or semi-regular basis. This information is important in the process of generating exercise workouts so that an appropriate regimen (neither too lax nor too rigorous) may be prescribed for the user, particularly at the beginning of their program.

In one embodiment, users will be prompted to provide information regarding any preferences, positive or negative, on the type(s) of exercise(s) or exercise resources (machines or devices) which the exercise workout generation method should favor or avoid, whenever possible. When a user has voluntarily and repeatedly engaged in certain activities, such as using a stationary bicycle, providing identical or similar exercises as component(s) of a system-generated exercise workout may be more familiar and enjoyable to that user. To the contrary, if a user has previously engaged in certain unenjoyable exercise activities, such as running, because it has been the only means of exercise know or available to that user, selecting treadmill exercises for that user would generally decrease the user's interest and make the exercise workouts less enjoyable than they might otherwise be. While each user's preferences are envisioned to be only one of many exercise workout generation input components for one or more embodiments of the present invention, incorporating exercise preferences of individual users can only serve to favorably customize the overall workout experience for each user.

In one embodiment, users will be prompted to provide information regarding any past or present injuries that may be relevant to certain type(s) of exercises to be preferred or avoided when an exercise workout is generated for said user. For example, a user with a history of shoulder injuries, particularly those requiring surgical repair, may not be a good candidate to perform exercise workouts comprising free weights due to the instability of free weights and the risk of potentially incurring sudden shear forces. For that particular user, a machine that imparts a stable resistance to the user would be less likely to aggravate or re-injure vulnerable areas of that user's body. Likewise, a user with a replaced hip or knee joint may not be a good candidate for treadmill activities where one or more lower impact exercise activities may be prescribed instead.

In one embodiment, the user may enter his or her specific goals, including but not limited to general fitness, a desired degree of weight loss, overall muscle building, development of a particular body region over another, or any hybrid combination of these or any other goals. As with the selection of individual exercises based on a user's preferences (positive or negative) as disclosed above, generating an exercise workout program for each user specifically directed toward said user's principal goal is preferable. Of course, there is a certain degree of unavoidable overlap between several of the exemplary goals presented above; increasing physical activity to build muscle is also very likely to lead to a certain degree of weight loss. However, a user primarily interested in losing weight may better achieve that goal by performing aerobic exercises that expend maximum energy and increase the user's heart rate than performing other exercises that repeatedly strengthen a limited muscle group. In other words, when a certain goal is preferred by a user, the combination of component exercises in a generated workout may be tailored to the greatest degree possible to direct the anticipated results toward the user's stated goals. In one embodiment, this focus may be particularly beneficial to certain users pursuing rehabilitation after injury or illness, where overall fitness and lower impact is greatly preferred over a more rigorous regimen of exercises better suited to an athlete in training.

With respect to information provided by each user, all such information will be stored in the user's profile and at least a portion of said information may be used to assess the physical condition of the user, to generate an exercise workout in one or more embodiments of this invention, or both. While providing certain information may be optional in certain embodiments, users will generally be encouraged to provide as much input as they are comfortable sharing in order to enable any particular embodiment of an exercise workout generation method to provide the most effective and enjoyable workout possible for each user.

The automated system may preferably collect certain biological parameters from the user, including but not limited to heart rate, body fat percentage, weight, and the like via at least one of weighing scale device 270 and biometric sensor 290. For example and without limitation, the user's weight may be collected by weighing scale device 270 and biometric sensor 290 may comprise two or more analog electrical impedance sensors 805 or any sensor devices providing equivalent functionality that may be used to determine body fat percentage and obtain any other relevant biological data within the extent of their measurement capability as discussed in greater detail below. These measured parameters will be stored as a part of the user's profile and be available to the automated system applications for use in generating a workout recommendation for the user.

In an embodiment where a user's goal(s) comprise reducing their weight or body fat to a certain level, measuring and persistently storing values of the user's weight and body fat over a period of weeks or months during which prescribed exercises are being performed are essential steps in ascertaining the user's progress toward their body fat or weight loss goals and for determining when those goals are ultimately realized. Lacking access to the user's history of biological parameters, the system will have no means of analyzing the user's progress or improving his results. As exercise workouts are generated by the system and then performed by a user on one or more separate machines or using other exercise resources, repeated measurement of a user's weight and body fat will provide indispensible feedback for future workout generation. Results of certain combinations of exercise components in an overall workout may be compared to the results of other combinations, subsequently compared to the trajectory of a user's measured weight and body fat, and when a particular combination of exercise components is found to have the greatest positive effect on either or both of the user's goals, said combination may be preferred for use in the generation of all future workouts.

This invention provides a significant advancement over the known art of bioimpedance measurements to facilitate attainment of fitness goals. Present art analog electrical bioimpedance measurement systems are directed toward determining an accurate value of body fat according to conventional understandings and definitions. That is, their focus is to provide a measurement result that may be directly compared with measurements obtained via other methods such as hydrostatic weighing. The measurements obtained by systems and methods described herein may also be correlated to those known in the art, but their primary utility is to permit the system to monitor, report to the user, and conform its generation of exercise workouts based on changes in said measurements over time. The specific value (s) of measurement data collected by the system and presented to the user are far less useful than the relative changes in said data over time, as the changes will reveal how the user's body is reacting to the exercise workouts being generated. When the sum total of the data available to the system over time reveals a lack of adequate positive response by the user (meaning that the user's physiology is not progressing toward the desired goals), the system is configured to modify the exercise workouts generated for the user to improve said response. Likewise, when available data reveals that certain exercise workouts yield the desired results, the system is configured to maintain the elements of said workout so that the user continues to progress toward his goals.

The measured analog bioimpedance data is one component of the sum total of all data available to the system but comprises a unique and novel role in this invention. Unlike with known systems and methods, correlating the data obtained via analog electrical devices to standards known in the industry via one or more approximation methods such as curve fitting and the like is unnecessary. The system is configured to compare the raw data obtained over the course of a user's participation, determine the nature of the user's progress, and adjust the exercise workouts it generates for maximum benefit to the user as described below. In this sense, the measured bioimpedance referred to herein may comprise any one or a series of more than one measurement (s) most useful for any particular user's purpose and does not refer to any standard that would conform to, or that may be correlated with, the same standards and results as obtained by hydrostatic weighing. For example, a user seeking rehabilitation from an upper body injury may only require bioimpedance measurements in the torso area, while a user seeking to lose weight may be primarily concerned with bioimpedance measurements in the waist and hip regions. Only those measurements pertinent to each user's goals are preferably collected and retained by the system.

In some users, and depending on the state of their physical conditioning and general health, a certain trend in measured bioimpedance coincident with improving conditioning or health may occur in other users where their health and conditioning are declining rather than improving. Due to the wide disparity in physiologies among the human population, one person's positive bioimpedance trend may be another's negative trend. However, simpler assessment criteria such as the user's weight, strength, and endurance may be easily determined and instantly interpreted to be good or bad. For example, a user seeking to lose weight and gain strength will immediately appreciate that a loss of three pounds and his ability to do ten more pushups over the past week is a positive result. However, that same user will not intuitively know whether an increase in the capacitive reactance component of his bioimpedance is good news or bad news. In some embodiments, the system may utilize the sum total of any progress criteria available to determine whether changes in a user's measured bioimpedance reflect a positive trend or a negative trend. By correlating the trend of the user's bioimpedance measurements all of the other data supplied to or collected by the system, the system will correlate the measured bioimpedance trend with said other data and thereby determine the preferred course for that user's bioimpedance measurements. This feature will be particularly useful when users reach the well-known "plateaus" in their weight loss or conditioning programs and their intuitively apparent rate of progress slows or stalls. If the system determines that the user's measured bioimpedance trend is still progressing in the desired direction, the exercise workouts it generates may generally maintain the same general characteristics. However, if the measured bioimpedance trend also indicates a change from the preciously-established positive track, the system will be configured to adjust the exercise workouts in a manner intended to place the user back on course to meet his stated goals. Likewise, a change in the measured bioimpedance trend while the user is continuing to progress according to the other intuitive metrics may portend a change in the user's physiology indicating the advisability for some modification to the forthcoming exercise workouts, perhaps thereby avoiding a "plateau" in the user's progress. In short, the collection, logging, and availability of a user's measured bioimpedance data during the course of said user's participation within the system, when correlated with all of the other system-measured and user-provided data, comprises yet another objective means for the system to track a user's progress and guide him to the most efficient attainment of his goals.

In some embodiments, scaling certain data to account for geometrical characteristics of a user's body may improve accuracy and provide a means to obtain certain targeted data measurements for one or more useful purposes. This form of data refinement should be distinguished from those intended only to provide a standardized result for comparison to the types of measurements obtained from different measurement apparatuses.

Figure 17:
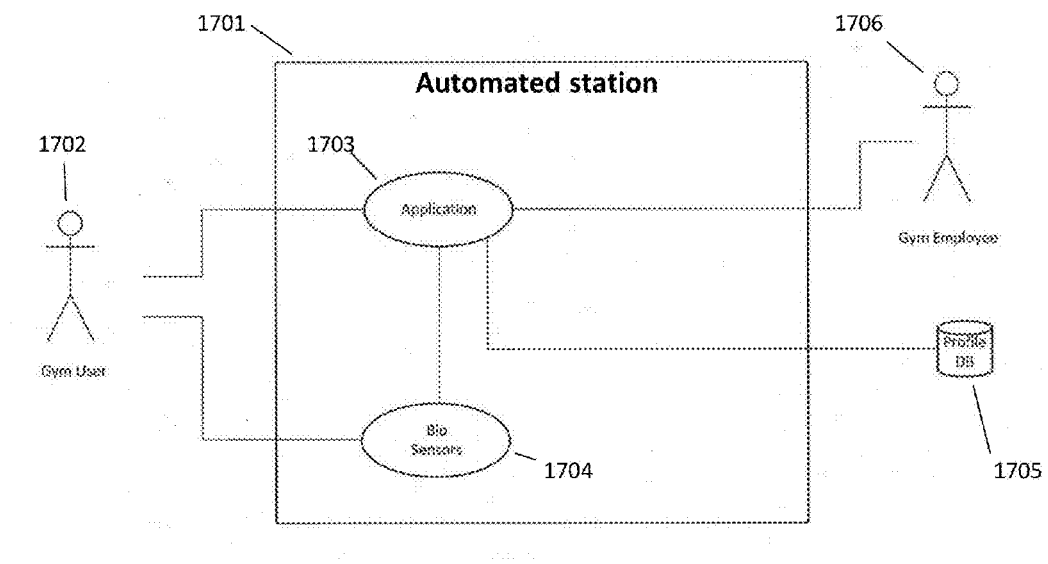
FIG. 17 depicts the interaction of certain devices or components operating within the computer network or similar digital processing environment of FIG. 1.

In some embodiments, biometric sensor 290 may be in data transfer communication with one or more of the computing devices 200 of the automated system and data there from be utilized by an application of the automated system to generate exercise recommendations for the user (see FIG. 17). Again, the digitization of bioimpedance data and its subsequent use in a computerized system does not diminish the fact that the original data was inherently analog at its inception and required specialized analog machines for its collection as previously disclosed.

In one or more embodiments, a user's body fat percentage is used to determine specific exercises along with factors including but not limited to their duration, intensity, and number of repetitions. Unlike the methods known in the prior art, the system of this invention is capable of performing comprehensive assessments of users' body composition by analyzing the measured bioimpedance in combination with the user's self-assessed somatotype to more accurately determine the user's body volume. Volume calculations are particularly important when a bioimpedance measurement is to be directed toward a specific region of a user's body. Proper volume determinations yield data most applicable to generating exercise workouts optimally directed to achieving the user's goals. In one embodiment, at least one of any of the user's height, hip measurement, waist measurement, or chest measurement may be used in any combination with the user's somatotype to further improve the accuracy of the volume calculation. With or without the added enhancements attributable to the use of somatotypes or other user data, in certain embodiments a bioimpedance measurement may be supplied to an exercise workout generation method as input for said method. For example, a user with a specified goal of building thoracic muscles but initially presenting a high body fat content will be better served by reducing his body fat content to a certain point before beginning a workout routine primarily directed toward his specified goal. In this case, the bioimpedance measurement will provide input to the exercise workout method not otherwise known to the system. As the bioimpedance measurements indicate that the user's measured body fat is declining in response to the workouts at least partially directed toward that system-determined goal, a greater portion of each generated workout may be directed to the user-specified goal(s).

In one embodiment, biometric sensor 290 comprising sensors 805 or any sensor devices providing equivalent functionality may be configured to perform a measurement of a user's bioimpedance using a single frequency. Typical bioimpedance measurement frequencies range from approximately 10 kHz to 1 MHz. The system may select a single frequency at which to measure the users' bioimpedance and persistently measure and store said data throughout the period of the user's association with the system.

As the human body is predominantly resistive and capacitive, the bioimpedance measurement will comprise components of resistance and capacitive reactance. The resistance of a bioimpedance measurement is known to be relatively constant when measured within the typical frequency range. However, the value of any reactive component of bioimpedance is known to vary as a function of the measurement frequency; for a constant value of capacitance, the measured capacitive reactance will decrease with increasing frequency of measurement as expected as would occur with any capacitance. However, the variety of tissues and their density, water content, and other composition will not necessarily present the same value of capacitance at all frequencies. Cellular structure and water content, in particular, exhibit frequency dependent characteristics. In one embodiment, a measurement frequency at the lower end of this range may be selected where the capacitive reactance is generally higher. In one embodiment, a measurement frequency at the higher end of this range may be selected where the capacitive reactance is lower. The system may be configured to select a single frequency anywhere within the typical range provided above at which the users' bioimpedance will be consistently measured and stored in the user's profile throughout the user's association with the system. As the user's physical condition changes as a result of the exercise workouts generated by the system and performed by the user, so do the measured resistance and reactance values of his bioimpedance, and those measured changes may be used to monitor the user's progress and as input for the exercise workout generation process.

In one embodiment, the system may be configured to determine the single frequency at which the users' bioimpedance comprises a certain measured value of resistance or reactance, and said values of measured resistance, measured reactance, and frequency of measurement may be stored in the user's profile throughout the user's association with the system. In this manner, the frequency of measurement will vary as the user's physical condition changes as the user performs exercise workouts generated by the system. As the measured resistance and reactance are only generally related but partially independent, either one may be used to determine the measurement frequency, but not both simultaneously. Values for all three parameters are preferably stored for each measurement and remain available for future reference. In this embodiment, the change in frequency, in lieu of a measured reactance and resistance, may be correlated to the change in the user's physical condition, including but not limited to weight, body fat content, hydration level, and the like.

In one embodiment, biometric sensor 290 comprising electrical impedance sensors 805 or any sensor devices providing equivalent functionality may be configured to perform measurements of a user's body fat using more than one frequency. Although measured capacitive reactance is inversely proportional to the frequency of measurement for any constant value of capacitance, and as introduced above, the cellular nature of the human body does not present the same capacitance to be measured at different frequencies. At the lower end of the typical frequency range, measurement current flows is generally unable to penetrate the capacitive cellular walls and therefore flows primarily in the extracellular spaces. At higher frequencies, where the cellular capacitive reactance is lower, measurement current flows through both intracellular and extracellular paths. For this reason, obtaining bioimpedance data at more than one frequency will provide additional data useful to track the physiological response by a user's body to the exercise workouts generated by the system and performed by the user.

In one embodiment, such measurement at more than one frequency may be performed iteratively, one discrete frequency at a time, for as many discrete frequencies as may be desired. In one embodiment, measurements may be performed using a continuous frequency sweep beginning and ending at discrete frequencies, with the frequency of measurement, resistive, ad reactive components sampled as frequently as desired during said sweep. The duration of the sweep measurement is dependent upon the total frequency range to be sampled, the desired or achievable frequency slew rate, the rate at which the voltage and current measurement machines are capable of sampling each parameter, and the total number of samples desired within the sweep duration, among other factors.

In one embodiment, an AC signal comprising one or more frequency components may be impressed between the two or more sensors. Observed in the frequency domain (amplitude vs. frequency), such signal would comprise a "comb" signal with each discrete frequency component appearing as a separate contribution to the total signal. Viewed in the time domain (amplitude vs. time), said signal may appear as a non-sinusoidal waveform such as, but not limited to, a ramp waveform, a triangle waveform, a square waveform, a sawtooth waveform, or any other non-sinusoidal periodic waveform. Each of such non-sinusoidal waveforms comprise more than one frequency component that, when all such components are combined, results in the non-sinusoidal waveform described by any periodic form such as the geometrically-similar shapes described above. The equivalence of time and frequency domain depictions of electronic signals via Fourier series construction and decomposition is a fundamental principle of electrical engineering and is extensively developed in the prior art. Such equivalence alone is not a novel feature of this disclosure; however, Applicant believes that its application of non-sinusoidal waveforms comprising multiple frequency measurement of bioimpedance (again, the ratio of voltage to current measured across at least a portion of a bioorganism) is novel in the known art.

In one embodiment, bioimpedance measurements may be obtained using a non-sinusoidal waveform as described above with a swept fundamental frequency, thereby providing a combination of multiple simultaneous frequencies each varying as function of time throughout the duration of the frequency sweep. For example, a square wave at a fundamental frequency is comprised of multiple components harmonically related to said fundamental frequency. As the fundamental frequency of the square wave is varied during a swept frequency measurement, the frequencies of each of the harmonics are varied by the same ration. That is, when the fundamental frequency is swept across a 10:1 range (say, from 1 MHz to 10 MHz), the frequency of each harmonic component is also swept across the identical 10:1 range so that the original square waveform is maintained.

In one embodiment, the voltage and current measurement devices are configured to obtain a broadband measurement such that the voltage and current measured between sensors simultaneously comprises contributions from every frequency component present in the original signal at each of their respective amplitudes. In one embodiment, the voltage and current measurement devices comprise frequency-selective filters and are thereby configured to measure the bioimpedance at only a subset of any multiple frequencies present in the AC signal generated by the system measurement apparatus and subsequently imposed between the sensors. Such filters may comprise high pass, low pass, band pass, or band reject filters as desired. The use of frequency-selective filters in bioimpedance measurements may be preferred with methods for user authentication via biodata measurement are employed, as the selection and measurement of a particular user's bioimpedance at a specific frequency, particularly one with a unique excessively high or excessively low value such as those occurring at or near either series or parallel resonance, may be easily distinguishable for authentication purposes.

With respect to this invention, it would be preferred that the bioimpedance measurement apparatus, such as the automated station, comprise a single AC generator configured to provide a non-sinusoidal waveform of the desired shape and amplitude comprising the multiple desired frequency components than for said apparatus to comprise a separate AC generator for each desired frequency component. However, both embodiments are envisioned by this disclosure.

In general, a total bioimpedance measurement duration time of between 3 seconds and 25 seconds is envisioned, with the preferred range lying between 5 and 15 seconds for any of the aforementioned embodiments.

In one embodiment, the bioimpedance measurement apparatus may further comprise one or more RLC (resistive-inductive-capacitive) network(s) in series, in parallel, or series/parallel connection with the sensors in communication with the user's body. Such networks may be used to transform the measured bioimpedance value (the ratio of voltage to current measured across at least a portion of a bioorganism) of the combined network of the user's body and RLC network(s) to a different range of measured bioimpedance values, typically by moving said value away from a point of resonance or toward a value where moderate changes in frequency yield a measurably significant change in measured impedance. If consistently deployed with identical RLC network configurations, this technique will still provide the same degree of observable change in the measured bioimpedance values necessary to provide the desired degree of monitoring capability disclosed above.

In one embodiment, the RLC networks may comprise components with controllable values of resistance, inductance, and capacitance, variable either physically or electronically, and said components may be adjusted to yield a certain measured value of bioresistance, bioreactance, or both when measured in combination with the user's body. As with the variable frequency embodiment described above, in this case the values of the components may be recorded and logged and used as the basis for determining the trend of the user's measured bioimpedance data. Components suitable for this purpose include, but are not limited to, the electronically variable inductor described in U.S. Pat. No. 7,889, 026 to Parsche, MEMS electronically variable capacitors such as those offered and sold by Cavendish Kinetics, digitally tunable capacitors offered and sold by Peregrine Semiconductor, segments of transmission line with open, short-circuited, or restively terminated ends that simulate RLC circuits, or any other known or later-developed technologies suitable for the intended purpose.

In one embodiment, a system comprising two or more biosensors configured to measure users' bioimpedance at more than one frequency may also provide secure biometric authentication in lieu of requiring a password, PIN, or other challenge/response method(s) requiring users to remember the required response. Similar to other authentication methods employing physical biometric data such as fingerprints, hand profiles, facial recognition, or retinal scans, the specific resistance and reactance of each user's body measured at multiple frequencies will provide data comprising a physical signature unique to that individual. However, unlike the aforementioned physical data which never changes (often referred to as "hard" biometric data, which is generally described as "something you are"), measured impedance data obtained from users is generally persistent but somewhat temporal, meaning that the data will be expected to change somewhat over time but is sufficiently stable over the short term. Rather than comprising "hard" data, the impedance data is better characterized as "firm" data. While some users decline to provide hard physical biometric data due to its everlasting persistence and their inability to recapture any lost privacy, measured bioimpedance data will become less and less useful over time unless the user continues to update the measured data known to the system by periodically authenticating using the previous measured data and permitting the system to replace the previous data with newer measured data. With respect to this system, where users' measured data is expected to change at a greater rate than that of the general population due to their exercise regimen, sufficient persistence of the previous measured data will permit successful authentication over periods of several weeks but possibly not longer than that. However, as the system re-measures and stores new bioimpedance each time the user is authenticated, replacement of the prior data with new data will provide more a sufficient period for subsequent authentication in the future before the most recent measured data becomes too outdated to identify the user.

In one embodiment, bioimpedance data may be augmented by the use of the user's weight as an additional identifying component for purposes of biometric authentication.

User authentication via biometric identification will provide improved security and convenience for users. Most importantly, as with hard biometric methods, it is impossible for all practical purposes for one user to impersonate another. Unlike with soft authentication methods (based on "something you know"), users will not be able to be able to share their authentication characteristics with other users as they can with a password or a PIN. In fact, users will not even know the raw bioimpedance data measured by the system, making it impossible for them to disclose it for the purpose of intentional replication. Rather than being required to remember and input a response to an authentication challenge (most commonly, "Password: ___"), under this embodiment users will be able to simply position themselves properly with respect to the two or more biosensors and the system will measure their bioimpedance and possibly their weight, authenticate the user using said measurement data, and then update the bioimpedance data in that user's profile to reflect the newly-measured values. While particularly useful for the exercise generation systems and methods disclosed herein, this feature is believed to be novel in the art and useful for any number of other authentication purposes as well.

Figure 9:
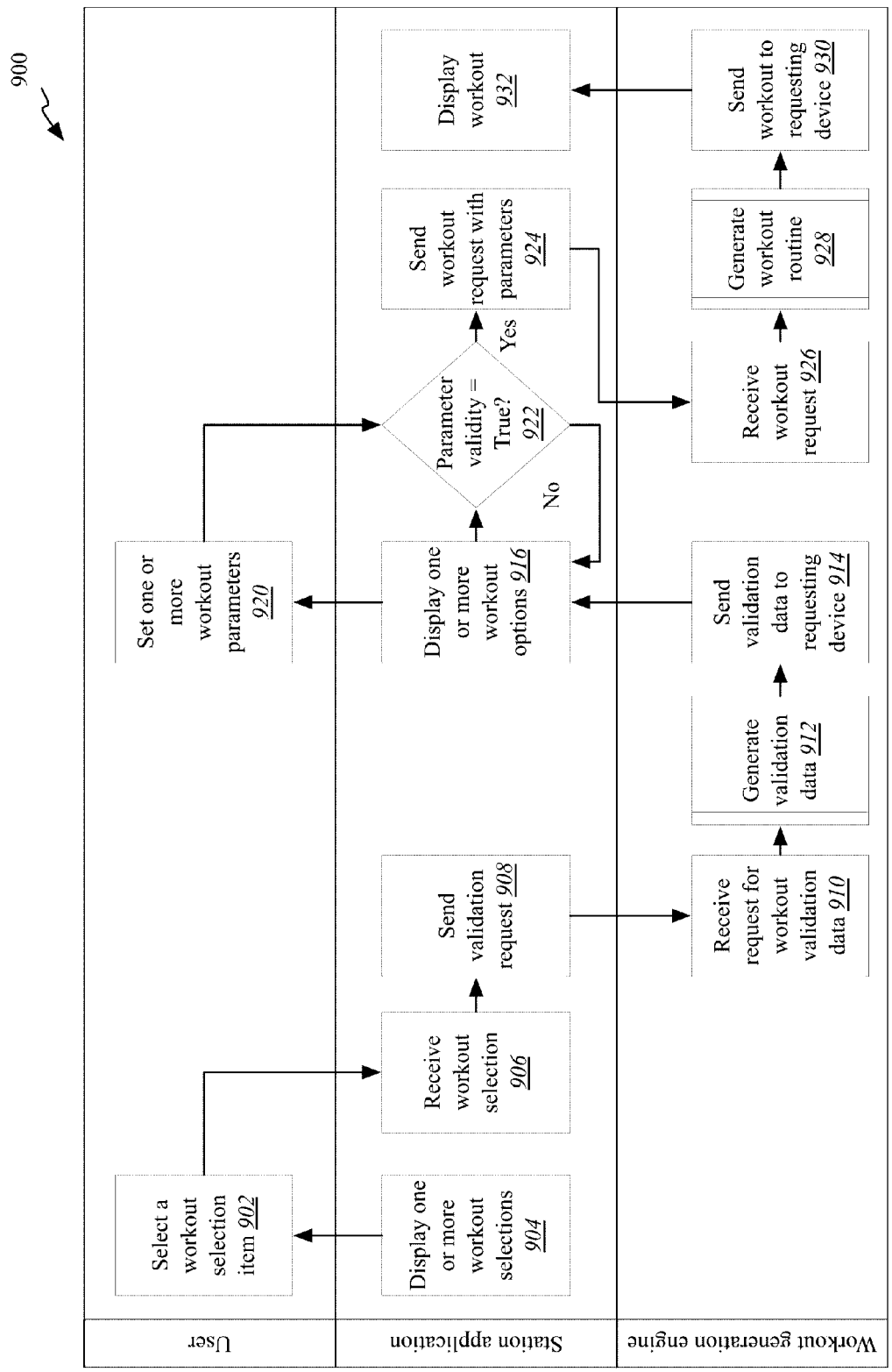
FIG. 9 is a flow diagram of a workout generation process performed by one or more components of FIG. 1.

Referring now to FIG. 9, an automated station application comprising a workout generation engine displays one or more workout selection items 904 such as, for example, a one-time workout selection item. Once the user selects a workout item 902, the automated station application sends the workout selection and a validation request to the workout generation engine 906, 908 requesting workout validation data for the current gym. Once the server receives the request 910, validation data is generated 912 and returned to the station application 914. The automated station application uses this data, at least in part, to generate one or more appropriate workout options 916. The user then sets one or more of the parameters represented by the workout options 920 to be submitted for the generation of a workout. These parameters can include, for example, the duration, a list of muscles to work out, and the workout intensity key. The automated station application then determines that there no erroneous parameters entered and that they are valid (for example, by using the duration to check the number of muscles that can be used for the duration against the number of muscles in the list and by checking to make sure the value for the Workout Intensity Key is one of the three possible values) 922. In the case of an invalid parameter, the user is prompted to make changes 916. Once all parameters are determined to be valid, the automated station application marshals the parameters into a JSON object where the key is the parameter name and the value is the selected value. The automated station application then sends a request to the server to generate a workout passing the JSON object as data 924. Upon receiving the request 926, the server executes a generate workout routine, generating the workout 928. The generated workout is then returned to the requesting automated station application as an array of JSON objects 930. Each JSON object in this array corresponds to a record in the Exercise Database with the data from the intensity table for the intensity key chosen appended. Once received, the automated station application then displays the workout 932.

In some embodiments, a JSON table indexed by the workout duration (for example, 30, 45, or 60 minutes) is returned as a table containing at least two values. These values can include an "ExerciseCount" such as the maximum number of exercise that can be generated for the selected duration and the "MuscleCount" such as the maximum number of muscles that can be exercised for the selected duration. The following is an example of a portion of the JSON object content for multiple durations:

```
{
    '30': {
        'ExerciseCount': 6,
        'MuscleCount': 3
    },
    '45': {
        'ExerciseCount': 8,
        'MuscleCount': 4
    },
    '60': {
        'ExerciseCount': 10,
        'MuscleCount': 5
    }
}
```

In some instances, a JSON object is provided including enumerated data types including, for example, "Strength", "MuscleMass" and "Endurance". These values can be used to access data from a workout intensity table stored and communicating in, for example, a JSON object. This object can include, for example, the number of repetitions per exercise set, the number exercise sets per workout, the rest periods between sets, and the like. The following is an example of a portion of the JSON object content for workout intensity JSON object:

```
{
    'Strength': {
        'reps': 8,
```

```
    'sets': 3,
    'restBetweenSets': 60
},
'MuscleMass': {
    'reps': 10,
    'sets': 3,
    'restBetweenSets': 45
},
'Endurance': {
    'reps': 12,
    'sets': 3,
    'restBetweenSets': 30
    }
}
```

In some instances, a JSON object is provided including, for example, data for use by the workout generator for the creation of one or more workouts. The following is an example of a portion of the JSON object content for a workout JSON object:

```
{
'Duration': 30,
'Muscles': [Chest, Abs, Biceps, . . . ],
'Intensity': 'Endurance'
}
```

Figure 10:
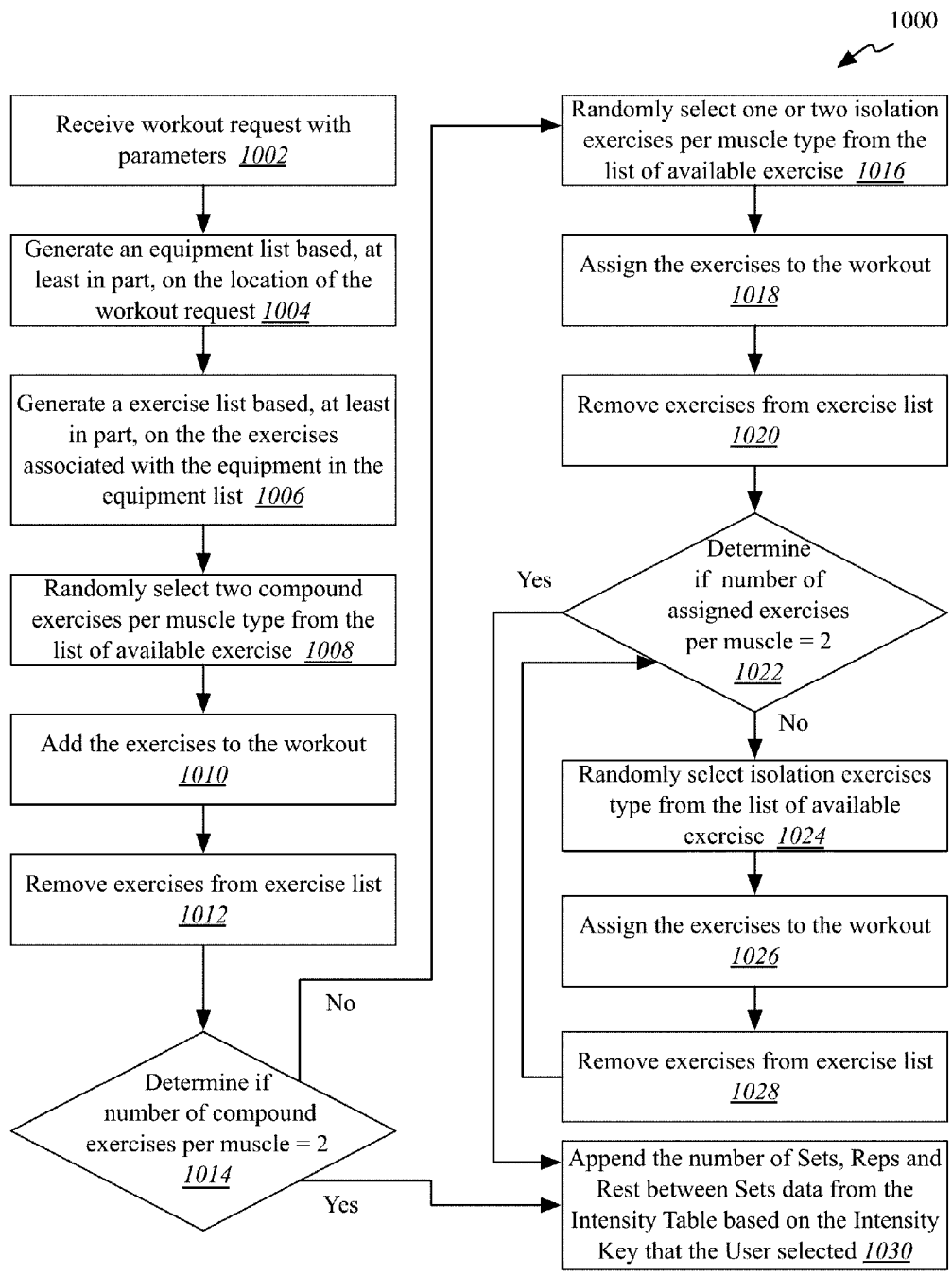
FIG. 10 is a flow diagram of a workout generation algorithm for generating workout routines in the workout generation process of FIG. 9.

Referring now to FIG. 10, a workout generation algorithm generates a workout based on parameters from the user. Once the workout generation engine comprising the workout generation algorithm receives the workout parameters 1002, it will generate an equipment list via said algorithm. In some instances, the generation of this list involves identification of equipment associated with a particular location 1004 using at least one of the one or more databases comprising information on available exercise resources and their location. The location of the user, either at an automated station or using a mobile device, is obtained by the workout generation engine and used to query said one or more databases for exercise resources within a defined radius from the query location. Exercises associated with the exercise resources retrieved from the equipment list are also obtained from the one or more database(s) and an exercise list is created 1006. Based on the desired duration of the exercise workout and other parameters supplied by the user, an appropriate number of exercise slots are created to be filled with specific exercises according to one of several embodiments, including those described below.

In one embodiment, two compound exercises are randomly selected added to the workout for each muscle identified in the workout data 1008, 1110. Compound exercises are those which simultaneously utilize more than one major muscle group and therefore burn more calories than do isolation exercises which utilize only a single muscle group. Once successfully added to the workout, the exercise is removed from the exercise list 1012. If a muscle does not have two compound exercises assigned 1014, the workout generation engine comprising the workout generation algorithm randomly selects either one or two isolation exercise(s) for the missing compound exercise(s) for that muscle 1016 and assign the exercises to the workout 1018. Once successfully added to the workout, the exercise is removed from the exercise list 1012. If there are still exercise slots open 1022, for each open slot the workout generation engine comprising the workout generation algorithm randomly selects a muscle and then randomly selects an isolation exercise for that muscle from the list of available exercises 1024. The exercise is assigned to the workout 1026, and once successfully added, the exercise is removed from the exercise list 1028.

In one embodiment, two exercises are selected for each muscle based on information obtained from the user's profile, such information including but not limited to the user's age, weight, height, measured bioimpedance data, somatotype, self-assessment of physical condition, history of physical activity, most or least preferred exercises or exercise resources, and the like. When such information may be used to distinguish one of the exercises from list of available exercises 1024 from another, the preferred exercise will be selected, added to the workout, and removed from the exercise list 1012. As above, muscles without two compound exercises assigned are assigned either one or two isolation exercise for the missing compound exercise(s) based on information from the user's profile and those exercises are also assigned to the workout.

In some instances, one or more exercises may be deemed suitable for more than one muscle. An important feature of the system and methods described herein is that the same exercise will not inadvertently prescribed more than once in a given workout for the purpose of exercising more than one muscle. By removing the exercise from the exercise list 1012 once it has been selected for a particular workout, it will not be selected again for that same workout.

Another highly desirable feature in exercise workout generation is that individual muscles are exercised in an order that provides complementary exercise and rest periods. An important component of proper exercise procedure is that sufficient time is afforded for muscles to sufficiently recover between periods of intense workout. For this reason, the workout generation engine arranges the order of exercises within each exercise workout to afford sufficient time for recovery of each significant muscle before that particular muscle is targeted for a subsequent exercise. Not doing so risks excessive fatigue, and even injury, to the user. However, an additional component of a maximally beneficial exercise workout that the user's heart rate and respiration be maintained at a properly elevated rate, so excessive rest between individual exercise components may reduce the effectiveness of the workout. The workout generation engine is configured to provide the optimal balance of sustained activity while simultaneously providing proper recovery time between exercise activity focused on a particular muscle.

An additional consideration is that most users have limited time in which to complete their workouts, so each workout should be composed in a manner that simultaneously provides the proper amount of targeted physical activity within the allotted time, allows appropriate rest for individual muscles between focused activity, and permits constant physical activity to maintain heart rate and respiration at the desired level. The exercise workout generation methods of this system are configured to provide exercise workouts consistent with all of these criteria.

Once all exercise slots are filled in the previous embodiments, the workout generation engine comprising the workout generation algorithm then calculates and appends the number of sets, repetitions, and rest between sets to each of the exercises in the workout based upon the intensity table and the intensity key selected by the user. In another embodiment, data from the user's profile relating to present physical condition, prior physical activity, injury, and the like may be used in combination with the user's selected intensity in determining the number of sets, repetitions, and rest between sets. For example, a user may select a more rigorous workout intensity than would be most beneficial given certain information in his user profile. In that instance, the system may provide an exercise workout that is at or near the higher limit of the appropriate range determined by the profile information but not beyond that. Similarly, a user may select a lower intensity than usual, so the system will consider his previous workouts and provide a workout on that day that is closer to the lower end of an acceptable intensity. An important advantage of the invention described herein lies in its ability to provide appropriate guidance based on best practices in exercise generation similar to that available from a human personal trainer. As taught in the present art, system that permit users to prescribe their own workouts introduce the probability of both exercise imbalance and injury to users not sufficiently knowledgeable in the science of physiology and fitness. Providing less than sufficient exercise in every workout would be a disservice to users. However, preventing a user from overexertion and injury is arguably the most important aspect of professional exercise workout generation, and the methods disclosed herein are specifically directed toward providing that same level of professional guidance in determining an appropriate level of intensity based on all available factors. A self-prescribed workout based on the "work till it hurts" is a recipe for disaster.

Figure 11:
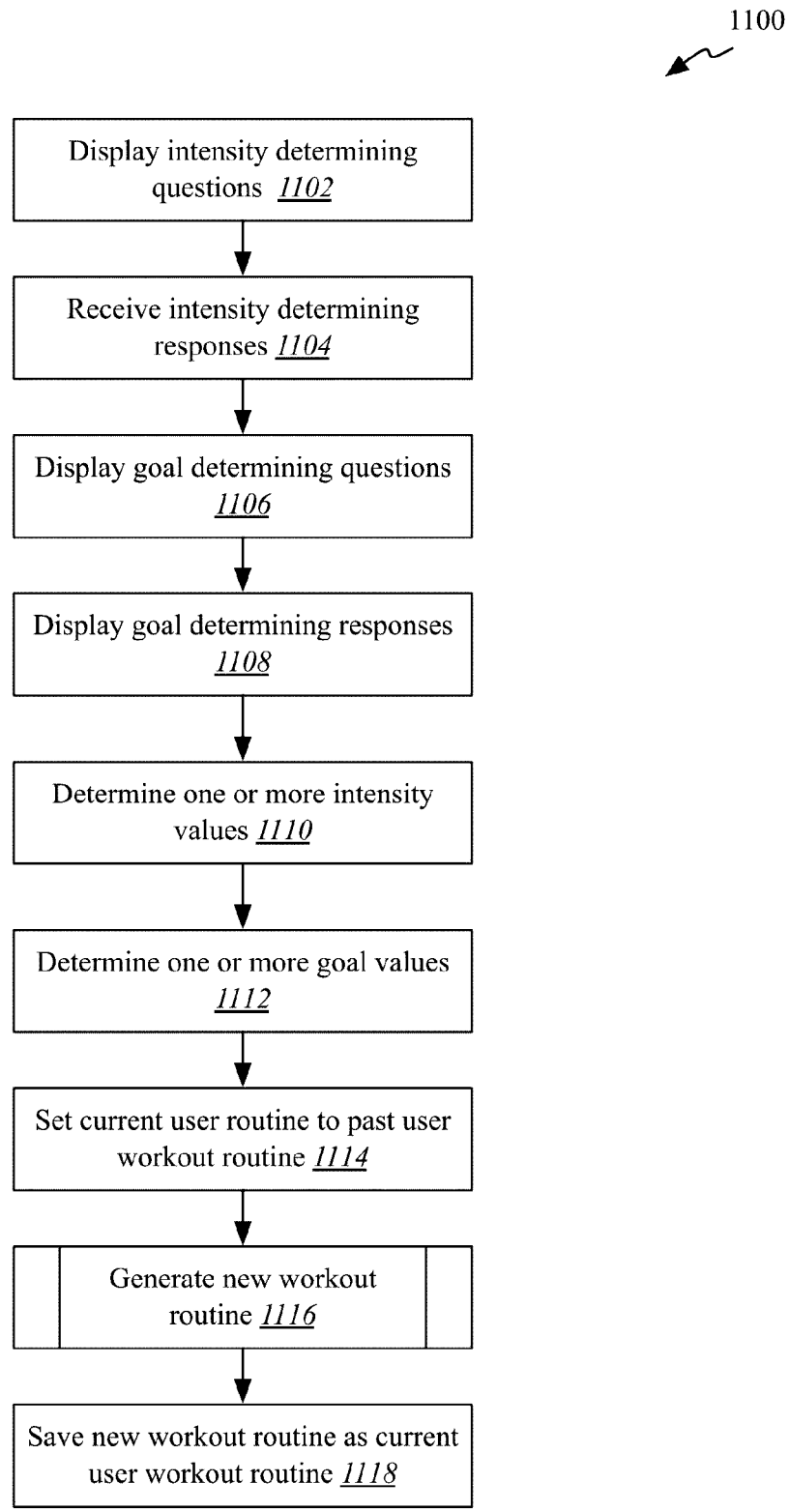
FIG. 11 is a flow diagram of a goal-based workout generation process performed by one or more components of FIG. 1.

Referring now to FIG. 11, in some embodiments, a goal based workout generation process 1100 implemented by the workout generation engine comprising the workout generation algorithm generates a workout based on goals set by the user. Initial intensity determining questions are displayed on the station application 1102. Once responses to the intensity questions are received 1104, one or more goal determining questions are displayed 1106. Responses are received by the station application 1108, and one or more intensity values, goal values, or both are determined 1110, 1112. In some instances, these questions are presented in a different order or simultaneously. The current user routine is then set to past user workout routine 1114 and a new goal-based workout is generated 1116. This workout, once generated, is saved as the current user workout routine 1118.

This goal-based workout generation process can, in some implementations, initiate at the creation of a profile or editing of user goals. In some instances, the automated station application displays a set of questions designed to determine the correct intensity for a user. These questions can be from a fixed set of questions stored in the client app, retrieved from a server, or both, and result in determination of an intensity key, the duration for each workout, and how many days in a 7 day work week will be regarded as workout days. The automated station application may then guide the user though a set of question to determine the user's goals.

In some embodiments, the goal questions are arranged in a tree-like data structure in which the leaf nodes contain the list of muscles to work out and two flags indicating if cardio exercises are to be added and if cardio exercises are added every workout or consolidated into one day. This tree is traversed using a depth first search that terminates on at the first leaf node encountered. The answers to the questions can dictate which child branch is executed. The goal and intensity data are saved in the user's profile, resulting in the current routine being saved as a past routine and replaced with a new routine. The goal-based workout generation process is then executed for the new routine using at least the goal and intensity data as inputs.

Figure 12A:
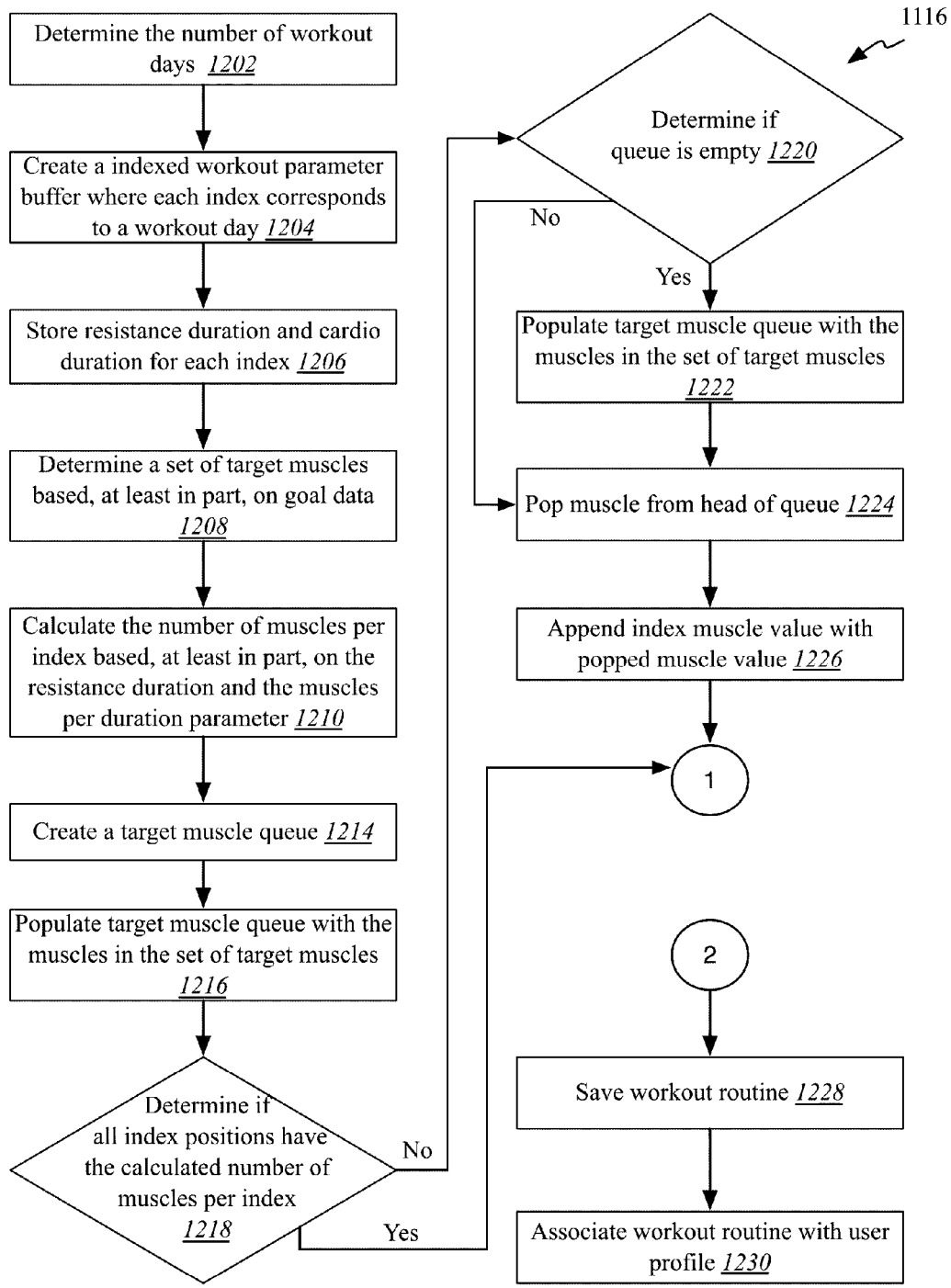
FIG. 12A and FIG. 12B comprise a flow diagram of a workout generation algorithm for generating workout routines in the goal-based workout generation process of FIG. 11.
Figure 12B:
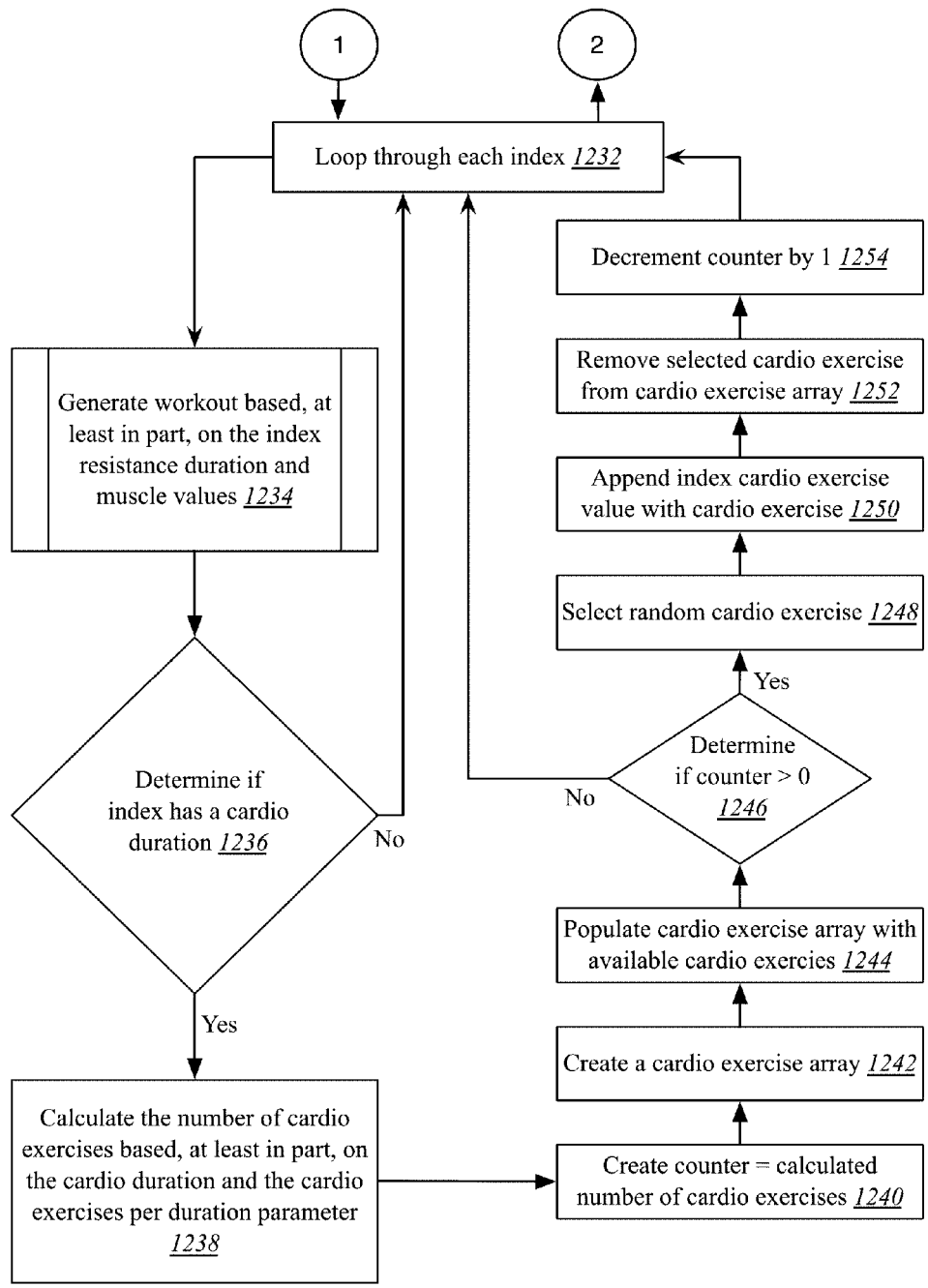

Referring now to FIG. 12A and FIG. 12B, the workout generation engine comprising the workout generation algorithm generates a workout based on a set of goals. The workout generation engine comprising the workout generation algorithm first determines the number of workout days 1202, then creates an indexed workout parameter buffer to hold the workout data 1204. The size of the buffer will correspond to the number of days to workout. Each index corresponds to one workout day. The data in each index of this buffer can include the resistance duration, cardio duration, and a list of muscles to workout 1206. The list of target muscles can be determined, at least in part, from the user goal data 1208. The target muscles from the goal data are split out over the set of days based, at least in part, on the resistance duration and the muscles per duration parameter of the workout validation data 1210. As an example, if the resistance duration is 30 minutes and the validation data says that the total number of muscles for a 30 minute workout is three, then three muscles are added to each day.

The workout generation engine comprising the workout generation algorithm creates a target muscle queue 1214, then populates the queue by copying the target muscle items in the target muscle list to the queue. A determination is made as to whether each index in the buffer has the correct number of muscle assignments per index 1218. If the determination returns false, the muscle queue is checked to ensure it has contains at least one muscle item 1220, and the muscle item at the head of the queue is dequeued 1224 and appended to the list of muscles for the index 1226. In the event the queue is empty, it is repopulated 1222 prior to initiating a dequeue event.

Once all index positions are properly assigned target muscles, each index is looped through 1232 in order to correctly populate the indexes with exercises. A workout is generated in accordance with the method 1000 of FIG. 10. For each index, a determination is made whether a cardio duration is set 1236. If so, the workout generation engine comprising the workout generation algorithm will select a random cardio exercise 1248. The random selection process can involve the creation of a cardio exercise array 1242 populated with the cardio exercises 1244 and a counter corresponding to the number array positions 1240, through which the number of positions is calculated, at least in part, by assessing the cardio duration and the cardio exercises per duration parameter 1238. So long as the counter is not empty 1246, the random cardio exercise is selected 1248 and the cardio exercise value for the index is appended with the selected cardio exercise 1250. Once the appending is successful, the cardio exercise is removed from the array 1252 and the counter is decremented by one 1254. In some embodiments, duplicate cardio exercises are not appended to a single day index position. After exercise assignments are complete for all days, the workout routine is saved 1228 and associated with the user profile 1230.

Figure 13:
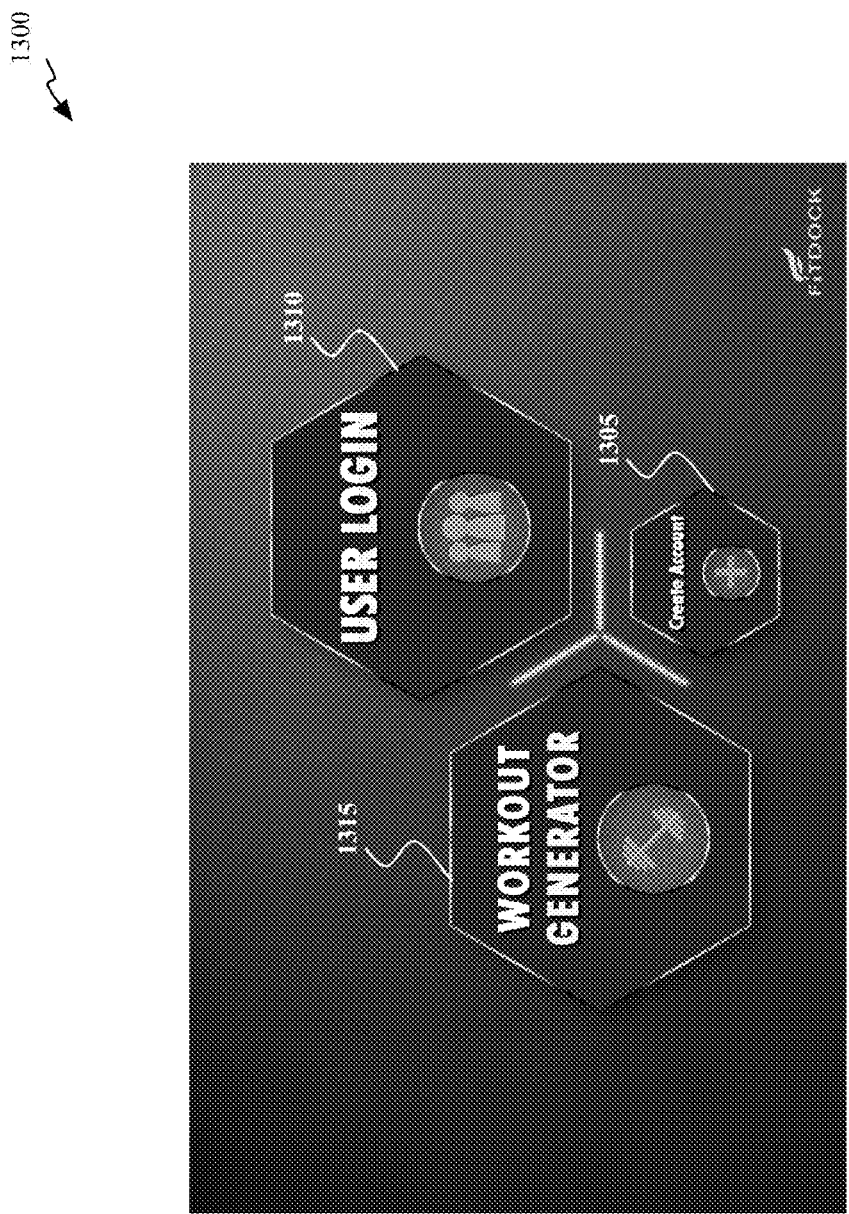
FIG. 13 is a screen capture of the introductory view displayed by the interactive touchscreen of the automated station of FIG. 4.

Referring now to FIG. 13, an introductory view is displayed on the station display where a user can create an account by selecting the create account button 1305, login to an existing account by selecting the user login button 1310, or generate a one-time workout without creating or accessing a user account or user profile by selecting the workout generator button 1315.

Figure 14:
FIG. 14 is a screen capture of the one-time workout view displayed by the interactive touchscreen of the automated station of FIG. 4.

Referring now to FIG. 14, selecting the workout generator button displays the one-time workout view 1400. This view can include a back button in the upper left corner 1402 that will direct the application to display the introductory view. There is also a strength button 1405 for generating a resistance workout and a cardio button 1410 for generating cardio workout.

Figure 15:
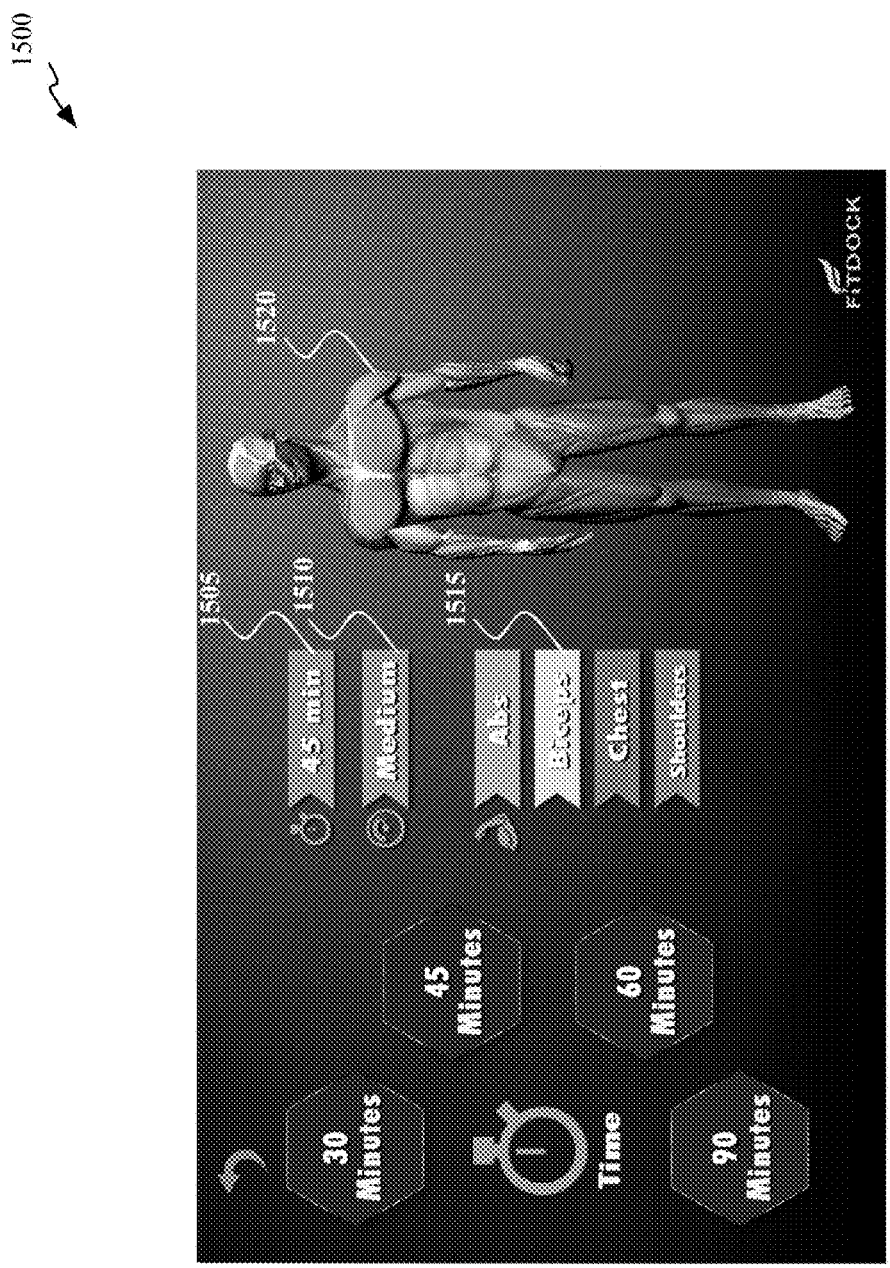
FIG. 15 is a screen capture of the workout parameters view displayed by the interactive touchscreen of the automated station of FIG. 4.

Referring now to FIG. 15, a workout parameters view 1500 receives different settings for use in workout generation algorithms. This can include setting the total duration of the workout, setting the intensity of the workout, and setting the muscle groups for the workout. In some embodiment, an anatomical graphic is displayed animating the different muscles and highlighting muscles to be exercised in this workout.

Figure 16:
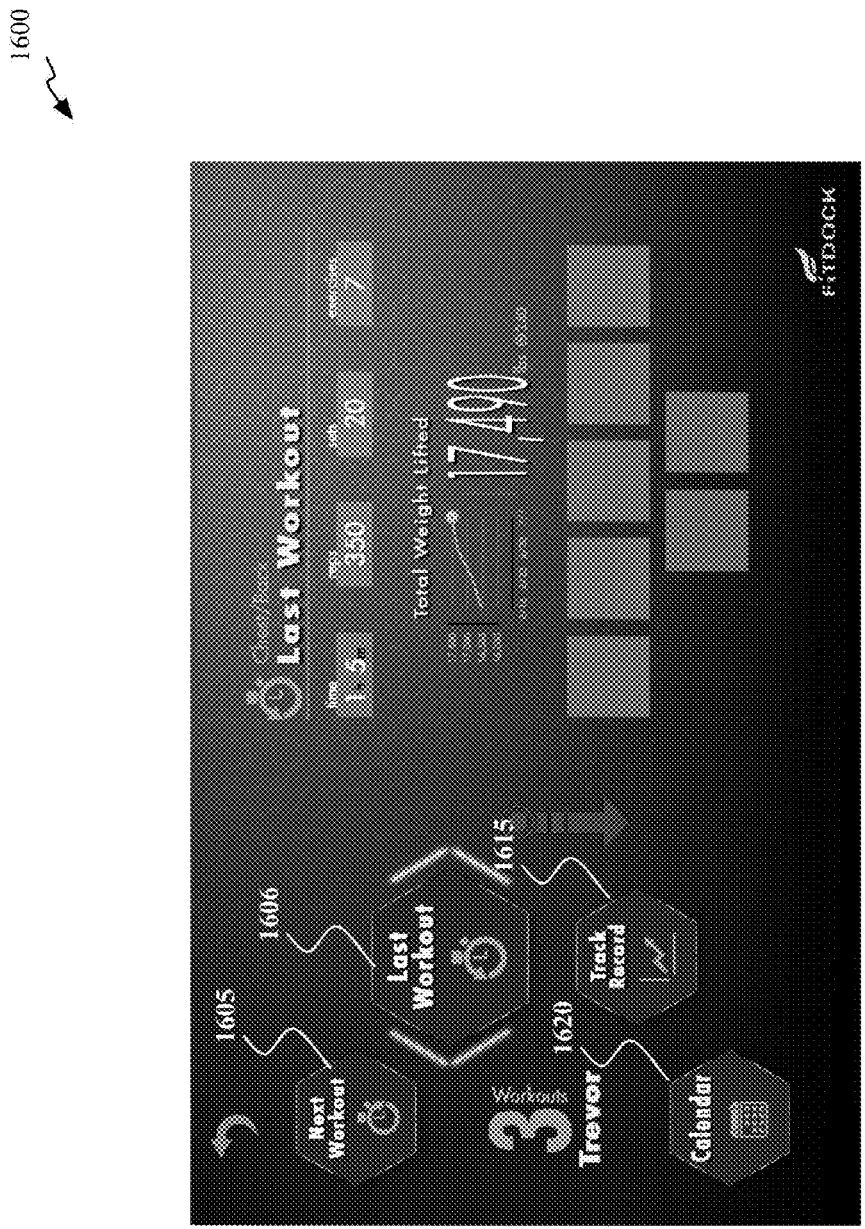
FIG. 16 is a screen capture of the user profile view displayed by the interactive touchscreen of the automated station of FIG. 4.

Referring now to FIG. 16, a user profile view 1600 displays the values and controls associated with the user profile. In some embodiments, the hexagon buttons 1605, 1610, 1615, 1620 to the left will animate in a circle as the user scrolls though the different options. Selecting a hexagon button populates the data display area on the right with stored data associated with the button selection event.

FIG. 17 depicts the interaction and cooperation between devices or components in some embodiments of the automated system operating within the computer network or similar digital processing environment of FIG. 1. Here, user 1702 interacts with one or more automated system applications 1703 running in automated station 1701 for various purposes, including but not limited to providing user profile data or receiving workout recommendations. As disclosed elsewhere herein, these applications may be running in whole or in part, in addition to or as an alternative to running on automated station 1701, on any other suitable computing device within said environment. Biosensors 1704, which may comprise at least one of any of the biometric sensors 290, sensors 805, or any sensor devices providing equivalent functionality are in data retrieval communication with user 1702 for the purpose of obtaining physical or biometric data. Biosensors 1704 are also in communication with automated system application 1703, which in turn is in communication with profile database 1705 for the purpose of storing and retrieving data obtained from user 1702 and biosensors 1704 for use by the automated system, including but not limited to use in generating workout recommendations for user 1702. Gym employee 1706 is also capable of interacting with application 1703 for any necessary purpose, including but not limited to administrative, troubleshooting, or maintenance functions. Again, none of the automated station, servers, mobile devices, and other devices of this system are in data or sensor communication with any machine, device, or other apparatus used by a user for the purpose of providing physical exercise. Applicant system is intentionally designed to be a functional equivalent of known systems that require data exchange with third party exercise machines for their functionality. Eliminating all dependence on such third party resources improves the versatility of the system disclosed herein and solves numerous problems in the known art.

Any number of other methods of exercise workout generation may be implemented using the resources provided and data collected and accumulated by the automated system. Whenever used herein with respect to the invention being disclosed, use of the term "system" is intended to apply to any or all of the various hardware, software, firmware, database, communication, networking, and other resources, elements, and devices described in this invention disclosure without limitation. Certain elements of the system may be integral to any one of the various aspects of the embodiments, others may be tangentially or optionally to such aspects, and certain elements may not be relevant to more than one of said aspects. The fact that a particular element, resource, or device may not be explicitly disclosed with respect to a particular embodiment is not intended to imply that it may not be applicable thereto, as it may well be.

Preferably, the system will be configured with more than one exercise workout generation method available to the workout generation engine. It should be appreciated that the system as a whole comprises many resources, elements, and devices that may be utilized in a particular embodiment in any combination without disparaging the usefulness of those or any other elements in another embodiment. Explicit disclosure of all possible embodiments of various combinations envisioned by this disclosure would be excessively burdensome due to the sheer number of possibilities. Having read and understood Applicant's disclosure, a person of ordinary skill in the art would immediately appreciate any number of embodiments envisioned but not specifically disclosed herein given the nature of the system and the obvious interdependence of the many resources. Any method comprising any or all of the system resources disclosed herein represents an embodiment contemplated by this disclosure, but exemplary methods are described in detail for purposes of illustration and not limitation.

Selection of one particular method embodiment of exercise workout generation over other method embodiments for which the system may be configured may be made based on any number of criteria. By way of example and not limitation, the combination of a user's input data and measured biodata may be particularly well-suited for one embodiment and not another based on success indicated by aggregated anonymous data of similar users collected by the system over time. Consideration of user's history of injury enabled in a particular embodiment would not be applicable to a user with no history of injury, enabling the use of an embodiment not comprising such consideration. A final non-limiting example of how one method embodiment may be selected over another involves the user's willingness to provide input to the system containing his preferences and goals. While the best results of the system will be obtained for users agreeing to provide all requested information to the system, some users may decline to do so. A new or one-time user may prefer to obtain a simple workout not based on any prior history, user preferences, or goals. In that circumstance, a simple method embodiment may be used that bypasses all consideration of such factors that would play an important role in other embodiments. While selection of one specific method embodiment over others is preferably made by the system, the method embodiment may be selected in concert with the user by providing several choices from which the user may select. Alternatively, the method embodiment may be selected directly by the user, overriding the determination of the system.

In addition to the methods disclosed elsewhere herein, and with reference to one exemplary embodiment of an exercise workout generation method, a new user may enroll in the system by providing the initial information disclosed above including a username, system password, e-mail address, name, age, height measurement, waist measurement, chest measurement, sex, somatotype (ectomorph, mesomorph or endomorph), any history of illness or injury that may affect their ability to perform certain exercises, a self-assessment of their present general physical condition, and the approximate number of times they exercise or perform strenuous physical activity per month. If the system hardware available to the user is configured to provide location information, said location is retrieved by the system and associated with the initial information provided by the user. For example, a fixed-location hardware station device may have its geographic coordinates or other location data stored in local memory, a hardware device may be able to retrieve its location via one or more networked services, or a hardware device may be able to determine its location via GPS or any other location service application active or available in said device. If a hardware device is not configured to provide or obtain location data, or if said data is not available to the device for any reason, the user may be prompted to provide his location via direct entry or menu selection. Such location data may comprise a street address, a telephone area code and three digit local exchange, a ZIP code, or any other location information suitable for the system to locate exercise resources proximate to the user. All data provided by the user and that obtained by the hardware device and system is stored by the system in the user's profile for future use in a manner identical to that of previously disclosed embodiments.

Also in the manner described above, the user may optionally be prompted to provide one or more user preferences, including but not limited to the type(s) of exercise(s) or exercise resources (machines or devices) the user may enjoy more or less than others. When the user indicates a preference for one exercise resource machine over another, the system may be configured to prompt the user to indicate whether the preference is based on direct experience with that machine or is based on some other criteria. If a user has routinely used a similar or identical machine, permitting the user to select the familiar equipment when prompted will improve his exercise experience. It may also permit the system to prescribe a longer or more intensive workout due to the user's familiarity with the resource where no learning is required. If the user indicates a preference for a machine which he has never used before for the purpose of determining a preference to be selected for future workouts, the system may be configured to allow additional time for the user to become familiar with the equipment for the first time.

Additionally, the user may optionally be asked to provide one or more goals to which the exercise workout routines may be preferably directed, including but not limited to losing weight, gaining muscle, reducing body fat, improving overall fitness, rehabilitation from injury or illness, or the like. Preference and goal data obtained from the user is stored in the user's profile for later use in generating an optimal exercise workout routine optimized for that particular user.

The system obtains biodata from the user, including the weight of the user via the weighing scale [270] and one or more bioimpedance measurements via the two or more sensors 805 or any sensor devices providing equivalent functionality, and stores said data in the user's profile for the dual purpose of determining an historical record of said biodata and using both the current data and historical trends in the method of generating an exercise workout routine.

Also in the manner described elsewhere herein, the system uses the location data provided or obtained as above to determine which specific exercise resources are available at all of the known facilities within a certain radius proximate to the user and to create a list of said facilities and resources. Further, as above, a list of exercises associated with and particularly well-suited for said exercise resources is obtained. The lists of resources and exercises are temporarily stored by the system for use in the exercise workout generation process to follow.

In this exemplary embodiment, exercises are not randomly selected as in other embodiments but are selected based on an assessment of the myriad of each user's input data and biodata in conjunction with the available exercise resources and associated exercises obtained by the system. By analyzing said data and providing certain criteria to link the applicability of certain data to other data, the system can provide maximally beneficial exercise workout recommendations to a user. Understanding how each of the various data may be used will enable a person of ordinary skill in the art to appreciate how the system may be configured to generate said exercise workouts. Each of the data employed in any given embodiment may be used to include or exclude certain activities, require or limit physical activity of a certain level, enable or disable consideration of other elements, and the like.

The order of consideration of each of the various data values is presented in accordance with the exemplary embodiment being described. However, in other embodiments, consideration of the data in a different order may be preferred. In general, the order in which data is acquired is not relevant to the process of exercise workout generation, as all data will generally be acquired in advance of such generation. One exception would be when the workout generation engine prompts a user to select one or more exercise options available to a user when a substitution is required following initiation of the workout generation process. This optional selection is described in greater detail below. Similar to the use of system elements in any of a myriad of potential combinations, some or all of the data may be used in different embodiments.

The user's age is preferably a primary consideration for any exercise workout generated by the system. Above all else, the system must be configured to provide safe exercise workout recommendations for the user without risking the user's health or presenting an appreciable risk of injury. Users will preferably be required to acknowledge that any physical activity includes some degree of personal risk due, such as accidental injury or unintended consequences beyond the control of any third party, but the system disclosed herein will be configured to reduce said risk as much as practicable. Younger adult users are generally less prone to injury or strain from exercise than are older users, so the system preferably establishes demarcations in age as one of its initial determinations. For example, one such demarcation may occur at age 30, another at age 50, and another at age 70. Demarcations at other ages may be implemented in lieu of or in addition to those listed. Certain exercises particularly suitable for users under 30 may be acceptable for users between 30 and 70 but may pose an unacceptable risk for users over 70. When such youth-directed exercises are available based on the exercise resources proximate to a user, the system's workout generation engine may preferably select them for younger users, select them for middle age users only when preferred alternatives are not available, and bar them from being selected for older users. In addition to selecting exercises based in part on the user's age, prescription of other factors such as exercise intensity and duration are also selected by the workout generation engine consistent with the user's age and other factors discussed below.

Another consideration pertinent to a user's age is the selection of particular exercise resources. Certain exercise resources (machines) may require a greater degree of balance, core stability, or coordination than others. Exercises on those machines may not be well-suited for older users unless such users have prior experience those machines; this is a particular illustration of how a user's preferences may modify the exercise workout to their advantage. While the system may not normally select one or more exercises on a certain machine for a particular user, if the user has indicated a preference for that machine based on prior experience, the system may be configured to consider the user's preference over its otherwise unguided selection and select exercises to be performed on that machine.

For certain users, their age and biodata may be used in combination by the system to select exercise resource machines that either use, or do not use, the user's weight as a component of the exercise. For example, a particularly heavy user at a relatively advanced age may not be well-suited to perform exercises that require him to lift all or even a portion of his body weight. Instead, a machine that affords the opportunity to provide a less strenuous exercise with a lower resistive force would be better suited until the user's biodata indicates that his weight and physical condition is consistent with exercises relying on all or part of his body weight. While evaluation of body weight resistance exercises in view of weight and physical condition may be utilized for users of any age, it is particularly important for older users more susceptible to injury, especially at the beginning of their exercise regimen.

Other factors for which age plays an important role include the maximum heart rate of the user, the duration of the exercise workout, the number of repetitions performed in each set, the rate at which those repetitions are performed, the amount of rest permitted between sets of repetitions, and the total number of sets comprising each exercise workout. Biosensors 805 or other means may be utilized between sets, between groupings of different exercises, during periods of rest, or as a specifically-prescribed non-exercise measurement activity within an exercise workout to measure the heart rate of a user for the purpose of adjusting the present exercise workout or for use in generating future exercise workouts. By obtaining and storing this data in the user's profile, an historical record is established to permit the system to provide the optimal safe workout for the user.

Particularly in the early stages of an exercise workout regimen, it is important to establish a proper balance between the intensity and duration of exercise needed to progress toward the user's goals at an appropriately safe level. An exercise workout that is insufficient for a particular user may be merely ineffective, but an excessive workout may be harmful to the user and introduce an unnecessary and undesirable risk of physical injury. For this reason, it is highly preferable that a user's self-assessment of their physical condition, recent history of exercise workouts or comparable physical activity, and potentially relevant injury history be known to and considered by the system. Users with no recent exercise experience or significant physical activity will preferably be matched to less strenuous exercises initially, with the intensity increasing as does their experience. Certain machines and associated exercises may be less suitable for new users than others, so use of those machines may be deferred until later whenever practicable. Factors such as the number of repetitions per set, the number of sets, the amount of rest between sets, and the amount of weight or other restive force applied against the user's efforts, to name several but not all criteria, will be considered in view of the user's experience by the workout generation engine during exercise workout generation. As disclosed above, none of the criteria are considered independently of the others; all criteria used to generate an exercise workout are evaluated in concert with each other.

Users who have experienced a prior injury that may limit their ability to perform certain exercises, and who have preferably disclosed such injury to the system, may receive additional options in the exercise workouts generated by the system. Not only will such injuries be considered when specific exercise are selected for the user, but the system may be configured to provide one or more alternative exercises in lieu of the system's preferred selection. In this manner, the user may elect an alternative option that may be less effective than the recommended exercise but more comfortable to perform. Users may be presented with the opportunity to select one or more substitute exercise during the workout generation process. A reduction in intensity may be achieved in some cases by prescribing reduced weight. In some cases, additional repetitions may be recommended to compensate for any diminution in intensity from the system's preferred exercise. The user may be instructed to perform the required repetitions at a slower pace or to stop performing the exercise in the event of pain or discomfort beyond that attributable to normal muscle fatigue. In some cases, certain exercises may be barred for users with certain injuries deemed likely to risk re-injury from said exercise(s). Any means available to the system may be employed to accommodate a user with an increased risk of harm due to prior injury.

Some injuries may be classified as structural, particularly those involving bones, joints, or ligaments. Effective treatment of these injuries is generally beyond the scope of the present invention, and the principal focus of the workout generation engine with regard to these injuries is to avoid any substantial risk of further harm to the user. However, in some instances, users reporting certain injuries properly classified as muscular discomfort may benefit from exercises directed to strengthen certain parts of their body or to alleviate pain via other means. In this manner, the workout generation engine may select certain exercises deemed both safe and effective for such users, including exercises for muscle development, stretching, and the like. Typical muscular-related problems include, but are not limited to, neck pain, lower back pain, certain types of repetitive stress injury, and the like. In some embodiments, the workout generation engine is configured to recognize these problems and offer the user, as an additional user goal or preference, the opportunity to include exercises considered to be therapeutic for such problems within an exercise workout. Such exercises are preferably optional, prescribed only with the prior approval of the user, and initially performed with low intensity until the user provides a positive indication to the system that the therapeutic exercises are achieving the desired effect. Until such time as the muscular discomfort is resolved, the workout generation would not prescribe any exercise likely to exacerbate the user's discomfort or any exercise during which the user's form may be affected by the discomfort. For example, a user with non-structural lower back pain may not be subjected to exercises where proper form requires a certain posture difficult for the user to achieve and where improper form would therefore be likely.

Proper form is critical to the performance of any effective exercise activity and not just those associated with previously-injured users. Improper position or movement during an exercise may fail to provide the intended benefit while risking injury to the user. The objective is not to perform the prescribed activity by any means, but by the proper means; execute the proper motion while remaining in the correct position so as to exercise the intended muscles with the intended intensity. In this regard, the user's experience level will guide the system in selecting the optimal exercises for users without much experience, said exercises comprising a lower level of difficulty than those suitable for more experienced users. Users already accustomed to machines or activities requiring greater skill, balance, or coordination may be prescribed exercises deemed too complex for users at a lower experience level. As the inexperienced users acquire greater skills and familiarity, the system will recognize this fact and begin to migrate them to exercises both suitable for their goals and more complex in their execution. Further, proper form is encouraged by maintaining an appropriate weight or other resistive force presented to the user. Requiring excessive force from a user during an exercise often encourages bad form as the user struggles to provide that force. As users gain both experience and strength as a result of their continued exercise, the weight or resistive force presented to the user may increase while allowing them to exhibit proper form. At the same time, the overall intensity of the workout will generally increase to maintain the appropriate level of exercise and development sought by each user.

A user's experience may also be indicative of his level of fitness. Users who routinely participate in exercise or activities that provide the same level of exertion are much more likely to be physically fit than users who do not. Users who provide an acceptable self-assessment of their present general physical condition and a recent history of exercise or physical activity may be identified as candidates for more advanced or rigorous exercise workouts than those who do not. A user who has not exercised recently may be considered to be inactive, two to three exercise sessions is generally considered to be moderately active, and more than three exercise sessions per week indicates that the user is active and likely in good physical condition. This data is preferably considered by the workout generation engine in selecting exercises along with their duration and intensity. As disclosed elsewhere herein, it is a significant advantage of the present system that it is configured to generate exercise workouts for users that are neither too rigorous nor insufficiently rigorous, properly matching the generated exercise workout to the user's capability and goals without a disproportionate risk of injury.

Numerous considerations affect the selection of the duration and intensity of prescribed exercises. Repetitive exercises comprise a number of repetitions that are preferably selected based on such factors as a user's goals, somatotype, experience, and safety as discussed previously. A high number of repetitions are beneficial for weight loss and body fat reduction, particularly for beginning users where proper form and injury prevention are paramount. Usually, high repetitions are prescribed with lower weights or comparable resistive force. This combination may also be particularly well-suited for a user seeking muscle development and endurance. It also produces a sustained cardio workout with an elevated heart rate deemed most effective for burning body fat. In contrast, very experienced users with relatively low body fat content striving for significant muscle development will receive exercise workouts with fewer repetitions, sometimes fewer than 10 per set, against a very high resistance. Here, a lower heart rate will generally be maintained but muscle tissue development will be accelerated. As a general rule, developing greater muscle endurance requires an increased number of repetitions with less weight, while developing greater muscle strength requires the use of more weight with significantly fewer repetitions.

With respect to rest, users seeking weight loss will generally receive less rest between exercise sets so as to keep their heart rate and glycogen level within the optimal range for burning calories. Users performing high intensity exercises with limited repetitions will generally receive greater periods of rest between sets to allow muscle recovery; maintaining an elevated heart rate is not conducive to achieving their goals of muscle development. As explained elsewhere, users of an advanced age may receive additional rest for safety reasons. As previously disclosed, the exercise workout generation engine is configured to consider all relevant factors presented by the user and measured by the automated station when determining and prescribing a series of individual activities that comprise exercise workouts.

Measured biodata obtained from the user via one or more system hardware devices is essential to several aspects of the system, including the method embodiment now being described. The weight of a user is a fundamental physical characteristic useful alone or in combination with other data. Obtaining and storing a user's weight over a period of time is obviously useful by itself in tracking the weight loss of a user seeking that goal. In combination with the user's height, preferably supplied by the user or, in certain embodiments measured by system hardware, the user's weight permits calculation of his body mass index (BMI). This figure permits assessment of the user's overall body profile and permits accurate tracking of a user's overall progress in an exercise regimen. Users with high BMIs are very likely to have a high percentage of body fat and will require a certain degree of weight loss before exercises directed to other goals, such as development of particular muscle(s), will be effective. However, certain other users may have a high BMI as a result of significant muscle development, where muscles instead of fat comprise a larger than average portion of their body weight. The system includes other means to distinguish between the two types of high BMI users. For example, a high BMI user that reports extensive exercise experience is likely to have more muscle than fat, while the inexperienced user is much more likely to have more fat than muscle. Additionally, the biosensors discussed elsewhere in this disclosure are operative to measure the conductive characteristics of the users body wherein fat and muscle tissue present very different results, permitting the system to distinguish between muscular users and fat users. When recommending exercises as a component of a larger workout, the difference between the two types of users is essential to provide a sufficient and safe exercise workout for both.

A user's weight is also an important consideration in the selection of exercises to include in an exercise workout. Certain exercises will not be appropriate for heavy users with high BMIs, particularly those where their weight provides a resistive force acting against their efforts. In particular, high BMI users may be unable to perform any chin-ups or pull-ups until their weight decreases to a reasonable level. In this extreme case, an exercise machine that permits the user to develop the same muscles with a lower resistive force may be selected by the system in conjunction with aerobic exercises directed to weight loss until the user is capable of beginning pull-ups with an increasing number of repetitions. In the other extreme case, a very thin user with a very low BMI may also lack sufficient muscle mass to complete any pull-ups at all and would benefit from the same machine. Another thin user with low BMI and sufficient arm strength to perform many pull-ups of his own lower weight, may require many additional repetitions beyond those required for a user with an average BMI and body weight to achieve a workout of the same intensity. Prescribing exercises of the proper intensity for all users is an important characteristic of the system, and knowing the users weight (and therefore, his BMI) is essential to this exemplary method embodiment and many other embodiments as well.

As disclosed elsewhere herein, the system may preferably comprise specialized analog electrical hardware machines for the purpose of measuring other characteristics of the users' bodies. In particular, these machines measure the bioimpedance of the user's body by passing a small alternating current at a known voltage to determine the impedance thereof, said impedance comprising both a resistive component and a reactive component as described elsewhere herein. While these machines comprising one or more biosensors may be used to obtain any useful data pertaining to a user's body, including but not limited to an estimate of the user's body fat as defined by the trend of measured bioimpedance data over time. As described above, muscle tissue and body fat exhibit greatly different electrical properties that are easily discerned by the biosensors 805 or any sensor devices providing equivalent functionality, enabling the system to evaluate each user prior to prescribing specific exercises best suited to their individual needs and goals. In order to achieve the best results possible, different exercises are required for users with different bioimpedances and therefore different proportions of body fat, and the system therefore requires machines and components to determine this important characteristic. Also, as with weight, obtaining and storing a user's bioimpedance over time permits the system to track said user's progress and determine how effective the system-generated exercise workouts are in achieving the user's goals and to determine when those goals have been met.

Separating a user's exercise into the general classifications of cardiovascular exercise (generally, fat burning exercises requiring an elevated heart rate) and hypertrophic exercise (generally, muscle development) may be based to a significant degree on a user's bioimpedance measurement. As described elsewhere, any required fat loss will generally precede any significant muscle building. As the loss of fat by a user may occur simultaneously with the development of muscle, measuring and recording only the user's weight will generally provide insufficient information for the system to include the proper balance of cardiovascular and hypertrophic exercise. However, considering the user's measured weight in concert with the user's measured bioimpedance provides the complete picture of said user's progress with respect to both fat loss and muscle development. A first user presenting a consistently low body fat percentage with increasing weight is clearly adding muscle, such results being consistent for some users undergoing a proper exercise regimen. However, a second user exhibiting a similar gain in weight with an increasing body fat percentage is gaining fat, not muscle, and a change in the exercises being prescribed by the system is clearly warranted. Without the machines and devices configured to measure body fat, an automated system would be unable to detect the difference between the first and second users and would fail to provide the optimal exercise workout for either or both users. Therefore, the machines and methods of deploying those machines for the measurement of users' body fat and other bioimpedance data are essential elements of the invention described herein.

Certain data provided by the user may be employed in combination with the weight and bioimpedance measurements obtained by system hardware machines and devices to determine other useful characterizations of the user's physiology. As discussed above, the user's height is a necessary parameter for the calculation of BMI. Preferably, users will be prompted to enter their height as a component of the input data provided to the system. However, one or more system components may be configured to comprise additional hardware machines or devices to determine users' height. For example, automated system 400 may further comprise a rigid or flexible extendable and retractable measurement element, such as a bar or a tape measure (not shown), disposed within support arm 410-a or 410-b that the user may extend to the top of his head. The system may then determine the degree of extension of the measurement element and record the user's height as a component of the user's profile, whereupon the measurement element is then retracted to its original position within support arm 410-a or 410-b. Other mechanical or electromechanical means configured to obtain the user's height are also envisioned by this disclosure.

Figure 18:
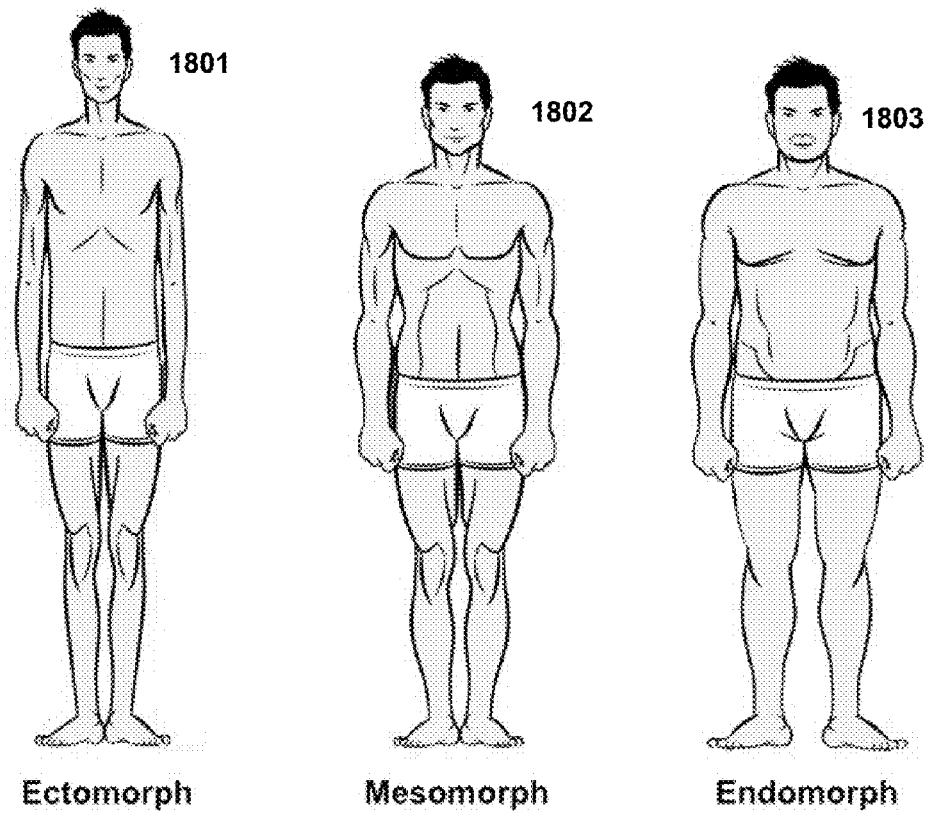
FIG. 18 depicts a generalized profile comparison of the ectomorph, mesomorph, and endomorph somatotypes.

Height and weight data permits useful determination of certain physiological characteristics, but additional useful correlation to tendencies involving exercise and weight loss may be determined via the user's structure and build, usually referred to as one of three common somatotypes. FIG. 18 depicts the three basic somatotype body structure taxonomies of ectomorph 1801, mesomorph 1802, and endomorph 1803. A methodology is known in the art by which specific user measurements may be employed to calculate, with precision, the proper classification for any user. However, even an approximate self-assessment of a user's somatotype is very useful in the generation of exercise workouts by providing general insight into the physiological response to exercise, diet, and the like. While the characterizations that follow are very general in nature and are certainly not representative of every individual who may conform to the general profiles presented in FIG. 18, they provide a good starting point for a user's exercise workout program at least until some degree of weight loss and muscle gain history has been established in response to the previous exercise workouts generated for, provided to, and performed by the user. Where examples of typical exercises are provided below, it should be recognized that they are exemplary and not limiting in any way.

Ectomorphs are naturally lean with slighter bone structures, longer limbs, and are the slowest of the three somatotypes to gain weight either in the form of fat or muscle. Muscular strength may be low due to the presence of decreased muscle tissue. Aerobic/cardiovascular exercise may be useful for ectomorphs to improve general fitness, including heart and lung functioning, but they may be less important than for other somatotype where weight loss (in the form of fat) may be desired. Ectomorphs generally benefit most from a focus on shorter workouts of mostly hypertrophic exercises, increasing to a fairly high intensity, to build tissue in the larger muscle groups. Muscle tissue development may well result in an increase in the user's weight, but such increase can be differentiated from weight gain in the form of body fat via system determinations of bioimpedance as discussed elsewhere herein.

Mesomorphs exhibit larger frames and are generally much more sensitive to factors that cause weight gain and weight loss. They generally possess greater dense muscle mass, thereby limiting their ability to lose weight below a certain point due to said muscle mass. Cardiovascular exercises with elevated heart rates may be more beneficial for most mesomorphs to control body fat than for ectomorphs. Mesomorphs also respond well to weight training for muscle development. When specified as a user goal, exercises directed toward muscle gain must be properly balanced with cardiovascular activities to achieve the best overall results within the time available for exercise workouts.

With a larger build and proportionately shorter limbs than the other somatotypes, endomorphs tend to retain fat more than the other types and generally require significant cardiovascular exercise to reduce weight and maintain good muscle tone. Exercises that lead to increased metabolism are particularly beneficial for endomorphs. In addition, higher intensity hypertrophic exercises are beneficial for strength development, as endomorphs typically gain muscle more easily than the other somatotypes. An exercise workout comprising both hypertrophic exercises, such as weight training, and cardiovascular exercises is necessary.

From the general overviews above, it can be appreciated that the distribution of exercises between hypertrophic and cardiovascular to be provided in the most effective exercise workouts should be determined in part by each user's somatotype. While other factors must certainly be considered as well, incorporating the user's self-assessment of somatotype as one means of determining the nature and focus of specific exercises incorporated into exercise workouts will provide a measure of general guidance. The workout generation engine will consider a user's somatotype, in combination with all of the other factors, in selecting exercises, their intensity, and their duration to be incorporated in generated exercise workouts.

User selection of a somatotype from three available choices is both simple and accurate to a degree, but further refinement of the user's physical structure will provide additional information useful in some embodiments to perfect exercise workouts for the user. In particular, bioimpedance measurement may be highly sensitive to certain dimensional characteristics of the human body. Most prior art bioimpedance measurements presume, for ease of calculation, that the body is essentially cylindrical with a uniform cross-sectional area of equal resistivity. This simplistic representation is useful in many applications but not as accurate as it may otherwise be. When combined with and correlated to measurements of a user's chest, waist, and hips, for example, a more accurate estimate of the user's actual bioimpedance may be obtained.

The tissue composition of a user's arms and legs, collectively and commonly referred to as limbs, are the principal factor in measured whole body bioimpedance determination but represent only a small volume of the user's body. For example, literature reports that the human trunk contributes about 9% of the total resistance of a typical bioimpedance measurement while it comprises more than 50% of the user's fat-free mass and body weight. In contrast, the forearms contribute about 28% to whole body resistance measurements but only contribute up to 2% of the fat-free mass and up to 3% of the body weight. Since the trunk comprises the largest store of body fat and comprises most of the major muscle groups, effective use of bioimpedance data in exercise workout generation sometimes requires scaling of said data using one or more physical characteristics, including the user's height, and preferably his girth measured at one or more cross-sectional points along the trunk (such as the chest, waist, and hips), for best applicability to the characteristics of the user's trunk where most fat is stored. In this manner, obtaining an index of body geometry permits appropriate correction of the raw whole body bioimpedance measurement to reveal factors otherwise masked by disproportionate contributions, such as those of the user's limbs. For example, whole body bioimpedance measurement data may be scaled by the square of the body height, the effective cross sectional ratio of the circumferential trunk measurements, or any combination thereof necessary to accurately correlate said measure data with the actual physiological characteristics of the user's body. Further, said scaled data may be correlated to other available data, including but not limited to the user's weight. In addition to scaling for whole-body measurements, measurement of only certain section of the user's body is possible via appropriate placement of the biosensors.

In certain embodiments, including the ones now being presented, certain preferences of users may be considered by the workout generation engine in a manner similar but not identical to the way a user's injury history may be considered. Preferably, other system input parameters form the primary basis for selection of specific exercises, their intensity, duration, and order of performance. These parameters are considered and applied as described elsewhere herein so as to provide the optimal exercise workout for the user. However, in embodiments where the user has expressed either a positive preference for one or more specific equipment resources, exercises, or the manner in which those exercises are performed, or a negative preference for any of the same, the workout generation engine may alter the intended exercise workout in accordance with the user's preferences. For example, if a user has a preference for one particular exercise resource machine over another or any reason, the system will accommodate the user's request by prescribing that any compatible exercise be performed on the preferred and available machine. Likewise, if a user specifically expresses disinterest in a particular machine, the workout generation engine will strive to prescribe a different machine, when available, for any compatible exercise. A user's like or dislike for a specific machine may be based on any criteria, including but not limited to factors such as prior experience with said machine, the machine's location within the exercise facility, the degree to which the machine provides an agreeable fit and feel for the user, and the like. Certain users may prefer to use free weights for upper body strength exercises while others may prefer to use machines that provide comparable resistive force in lieu of free weights. Some users may prefer to use an appropriate machine in lieu of doing pull-ups on a bar because the bar is uncomfortable to their hands. To the extent that the workout generation engine determines that the same results may be achieved with either exercise apparatus, the system may be configured to prescribe exercises consistent with the user's preference.

Other preferences expressed by a user may include the order in which prescribed exercises are performed. For example, one user may prefer that a certain exercise be performed earlier in the workout than has been provided in previous workouts. The workout generation engine selects and orders exercises, particularly compound exercises, in a manner to provide balance and sufficient periods of rest for certain muscles while others are being exercised, among other considerations. In this regard, the order in which exercises are performed is carefully selected for maximum benefit to the user in a manner consistent with best fitness practices. However, when a user provides input indicating a preference for a certain order or arrangement of exercises, the workout generation engine may be configured to accommodate said preference whenever re-arrangement is consistent with said best practices.

Any other manner of user preferences may be similarly accommodated, such as a user's desire for a longer workout in lieu of a shorter but more intense workout, or vice versa, if the workout generation engine determines that said preferences are an acceptable alternative.

When a conflict arises between proper exercise recommendations as determined by the workout generation engine and user preferences, the proper exercise recommendations will generally prevail. In this regard, user preferences may be regarded as a tweak, or minor adjustment, to an exercise workout determined and provided by the workout generation engine and not as a factor capable of countermanding such determination. In most instances, as long as the preferred adjustment provides essentially equivalent value to the user, the preference may be accommodated by the workout generation engine. This is an important distinction between the manner in which user preferences and injury histories are accommodated. When a user provides input that indicates a potential for injury, no exercise activity that presents any substantial risk of said injury will be prescribed by the workout generation engine. In other words, a potential injury risk is sufficient to preclude any specific exercise or performance of a specific exercise for a prescribed duration or above a certain level of intensity. The workout generation engine is preferably configured in these circumstances to provide alternate exercise options whenever available but is always configured to ensure the safety of the user in every exercise workout provided to said user. On the other hand, a user preference is generally insufficient to preclude an exercise from being selected by the workout generation engine. As described elsewhere herein, the system is configured to provide a workout with an appropriate selection of exercises and intensity. Permitting a user to diminish the value of workout via preference selection would defeat the value of said workout. However, when essentially equivalent results may be obtained consistent with preferences expressed by a user, the workout generation engine is preferably configured to provide an exercise workout according to said preferences. As disclosed elsewhere, permitting users to specify user preferences provides a useful secondary purpose that provides additional commercial opportunities.

In some embodiments, the system is configured to receive post-workout evaluations from users. These evaluations may be principally directed to the level of difficulty experienced by the users, but additional input may be obtained from the user as well. For example, providing an opportunity for users to indicate that the just-completed workout was too rigorous or not rigorous enough will enable the workout generation engine to adjust the subsequent workout accordingly. Although the system is configured to select exercises and prescribe an appropriate duration and intensity according to the same best practices observed by human trainers, the system is limited in its ability to obtain feedback from users comparable to that which a trainer would receive or observe since the system does not exchange data in real time, or at any time, with non-system exercise resources such as exercise machines. The system may be configured to record the time that the workout was provided to a user and the time when the user reports that the workout has been completed, thereby determining if the user required more or less than the anticipated time to complete the workout. Excessive elapsed time to completion may indicate that the user required (or simply elected to take) additional rest between exercises, while faster completion than required may indicate either that the workout was not rigorous enough for the user or that the user failed to complete all of the prescribed exercises. In either event, providing an opportunity for the user to advise the system of any such discrepancies will enhance the effectiveness of the exercise workouts generation process by permitting appropriate adjustments if and when needed. Further, a user's preferences for subsequent workout generation will be freshest in his mind immediately following completion of a present workout. The system may also be configured to weigh the user, measure bioimpedance, determine the user's heart rate, or collect and store any other useful information in any combination at the conclusion of an exercise workout for use in future exercise workout generation.

As described elsewhere herein, the workout generation engine selects and prescribes exercises based in part on the availability of exercise resources at the specific location selected by the user from the list of all facilities proximate to the user's geographic locale provided by the system from its database. In some instances, the user's injury history or preferences may be incompatible with the exercise resources available at the user's chosen location. Preferred equipment may not be available, the only equipment resources available at a particular location may be of the type not suitable because of risk of injury, or the like. In these circumstances, the system will advise the user of these limitations and, whenever possible, provide alternative exercises with the greatest possible level of equivalence. In some embodiments, the system may recommend another nearby exercise location where resources necessary for an optimal workout are available. In some embodiments, the generation of an exercise workout may be completed and provided to a user prior to his selection of a resource location so that the user may choose his preferred location from those within the same general area as a prelude to his exercise activity. In some embodiments, the user may request and receive a newly-generated exercise workout at the conclusion of a previous exercise workout along with a location chosen by the user or recommended by the system that offers the requested or preferred exercise resource equipment.

With respect to goals supplied by a user, the workout generation engine is configured to accommodate said goals to the greatest degree possible. For example, users primarily interested in weight loss may receive a preponderance of cardiovascular exercise to increase metabolism and burn fat. Other users may prefer to build muscle, either generally or with respect to specific muscles, and exercise workouts directed to that goal will be provided whenever possible. However, as when user preferences are considered, the workout generation engine maintains a proper balance of exercises and exercise intensity for the optimal benefit of the user when user goals are provided. In some cases, certain objectives, such as a degree of weight loss, may be required before appreciable development of any specific muscles can be realized. In these cases, a portion of the exercise workouts may initially be dedicated toward the user's stated goals but the primary focus of the workouts will be determined by the workout generation engine as indicated by the primary input and measured data. The selection of specific exercises, their intensity, and their duration are all subject to adjustment by the workout generation engine as deemed appropriate to accommodate the user's goals.

Having now presented the manner in which the various user data may be utilized by the workout generation engine, several examples of exercise workout generation will now be presented.

New user A, age 59, 6' 1" tall, 230 lbs., and a self-identified endomorph, reports that he exercises approximately 4 times per week and is therefore considered active and in generally good shape. User A establishes a goal to lose 15 lbs. as may be expected by someone who recognizes his profile as being that of an endomorph. His unscaled measured whole body fat content of 23% affirms his goal of losing weight. As such, significant cardiovascular exercise will be included in his workouts. From this data, the system determines that high repetitions of hypertrophic exercises with moderate weight will be preferred in order to maintain an elevated heart rate. The user also reports a degree of lower back pain that increases his present risk of injury if not properly accommodated, so the workout generation engine will avoid selection of inappropriate exercises and, with the consent of the user, select core stability exercises intended to strengthen the user's back muscles. The user indicates a preference that the entire workout be completed within 30 minutes, indicating that a faster pace is required than if additional time were available. The workout generation engine recognizes that the same exercises performed in a shorter period will achieve the same results. The system determines the user's location and obtains a list of all proximate facilities, the exercise resources located at those facilities, and the exercises that may be performed using those resources. In this case, the user's location is a hotel with a moderately well-equipped fitness center. The user is required to warm up sufficiently so that he is sufficiently limber and his muscles are prepared for the exertion to follow, but this time is preferably not included in the time allotted for the actual workout.

In this example, the workout generation engine selects exercises for the main groups of chest, abdominal, and leg muscles along with secondary groups of bicep, tricep, and calf muscles, in part because the user reported no prior injuries to any of these muscles, in part because they are large muscle groups capable of burning fat at a rapid rate, and in part due to other considerations including user A's preferences. The exercise workout provided to this user by the workout generation engine comprises, as the first component, the compound exercise of squats with bicep curls, in this case with 12 lb. hand weights, for three sets of 15 repetitions each with 30 seconds rest between sets. An older or less fit user may have been prescribed fewer repetitions, fewer sets, or lesser weights. No special exercise resources are necessary for this exercise (hand weights are ubiquitous and available at practically all exercise facilities) so there are no limitations based on location, no injury considerations, and no adverse user preferences.

The exercise workout comprises, as the second exercise in the workout, an alternating series of bicycle crunches (a combination of bicycle-like legs pumps combined with trunk rotations performed on the user's back) and push-ups; specifically, 30 repetitions of the crunch followed by 10 pushups in quick succession, without rest, for four cycles. The workout generation engine is configured to select this particular combination because muscles active in the crunch are not active in the pushups, allowing them to recover while the other are exercised. The lack of rest periods between the crunches and push-ups ensures that a high cardiovascular level is maintained throughout as desired to achieve this user's weight loss goal. The use of separate major muscle groups in each of the component exercises allow one to rest while the other is being exercised. No specialized resources are required for this component of the exercise workout.

The third exercise selected by the workout generation engine is another combination of a bench press combined with a pull-down (tricep focus) and calf raises, in this case three sets of 18 repetitions each with 20 seconds of rest between sets to allow partial recovery. At the conclusion of these sets, the user should be at or near the 21 minute mark of the 30 minute workout. These exercises may be performed using free weights or a suitable exercise machine based on the availability of the equipment and any user preferences that may be pertinent.

For the fourth and final component of the exercise workout, the workout generation engine selects sit-ups alternating with flutter kicks, 20 repetitions of each for three cycles with no rest between sets. Following completion of these four components, the final five minutes of the workout is dedicated to a static stretch as a cool-down activity.

User A is then provided an opportunity to provide feedback to the system via one or more of the devices available for that purposes, such as the automated station or a portable electronic device in data communication with another component of the system. The user may indicate any difficulties experienced during the workout, including his inability to complete any of the prescribed exercises, extreme or insufficient exertion, or any discomfort beyond that expected from a comprehensive physical workout. Any of the factors above may be cause to modify future workouts to better suit the user and his stated goals. The user may have also developed a preference for future workouts that may also be entered into the system as a part of this post-workout evaluation.

The method of generating exercise workouts based on a user's input data, biodata, goals, and preferences seeks to determine the results of a particular series of exercise workouts prospectively (in advance) of the actual performance of said workouts. An important advantage of the disclosed system is its ability to prospectively generate workouts specifically directed to the particular user's physiology and goals using information provided by and obtained from the user. This is a significant advancement from the current practice where many users haphazardly select exercises to perform without any guidance or underlying rationale. However, during the course of the user's participation with the system, a user's physiology, goals, or both may change over time. A novel feature of the system disclosed herein is its retention of user-supplied data and measured data, including the user's weight, bioimpedance, and other characteristics obtained via the biosensors, which is subject to constant updating each time the user engages the system and requests that a new workout be generated. By continually obtaining new measured biodata and providing the user with an opportunity to update the user-supplied information such as goals and preferences, the system is assured of generating the optimal exercise workout using latest data and information each time a new workout is requested. In this sense, the system adapts to the changing physiology and potentially changing goals of the user. Further, by maintaining a record of all historical biodata for each user along with the specific exercises performed by each user over that same period, the adaptive exercise workout generation system is configured to correlate results such as weight loss and biodata with specific exercises previously performed to determine which exercises produced the best results for that user and is further configured to prescribe them to the user, prospectively anticipating that the desired results will be achieved. However, in certain cases, the results of prospectively-determined exercise workouts may not provide the anticipated results, and the disclosed invention provides means by which to improve upon that said known limitation.

When the system detects that a user is no longer progressing toward his goals, the workout generation is configured to modify the exercise workouts generated for the user to comprise different exercises, or exercises of increased intensity or duration, in an attempt to advance the user toward his goals. Different muscle groups or exercises may be selected, progress toward the desired goals compared to previous results, and further adjustments to the exercise workouts be performed as indicated until the user resumes a sufficient level of progress. In some embodiments, the system may inquire of the user whether all of the prescribed exercises are being performed. Users must preferably be enabled to provide post-workout feedback where failure to complete the entire exercise workout for any reason may be reported. Absent such opportunity, the system should preferably inquire of users at the time an exercise workout is requested whether any exercises prescribed in the previous workout were not completed. The system will be unable to accurately correlate prescribed exercises with results for the purpose of improving subsequent exercise workouts if only a portion of the prescribed exercises are actually performed. However, when a user does report that his entire workouts are not being completed, the system is configured to modify subsequent workouts in such a way that the user is able to complete said workouts. Completing a less rigorous workout while building strength and endurance will enable the user to eventually complete more rigorous workouts that will advance them toward their goals. The system is accordingly configured to modify a user's goals when necessary to provide more reasonable short term goals on the path to attainment of their ultimate goals. Users not achieving the desired results should also be reminded that attempting to deceive the system will adversely affect their exercise experience, prolonging attainment of their goals and requiring extra time and effort. In some embodiments, a user may be reminded that factors such as diet have an effect on fitness goals and encouraged to be diligent in maintaining proper caloric intake between exercise workouts.

While the system is adaptive to the changing physiology of individual users via the means described above, it is also adaptive on a much larger scale with respect to the cumulative body of users. In one embodiment, a user's biodata, general physical information present in said user's profile such as somatotype, age, height, and the like, exercise workout specifics provided to each said user, and an assessment factor as described below indicating how effective previous exercise workouts of a similar nature have been for said user in the past (collectively referred to herein as metadata) may be associated with each other in any manner, anonymously aggregated with the metadata from other users via the networked infrastructure described elsewhere herein, and stored in one or more system databases in a repository comprising the metadata of said other users. No data that may possibly be used to identify the identity of the user, such as name, contact information, e-mail address, or the like would be useful to this embodiment and all such information would therefore be excluded from collection and aggregation. Preferably, users would be required to consent for their metadata to be anonymized and aggregated in this manner. Also preferably, but not necessarily, users would be required to permit the aggregation of their own anonymous metadata as an incentive to benefit from the aggregated anonymous metadata of other users.

As previously disclosed, the system provides adaptive exercise workout generation. By examining the user's supplied goals, his prior history of measured biological characteristics, and the exercises performed, the system is configured to adjust the parameters of each exercise workout provided to the user for maximum benefit. For example, as the user loses weight, the focus of exercise workouts may shift to muscle development if desired. When a user seeks to lose weight but the exercise workouts generated by the workout generation engine are not producing acceptable results, the workout generation will alter the exercise workouts provided to the user until the optimal results are being achieved. Sequential alterations will generally be provided in small increments unless the user suddenly presents information to the indication a major change in direction, such as dramatically altered goals, the occurrence of a new injury, or the like. In this manner, the system will always be aware of the users goals, the steps that have been taken toward attainment of those goals, the present state of progress toward attainment of those goals, and therefore the effectiveness of said steps in attaining the user's goals.

In a preferred embodiment, the system will determine an assessment factor for each workout generated based at least in part on the similarity of the present exercise workout to those previously generated and performed by the user, and also based at least in part on the degree of success experienced by the user in the performance of those previous exercise workouts. As one non-limiting example for purposes of illustration only, the similarity factor and the success factor may each comprise a number in the range between zero (0) and fifty (50). An exercise workout identical to a previously-generated workout may be assigned a similarity factor of 50, an exercise workout with several identical components but several modified components may receive a similarity assessment of 35, while an entirely different exercise workout may receive a similarity assessment of 0. Likewise, when one or more previously-generated exercise workouts have produced good results, a success factor close to 50 may be assigned to the present workout when generated. Lesser results would merit a lower success factor. Adding the similarity and success factors will produce an assessment factor between zero and 100, with the higher scores indicating that the workout generation engine has found the most effective workout possible for the particular user and has been consistently prescribing similar workouts in the recent past. Exercise workouts generated with varying content and success rates (as the workout generation engine attempts to find the optimal combination) will receive lower assessment factors. Any method of providing an assessment of an exercise workout based at least on a measure of demonstrated success is envisioned by the scope of this disclosure.

Over time, a large repository of metadata would accumulate in one or more system databases and provide a statistically large sample of exercises and their effect on users. Some exercise workouts will prove to be more effective with certain types of users than will others, thereby receiving higher assessment factors, and differentiating on that basis will be highly beneficial in providing optimal exercise workouts to users. For example, when the aggregated metadata is evaluated on the whole, a particular combination of exercises may be historically proven to be highly effective in rapidly building muscle in younger female ectomorphs while another exercise combination may be much less effective than others in weight reduction for middle-age male endomorphs. Accessing and analyzing the aggregated metadata by age, somatotype, biodata, or any other index or combination of indices corresponding to individual components of the metadata would yield an accurate historical determination of which particular exercises, associated durations, and intensities provided the best particular results for users whose with similar metadata and which did not. In this context, best results may be expressed as an optimal progress toward any goal determined by the system or provided by a user. For a weight loss goal, best results may be expressed in terms of any of total weight loss, rate of weight loss, maintenance of a consistent rate of weight loss, or the like. When reduction in body fat is a relevant goal, any of the amount of total body fat loss, the rate at which body fat is reduced, or maintenance of a steady rate of body fat reduction may be selected as the best or preferred result. For muscle development, best results may be determined by a combination of body fat reduction and weight gain attributable to increased muscle, the increased amount of weight or resistance prescribed in an exercise workout necessary because of increased user strength, or the like. Any available criteria may be established to determine best historical results and the metadata evaluated to determine which of the aggregated metadata is most pertinent. The workout generation engine may be further configured in this embodiment to either validate, modify, or replace any exercise workout generated via its prospective analytical methods to better conform to one or more historically effective exercise workouts obtained from the aggregated metadata. Here, historically effective exercise workouts are those that have achieved best results for previous users, where said best results are those determined as defined above with respect to goals determined by the system or supplied by the user. For example, exercise workout components or parameters shown to be particularly effective may be used to replace less effective components selected via analytical evaluation. In one embodiment, the aggregated metadata would be used only to permit disambiguation between multiple exercise options available to the workout generation engine and to select a preferred option from several possibilities. Major modification of a workout generated by the prospective analytical methods is not envisioned in this embodiment. However, in another embodiment, the aggregated metadata may be used to modify the workout generated by the prospective analytical method to any greater degree provided that said modification did not cause the resulting workout to contravene any of certain parameters supplied to the workout generation engine, such as those pertaining to a user's injury history, goals, or the like.

As the amount of anonymous metadata in the aggregated repository grows and exercise workouts generated by prospective analytical methods are correlated, conformed to the best historical result, and subsequently added to the aggregated repository, the workouts generated by the workout generation engine will inevitably gravitate toward said best historical results, thereby providing maximum benefit to users. Likewise, ineffective workouts not providing acceptable results will be identified as such and will represent a decreasing portion of those being generated. Exercise workouts provided to users via this embodiment will be based on best practices known in the art of prospective analysis-based workout generation with the additional insight of results obtained by actual historical performance of users with similar characteristics. Since all of the exercise workouts generated by this embodiment will have originated via best practices in prospective analytical exercise workout generation, the superset of aggregated anonymous metadata and associated exercise workouts will be similarly compliant with best prospective analytical practices.

Correlating a user's metadata with that of similar user metadata in the aggregated repository provides guidance regarding which of several potential exercise and intensity options available to the workout generation engine should be selected to achieve best results for said user. In this manner, the disclosed system ensures that exercise workouts generated for users are both prospectively analytical and historically proven. Generating exercise workouts solely based on historical results would ignore many of the important prospective analytical factors, such as prior injuries, individual user goals, and the availability of necessary exercise resources proximate to the users. The preferred method of analytical generation of exercise workouts with subsequent validation, and possible modification, of said workouts based on historically effective results is novel in the known art and represents a substantial improvement thereto while solving the problem of limitations on the effectiveness of prospective-only workout generation. In common parlance, consideration of the efficacy of exercise workouts "closes the loop" on open-ended workout generation methods using analytical methods where results are not applied to the perfection of said analytical methods.

In one embodiment, the workout generation engine may refer a user's metadata to the repository comprising one or more databases of aggregated metadata as an initial step, thereby obtaining one or more historically effective exercise workouts that correspond to other users with metadata similar to that of the user. Subsequently, the workout generation engine in this embodiment may evaluate each of said historically effective exercise workouts analytically based on all of the information in said user's profile, including data not present in the metadata of the user or in the metadata associated with the historically effective exercise workouts. For example, without creating limitation on this embodiment, users' metadata will typically not include information about their injury history. If the workout generation engine detects one or more exercises in a particular historically effective exercise workout to be incompatible with the present user's injury history, the workout generation engine would either discard that particular historically effective exercise workout from further consideration or modify said workout by substituting a compatible exercise for any exercise(s) incompatible with the user's injury. As with the prior embodiment, the exercise workouts generated in this latter embodiment and all associated metadata may also be aggregated in the repository for the further benefit of other users. As the final exercise workouts generated via this embodiment has also been subjected to analytical review by the workout generation engine to assure compliance with best practices, such workouts provide the same degree of dual-standard validation (both analytical and historical).

The principal difference between the prior and the latter embodiments of adaptive exercise workout generation is the order in which the prospective analytical factors and the historically effective factors are applied. In the prior embodiment, a prospective analytical exercise workout is first generated based on all of the user's information available to the workout generation engine and said workout is subject to some degree of adjustment by comparison to historically effective exercise workouts retrieved from the repository for users with similar metadata. In the latter embodiment, a user's metadata is first compared to the metadata of other users and historically effective exercise workouts associated with said metadata are retrieved. Said historically effective exercise workouts are then analytically evaluated against all of the user's information and said historically effective exercise workouts are modified, as necessary, to conform the final exercise workout provided to the user to any analytical requirements. Both embodiments and believed to be novel in the art and offer significant advantages over said art.

When one or more historically effective exercise workouts are retrieved from the repository of aggregated metadata in any embodiment described or envisioned herein, the workout generation engine incorporate and assimilate the data therein into a new exercise workout any preferred manner. For example, without creating limitation, the workout generation engine may select the historically effective exercise workout with the best results, may randomly select one of any of the historically effective exercise workouts within the top tier of available historically effective exercise workouts, may select a subset of all of the historically effective exercise workouts determined by any preferred selection criteria and calculate an average (mean, median or mode) set of criteria to apply toward the exercise workout being generated, or may generally incorporate any or all of the individual components from one or more historically effective exercise workouts for inclusion in a newly-generated exercise workout.

An additional advantage of one embodiment of this invention permits evaluation of exercise resources and locations. When user preferences are also anonymized and aggregated as components of users' metadata, their positive and negative preferences may be analyzed to determine which particular exercise resources are preferred. To some degree, the availability of machines at different facilities within a user's geographic locale will preclude a highly accurate determination of which exercise machines are favored over those of a competitor. However, user preferences may be scaled according to availability within a particular region and a general indication of which machines are more popular than others may be obtained. This data may be provided to equipment manufacturers and distributors for marketing purposes as an additional component of the various business models enabled by the system describe herein.

As a non-limiting example, new system User B primarily interested in losing weight will almost certainly do so provided that the user performs the workouts generated by the system and maintains a reasonably consistent diet. Increased physical activity with a constant caloric input is well known to produce weight loss in all but the most unusual circumstances or physiologies. Generally, users who provide a sufficient quantity of sufficiently accurate input data will achieve weight loss results at an acceptable rate from the prospective exercise workout generation methods taught herein. However, different users will generally experience different rates of weight loss governed by their metabolism and other factors associated with their particular somatotype. An acceptable rate for one user may not be deemed acceptable to another. As long as the user maintains satisfactory progress in his view (and is considered to be "on track" according to the system's predetermined standards) and does not modify his stated weight loss goals or workout preferences, the workout generation engine may continue to generate workouts for User B generally consistent with those that have proven to be effective for him. If the user modifies his goals to specify a greater degree of weight loss midway through his program, the workout generation engine may select new exercises or provide new durations or intensities for previously-prescribed exercises. Should the user express a preference to avoid a familiar exercise or add a new exercise, the workout generation engine may substitute something new for something known provided the preference is consistent with its own determination. However, at some point short of the user's desired weight loss goal, the user may exhibit a "plateau" where the rate of weight loss slows or stops altogether. As said user's weight is repeatedly measured and stored by the system, the exercise workout engine will detect the fact that the user is failing to make progress toward his stated goal. In one embodiment, the system will modify the user's subsequent exercise workouts in an attempt to jump start the user's previous rate of weight loss as described above. In an embodiment comprising one or more databases of aggregated metadata, the workout generation engine may access said aggregated metadata to search for users with similar metadata, examine the results of exercises prescribed for said users, and modify the exercise workouts prescribed for user B according to some or all of the most successful user metadata previously aggregated for reference. At the same time, User B's metadata will be added to the aggregated data for the benefit of future users. This process will repeat iteratively to maintain acceptable progress toward the user's goals until they are reached via the adaptive process of exercise workout generation.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures may be implemented to achieve the same functionality.

The process parameters and sequence of steps described and/or illustrated herein are given by way of example only and may be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The various illustrative blocks, components, and engines described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, multiple microprocessors, one or more microprocessors in conjunction with a DSP core, or any other such configuration.

Furthermore, while various embodiments have been described and/or illustrated herein in the context of fully functional computing systems, the functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Feature implementing functions may also be physically located at various positions, including being distributed such that portions of functions are implemented at different physical locations.

Unless otherwise noted, the terms "a" or "an," as used in the specification and claims, are to be construed as meaning "at least one of". Thus, for example, a list of "at least one of A, B, or C" means A or B or C or AB or AC or BC or ABC (i.e., A and B and C).

In addition, for ease of use, the words "including" and "having," as used in the specification and claims, are interchangeable with and have the same meaning as the word "comprising." In addition, the term "based on" as used in the specification and the claims is to be construed as meaning "based at least upon." Also, the term "immediately" with respect to a delay of machine action means without delay typically perceivable by human users.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

What is claimed is:

1. An electronic fitness improvement system comprising:
   A. at least one weighing scale;
   B. at least one bioimpedance measurement machine comprising two or more analog biometric sensors in electrical signal communication with
      i. the body of a user,
      ii. at least one alternating current (AC) analog voltage signal generator,
      iii. at least one analog AC voltage measuring device, and
      iv. at least one analog AC current measuring device;
   C. one or more network servers comprising one or more databases; and
   D. one or more instance(s) of fixed location or mobile application(s) in data communication with said one or more network servers, wherein the operation of each particular instance of said fixed location or mobile application is associated with a particular user; wherein the system is configured to:
      a. receive, from said one or more instance(s) of the fixed location or mobile application(s), information about the type of exercise resources and their location at more than one exercise facility accessible to system users and store said information in said one or more databases;
      b. obtain the location of a particular system user;
      c. measure the weight of said particular system user via said at least one weighing scale;
      d. measure the bioimpedance of said particular system user at one or more frequencies via said at least one bioimpedance measurement machine;
      e. retrieve, from said received information about the type and location of exercise resources more than one exercise facility accessible to system users previously stored in said one or more database(s), information about the type and location of exercise resources at more than one exercise facility within the geographic locale of said particular user;
      f. use at least said retrieved information about the type and location of exercise resources within the geographic locale of said particular user, the measured weight of the particular system user, and the measured bioimpedance of the particular system user to generate an exercise workout recommendation for said particular system user; and
      g. provide information about the type and location of exercise resources within the geographic locale of said particular user and the generated exercise workout recommendation to said particular system user via the fixed location or mobile application associated with said particular user.

2. The system of claim 1 wherein said at least one weighing scale, said at least one bioimpedance measurement machine, and one of said one or more instance(s) of fixed location application(s) comprise a fixed location automated station accessible to one or more system users.

3. The system of claim 2 wherein said automated station, said one or more network servers, and said one or instance(s) of a mobile application operate independently of, and without data communication to or from, any machine, device, or apparatus configured to provide physical exercise to a user.

4. The system of claim 1 wherein said at least one AC analog voltage signal generator is configured to generate one or more of any of a periodic fixed-frequency sinusoidal signal, a periodic fixed-frequency non-sinusoidal signal, a periodic variable-frequency sinusoidal signal, and a periodic variable-frequency non-sinusoidal signal.

5. The system of claim 1 wherein the system is further configured to use additional information to generate said exercise workout recommendation for said system user, such additional information comprising at least one of any data pertaining to said system user's age, height, sex, somatotype, goal data, exercise workout preferences, health or injury history, or previously-generated exercise workout recommendation(s).

6. The system of claim 5 wherein said goal data comprises data pertaining to at least one of any of weight loss, muscle building, a combination of weight loss and muscle building, a target weight, a target body fat percentage, target muscle building, cardio duration, resistance duration, cardio intensity, and resistance intensity.

7. The system of claim 5 wherein said exercise workout preferences comprise at least one of any of specific exercises to be performed, specific exercises to be avoided, specific exercise equipment to be utilized, specific exercise equipment to be avoided, specific muscles to be developed, preferred cardio exercise duration, preferred cardio exercise intensity, preferred resistance exercise duration, and preferred resistance exercise intensity.

8. The system of claim 5 wherein said system is further configured to aggregate said generated exercise workout recommendation, said measured weight of the system user, said measured bioimpedance of the system user, and said additional information into a single metadata record and to communicate said metadata record to said one or more network servers for storage in said one or more databases.

9. The system of claim 8 wherein the system is further configured to retrieve at least one metadata record previously stored in said one or more databases and is further configured to include the data in said at least one metadata record as additional information used to generate said exercise workout recommendation.

10. A method for providing exercise workouts, the method comprising:
   A. providing at least one weighing scale;
   B. providing at least one bioimpedance measurement machine comprising two or more analog biometric sensors in electrical signal communication with
      i. the body of a user,
      ii. at least one alternating current (AC) analog voltage signal generator,
      iii. at least one analog AC voltage measuring device, and
      iv. at least one analog AC current measuring device;
   C. providing one or more network server(s) comprising one or more database(s), at least one of said one or more database(s) comprising previously-generated and stored exercise workout recommendations and at least one of said one or more database(s) comprising a list of exercise resources and exercise machines available at more than one exercise resource location;
   D. providing, to said user, an instance of a fixed location application in data communication with said one or more network server(s);

E. electronically obtaining the geographical location of said user;
F. retrieving, from said at least one of the one or more database(s), a list of exercise resources and exercise machines available at more than one exercise resource location within a specified distance from said geographical location of said user;
G. measuring the weight of said user via said at least one weighing scale and measuring the bioimpedance of said user at one or more frequencies via said at least one bioimpedance measurement machine;
H. generating or retrieving, via said one or more network server(s) or said fixed location application, at least one first exercise workout recommendation comprising one or more first exercise workout instruction(s) based on said measured weight of said user, said measured bioimpedance of said user, and said list of retrieved exercise resources and exercise machines;
I. retrieving or generating, via said one or more network server(s) or said fixed location application, at least one second exercise workout recommendation comprising one or more second exercise workout instruction(s) based on said measured weight of said user, said measured bioimpedance of said user, and said list of retrieved exercise resources and exercise machines;
J. modifying, via said one or more network server(s) or said fixed location application, none, some, or all of said one or more first exercise workout instruction(s) to more closely conform to any one or more of said one or more second exercise workout instruction(s) to create a third exercise workout recommendation comprising one or more third exercise workout instruction(s); and
K. providing said third exercise workout recommendation and said retrieved list of exercise resources and exercise machines to said user via said instance of the fixed location application and storing said third exercise workout recommendation together with the measured weight of said user and the measured bioimpedance of said user in said at least one of the one or more database(s);
wherein said second exercise workout recommendation is retrieved from said at least one database comprising previously-stored exercise workout recommendations whenever said first exercise workout recommendation is generated, and said second exercise workout recommendation is generated whenever said first exercise workout recommendation is retrieved from said at least one database comprising previously-stored exercise workout recommendations.

11. The method of claim 10 wherein:
A. said first exercise workout recommendation is generated and, together with said measured weight and said measured bioimpedance, are communicated to said one or more network server(s) for storage in said at least one of the one or more database(s); and
B. said second exercise workout recommendation is retrieved by said one or more network server(s) or said fixed location application from said at least one database comprising previously-generated and stored exercise workout recommendations corresponding to other users with similar values of measured weight and measured bioimpedance.

12. The method of claim 10 wherein:
A. said first exercise workout recommendation is retrieved by said one or more network server(s) or said fixed location application from said at least one database comprising previously-generated and stored exercise workout recommendations corresponding to other users with similar values of measured weight and measured bioimpedance; and
B. said second exercise workout recommendation is generated and, together with said measured weight and said measured bioimpedance, are communicated to said one or more network server(s) for storage in said at least one of the one or more database(s).

13. The method of claim 10 wherein at least one of any of said generated first, second, and third exercise workout recommendations comprise said one or more first, second, and third exercise workout instructions, respectively, ordered in such manner as to provide time for recovery of muscle groups exercised during preceding exercise workout instructions.

14. The method of claim 10 wherein the step of generating at least one of any of said first, second, and third exercise workout recommendations comprise the use of at least one of any additional data pertaining to said user's age, height, sex, somatotype, goal data, exercise workout preferences, health or injury history, exercise preferences, or previously-generated exercise workout recommendation(s).

15. The method of claim 14 wherein the step of generating at least one of any of said first or second, and third exercise workout recommendations comprise either the use of an exercise workout generation method selected by the system based on at least one of any of said user's measured weight, bioimpedance, and said additional data, or the use of an exercise workout generation method selected by the user.

16. The method of claim 10 wherein the step of measuring the bioimpedance of said user comprises the use of one or more of any of a periodic fixed-frequency sinusoidal signal, a periodic fixed-frequency non-sinusoidal signal, a periodic variable-frequency sinusoidal signal, and a periodic variable-frequency non-sinusoidal signal.

17. A system for generating a personalized exercise workout, the system comprising:
A. at least one weighing scale;
B. at least one bioimpedance measurement machine comprising two or more analog biometric sensors in electrical signal communication with
  i. the body of a user,
  ii. at least one alternating current (AC) analog voltage signal generator,
  iii. at least one analog AC voltage measuring device, and
  iv. at least one analog AC current measuring device; and
C. one or more network servers comprising one or more databases, at least one of said one or more databases comprising previously-stored values of measured weight and measured bioimpedance data and the identity of the user associated with said data; wherein the system is configured to:
  a. determine or receive the geographic location of a particular system user;
  b. measure the weight of a particular system user via said at least one weighing scale;
  c. measure the bioimpedance of said particular system user at one or more frequencies via said at least one bioimpedance measurement machine;
  d. compare said measured weight and measured bioimpedance data with previously-stored values of measured weight and measured bioimpedance data associated with the identity of every other system user present in said at least one of the one or more databases;

e. determine the identity of said particular user based on the similarity of said measured weight and measured bioimpedance data to said previously-stored values of measured weight and measured bioimpedance data;

f. replace said previously-stored weight and measured bioimpedance data associated with the identity of the particular user with the measured weight and measured bioimpedance data in said one or more database(s);

g. generate an exercise workout recommendation for said particular system user using said measured weight and said measured bioimpedance of said particular system user along with a list of available exercise resources and exercise machines at more than one exercise resource location(s) within a specified distance from said geographical location of said user; and h. provide said exercise workout recommendation and said list of available exercise resources and exercise machines to said particular system user.

18. The system of claim 17 wherein said at least one AC analog voltage signal generator is configured to generate one or more of any of a periodic fixed-frequency sinusoidal signal, a periodic fixed-frequency non-sinusoidal signal, a periodic variable-frequency sinusoidal signal, and a periodic variable-frequency non-sinusoidal signal.

19. The system of claim 17 wherein said at least one analog AC voltage measuring device and said at least one analog AC current measuring device further comprise one or more frequency-selective filters configured to either measure said bioimpedance data at one or more specific frequencies or to exclude measurement of said bioimpedance data at one or more specific frequencies.

20. The system of claim 17 wherein said at least one analog AC voltage measuring device and said at least one analog AC current measuring device further comprise one or more series or parallel resistive-inductive-capacitive networks operative to transform measurements of bioimpedance to a different range of measured bioimpedance values.

* * * * *